United States Patent
Kuracina

(10) Patent No.: US 11,612,693 B1
(45) Date of Patent: Mar. 28, 2023

(54) METHOD AND APPARATUS TO REDUCE THE DEADSPACE IN SYRINGES AND SMALL-BORE DEVICES

(71) Applicant: Thomas C. Kuracina, Carson City, NV (US)

(72) Inventor: Thomas C. Kuracina, Carson City, NV (US)

( * ) Notice: Subject to any disclaimer, the term of this patent is extended or adjusted under 35 U.S.C. 154(b) by 0 days.

(21) Appl. No.: 17/990,155

(22) Filed: Nov. 18, 2022

Related U.S. Application Data

(63) Continuation of application No. 17/977,607, filed on Oct. 31, 2022.

(60) Provisional application No. 63/415,029, filed on Oct. 11, 2022, provisional application No. 63/372,045, filed on Feb. 7, 2022, provisional application No. 63/361,425, filed on Dec. 20, 2021, provisional application No. 63/360,847, filed on Nov. 1, 2021, provisional application No. 63/360,809, filed on Oct. 29, 2021.

(51) Int. Cl.
*A61M 3/00* (2006.01)
*A61M 5/31* (2006.01)

(52) U.S. Cl.
CPC ... *A61M 5/3146* (2013.01); *A61M 2005/3123* (2013.01)

(58) Field of Classification Search
CPC ......... A61M 2005/31523; A61M 2005/31516; A61M 5/34; A61M 5/3129; A61M 5/3134; A61M 2005/3123; A61M 5/315; A61M 5/3146
See application file for complete search history.

(56) References Cited

U.S. PATENT DOCUMENTS

| | | | |
|---|---|---|---|
| 4,966,588 A | 10/1990 | Rayman et al. | |
| 5,059,174 A | 10/1991 | Vaillancourt | |
| 5,125,415 A | 6/1992 | Bell | |
| 5,135,491 A | 8/1992 | Baldwin | |
| 5,282,981 A | 2/1994 | Adams et al. | |
| 5,858,000 A | 1/1999 | Novacek | |
| 5,865,803 A * | 2/1999 | Major | A61M 5/31511 604/122 |
| 5,902,269 A | 5/1999 | Jetzen | |
| 5,902,277 A | 5/1999 | Jetzen | |
| 5,944,698 A | 8/1999 | Fischer et al. | |
| 5,964,737 A | 10/1999 | Caizza | |
| 6,010,486 A | 1/2000 | Carter et al. | |
| 6,267,154 B1 | 7/2001 | Felicelli et al. | |
| 6,454,745 B1 | 9/2002 | Donnan et al. | |
| 6,955,660 B2 | 10/2005 | Fisher | |

(Continued)

FOREIGN PATENT DOCUMENTS

WO    WO-9209320 A1 *  6/1992    ............ A61M 5/315

*Primary Examiner* — Rebecca E Eisenberg
(74) *Attorney, Agent, or Firm* — Edell, Shapiro & Finnan, LLC

(57) ABSTRACT

Methods and apparatus to reduce deadspace in syringes and other devices with the use of volume displacing members that occupy space within one or more interior spaces of such devices. The volume displacing members are also equipped with one or more internal flow passages that facilitate a flow of a fluid through it. The volume displacing members are also adapted to cooperate with features of the devices that house them to form air-tight and liquid-tight seals that at least partially determine a fluid pathway through the devices.

18 Claims, 21 Drawing Sheets

(56) References Cited

U.S. PATENT DOCUMENTS

| | | |
|---|---|---|
| 7,140,592 B2 | 11/2006 | Phillips |
| 7,534,233 B2 | 5/2009 | Schiller et al. |
| 8,006,953 B2 | 8/2011 | Bennett |
| 9,295,788 B2 | 3/2016 | Green |
| 9,616,214 B2 | 4/2017 | Stout et al. |
| 10,183,129 B1 | 1/2019 | Vitello |
| 10,315,024 B1 | 6/2019 | Vitello et al. |
| 10,888,672 B1 | 1/2021 | Vitello |
| 11,065,372 B2 | 7/2021 | Stender et al. |
| 11,071,530 B2 | 7/2021 | Wang et al. |
| 11,207,469 B1 | 12/2021 | Caizza |
| 11,278,681 B1 | 3/2022 | Banik et al. |
| 2001/0056259 A1 | 12/2001 | Skinkle et al. |
| 2003/0040720 A1 | 2/2003 | Steube |
| 2004/0006312 A1 | 1/2004 | Donnan et al. |
| 2004/0016460 A1 | 1/2004 | Newburg |
| 2006/0064060 A1* | 3/2006 | Lin ................ A61M 5/5013 604/110 |
| 2009/0054834 A1 | 2/2009 | Zinger et al. |
| 2011/0282298 A1 | 11/2011 | Agian et al. |
| 2012/0226239 A1 | 9/2012 | Green |
| 2022/0273931 A1 | 9/2022 | Jiang et al. |
| 2022/0280729 A1 | 9/2022 | Caizza |

\* cited by examiner

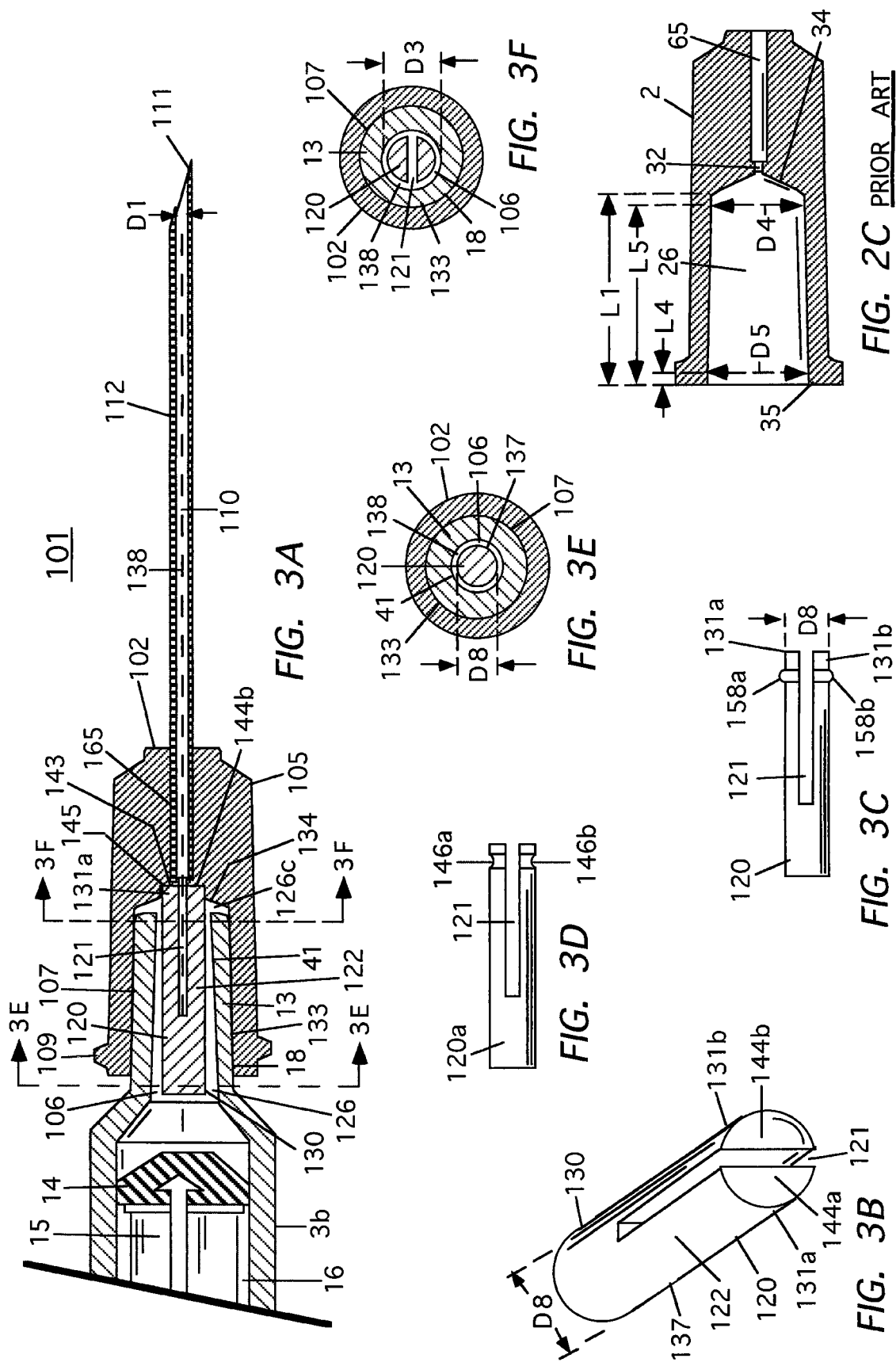

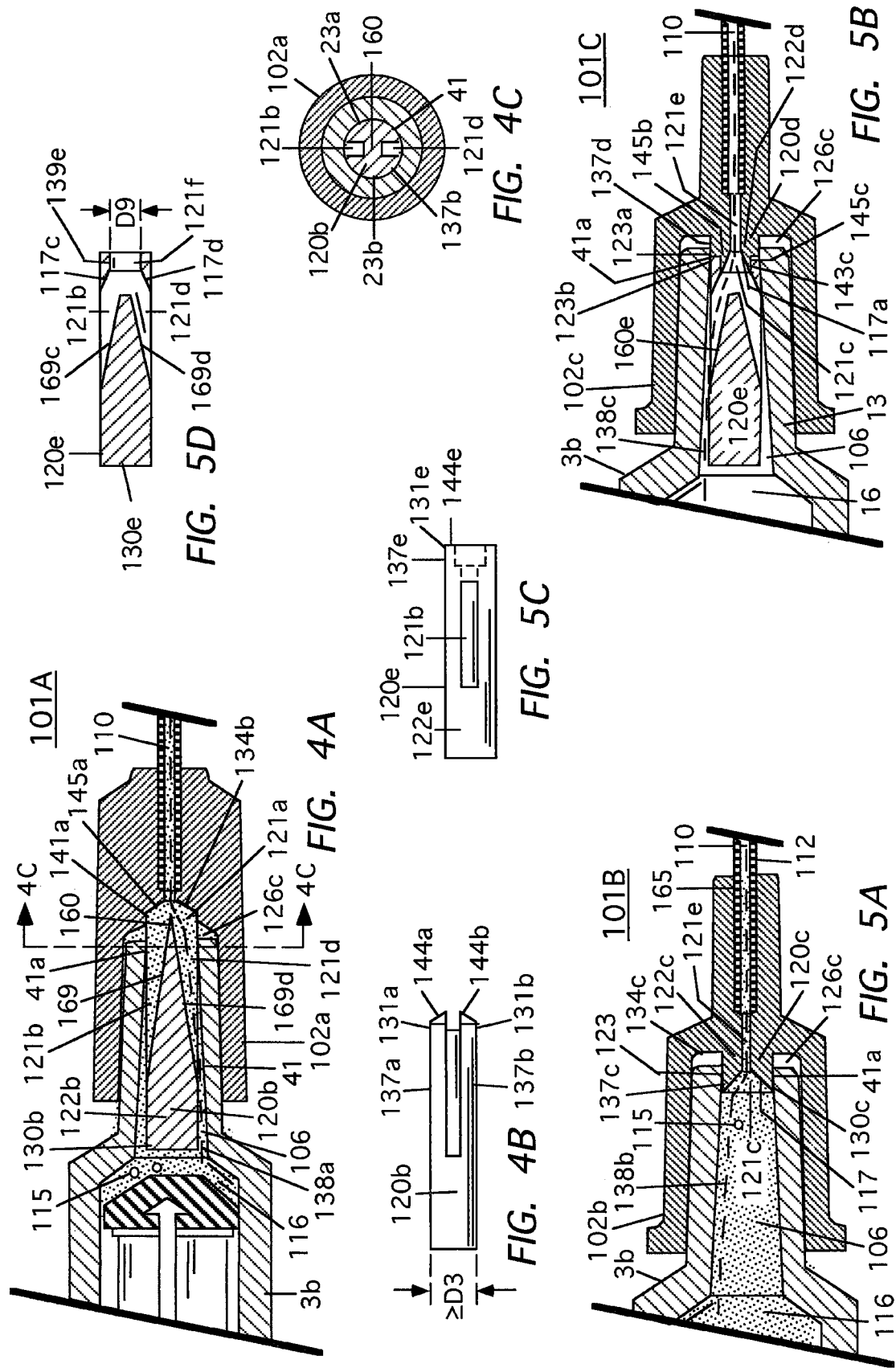

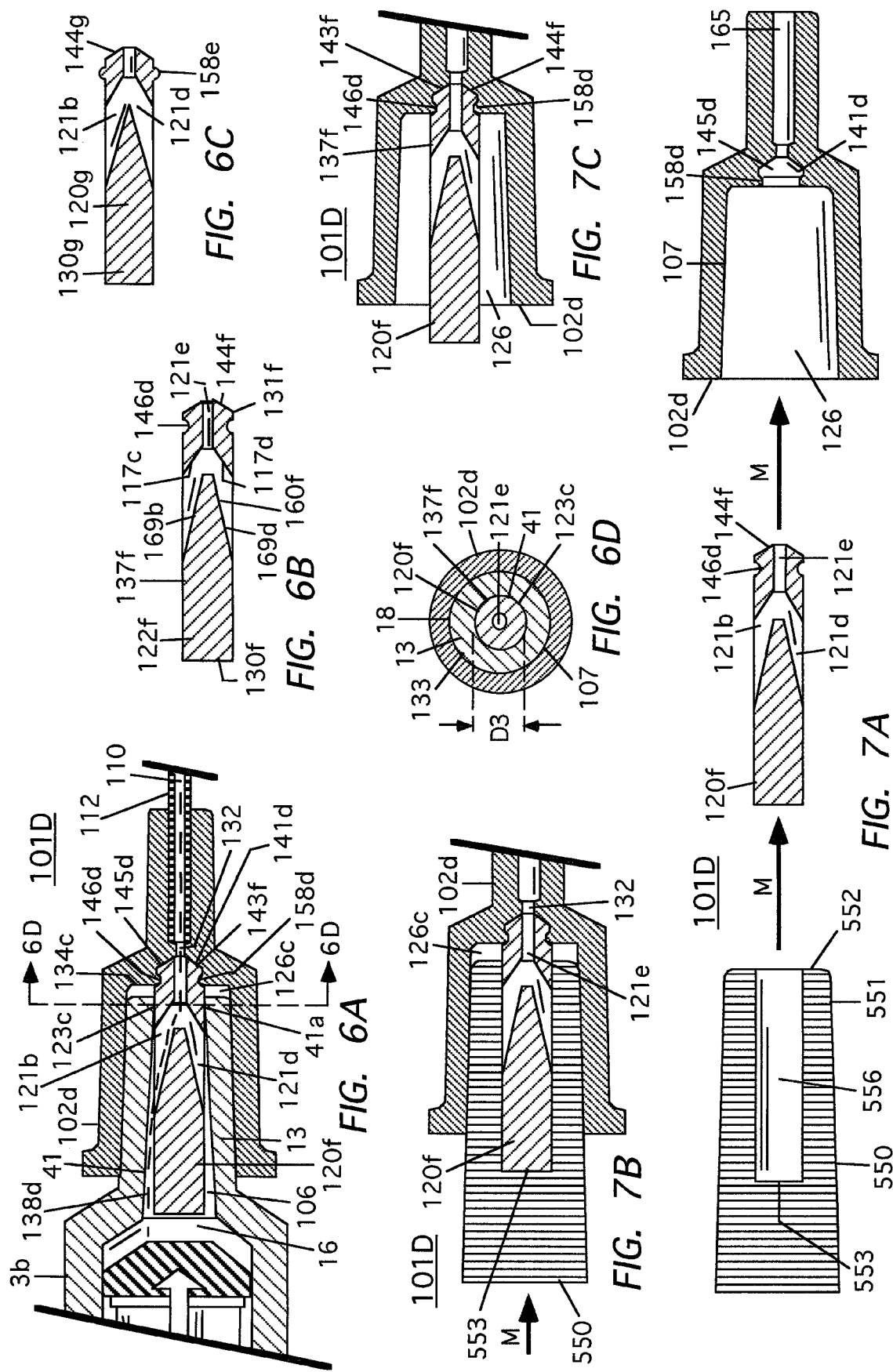

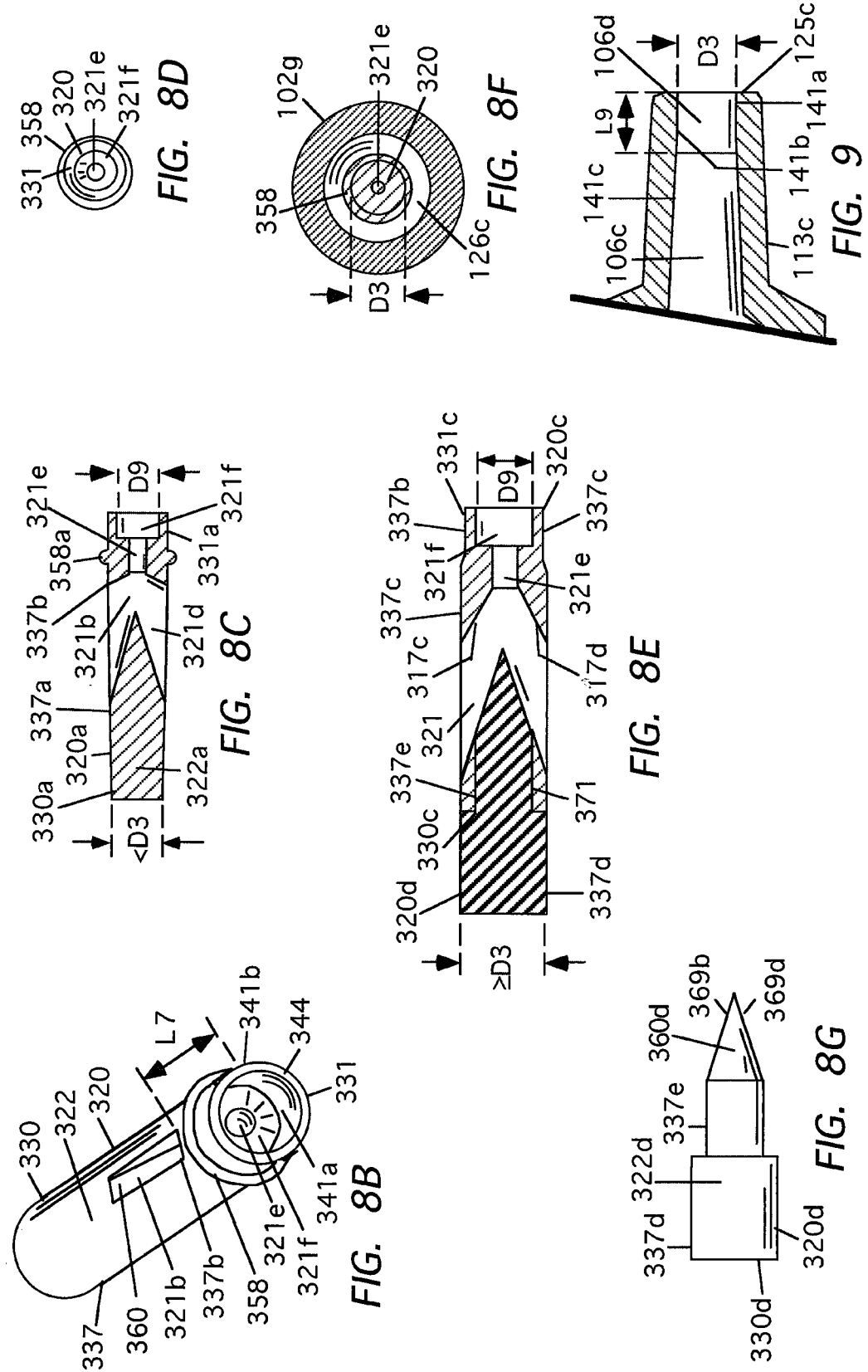

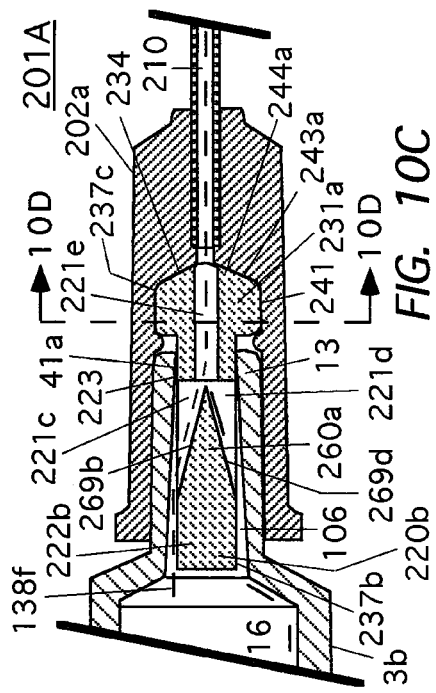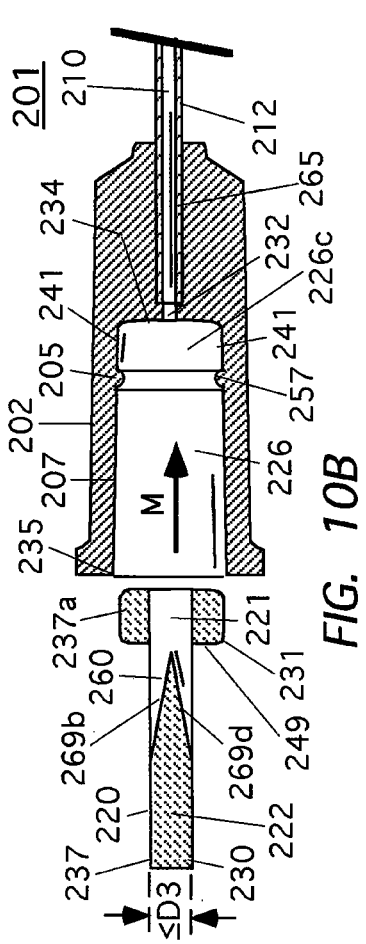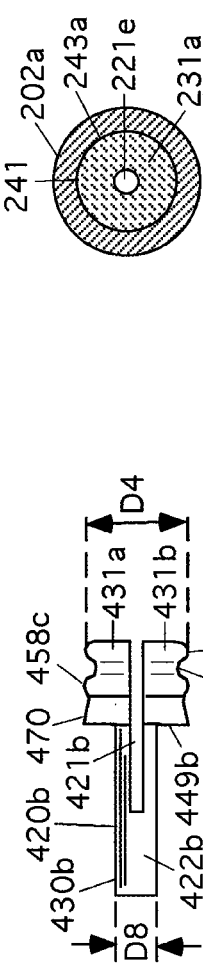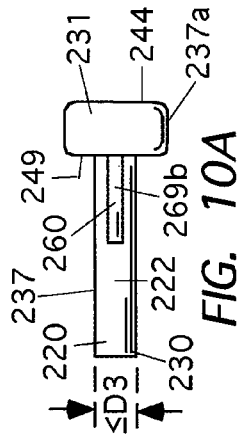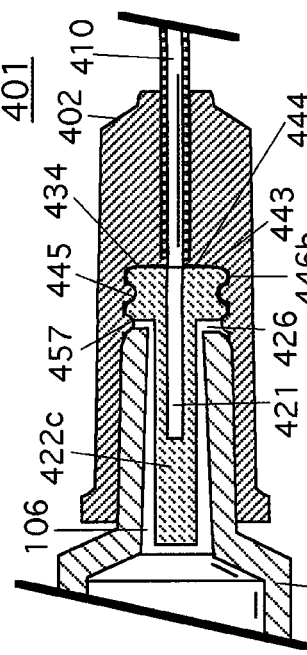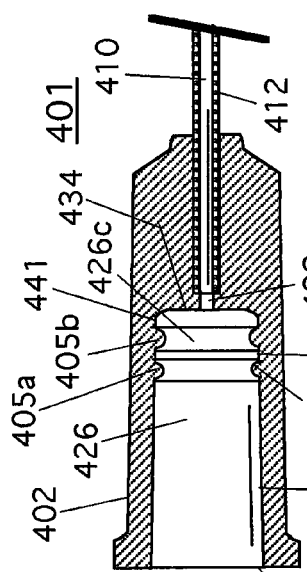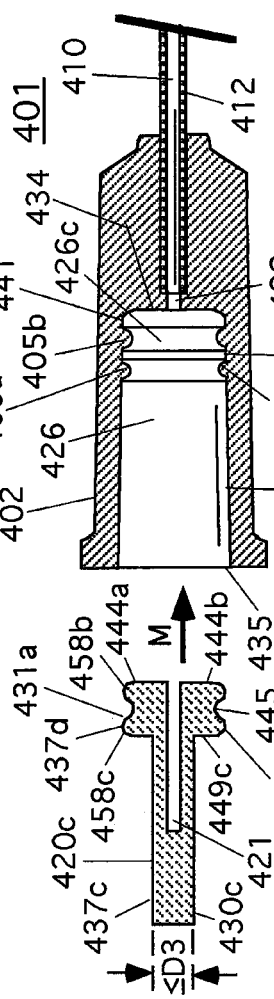

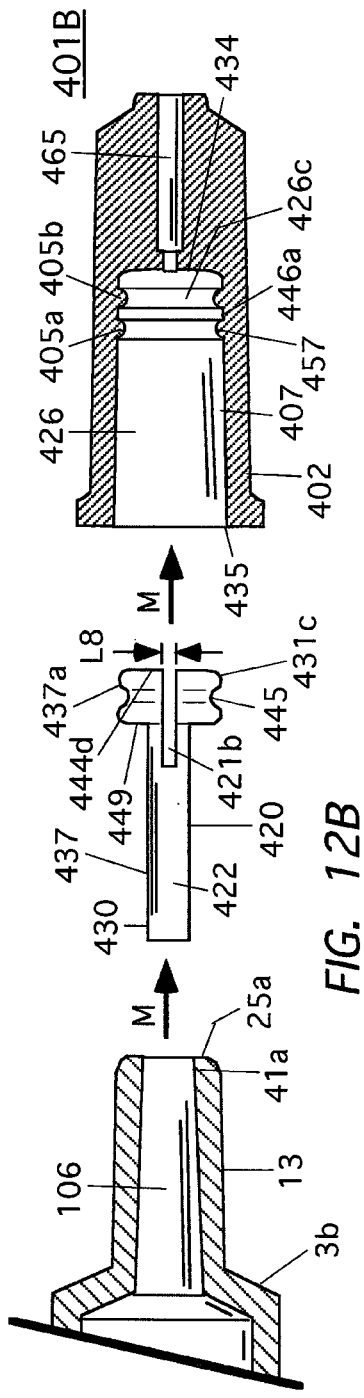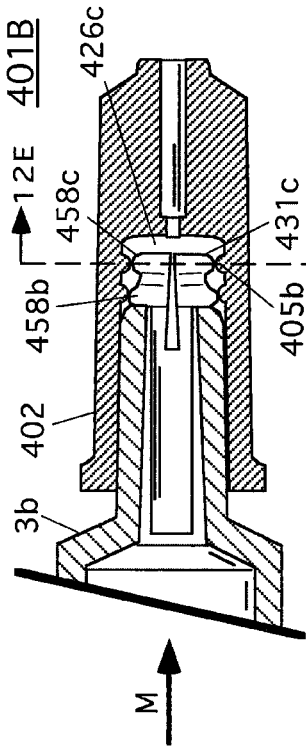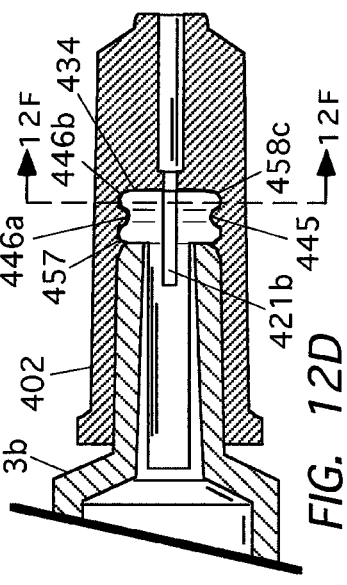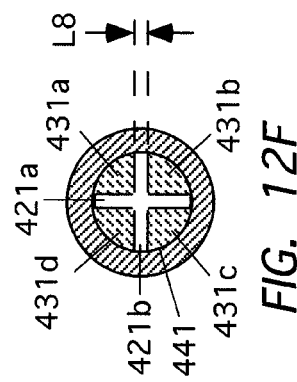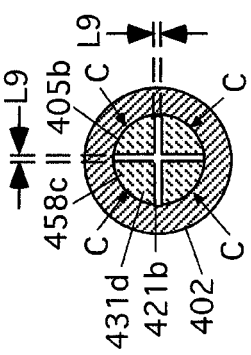

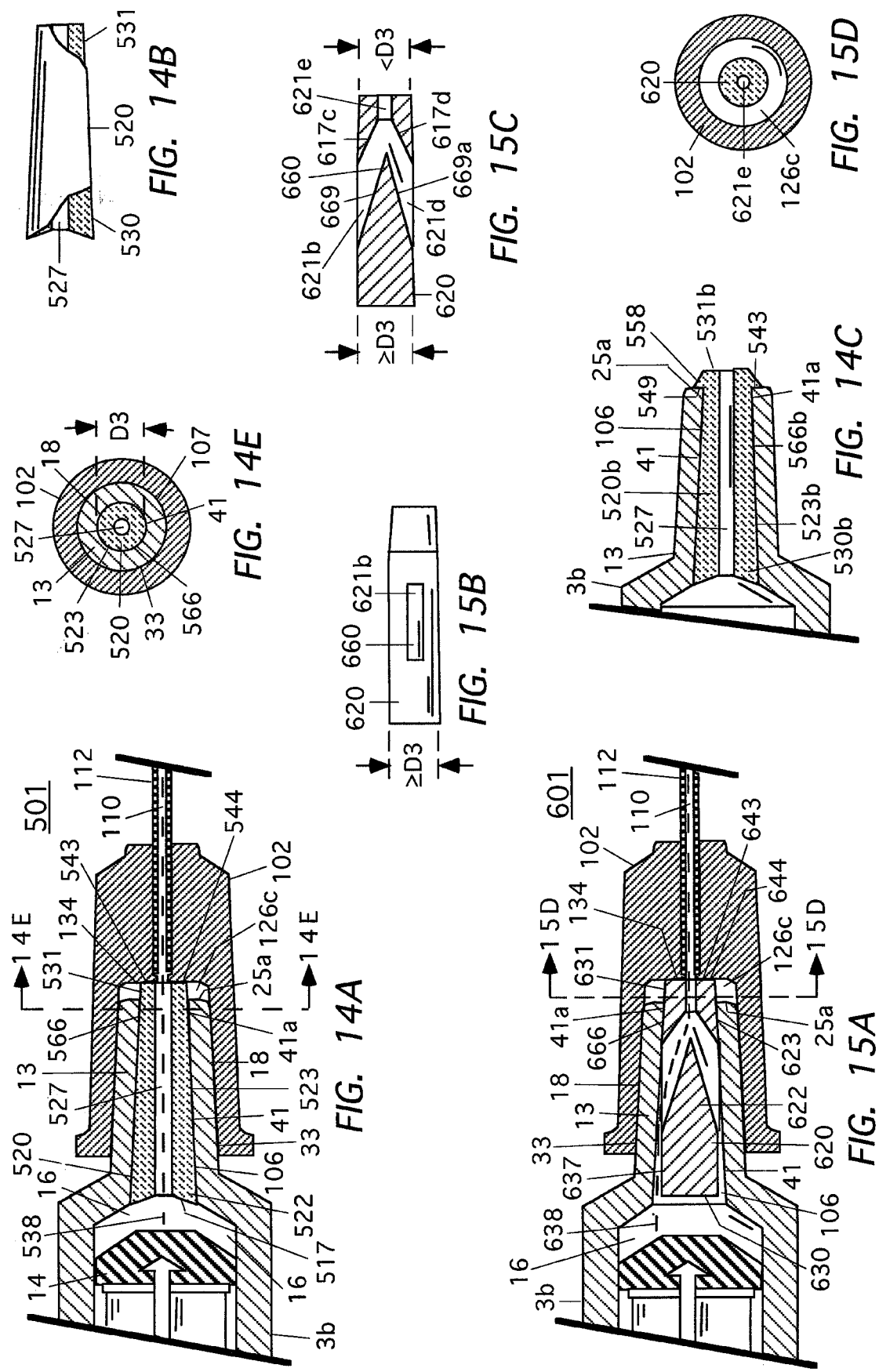

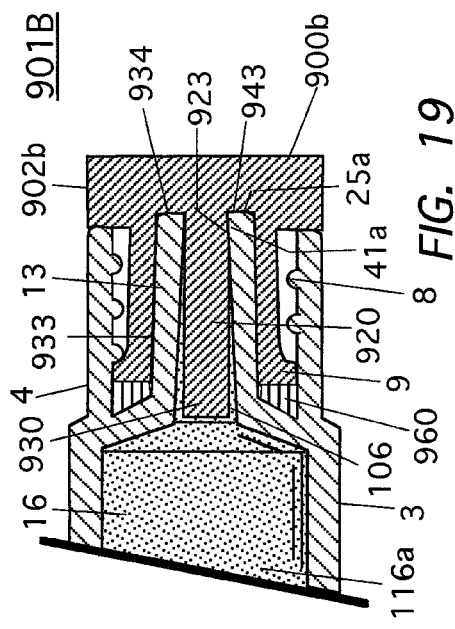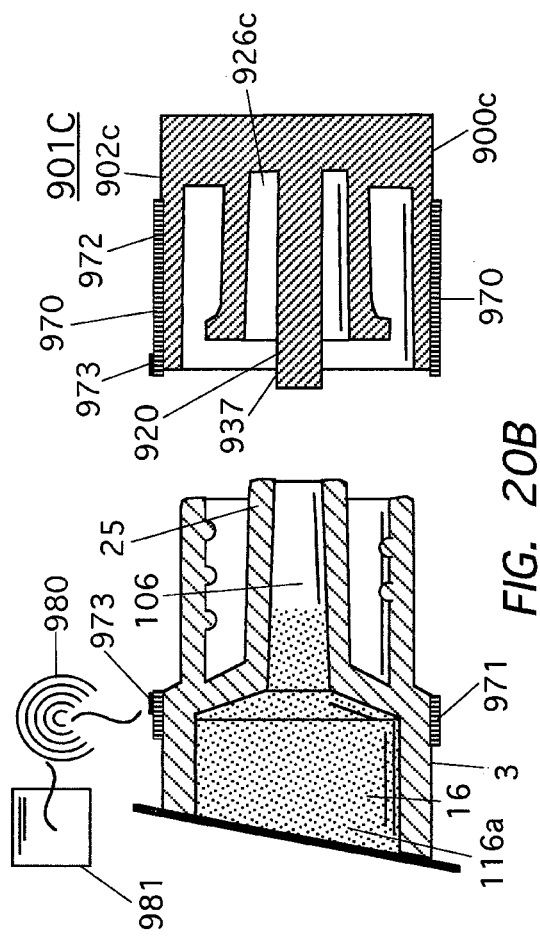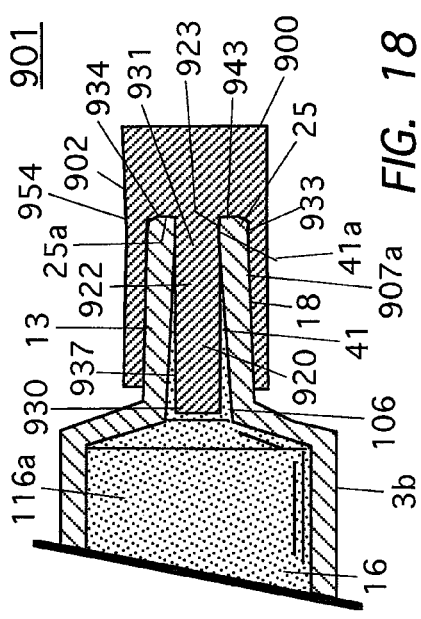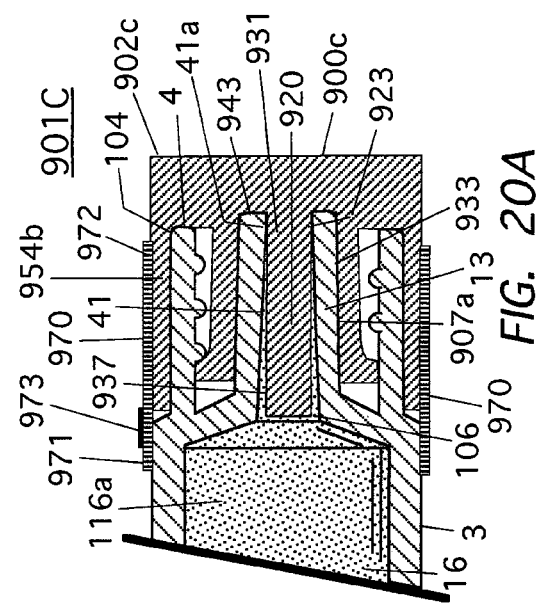

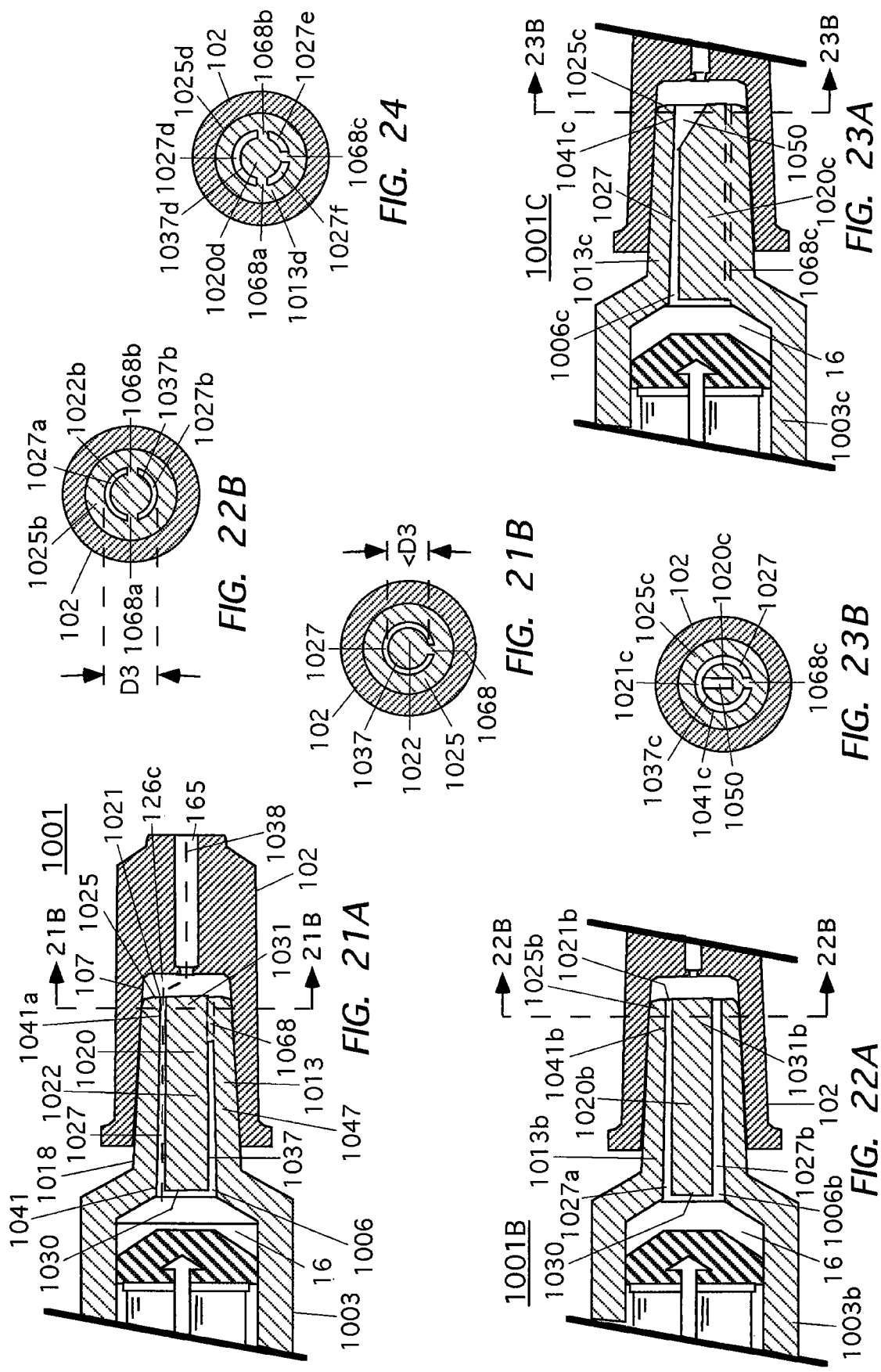

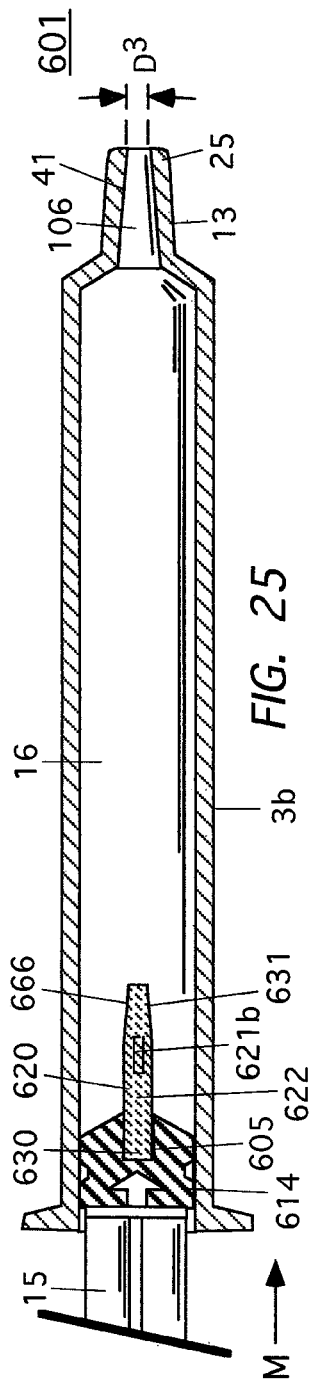
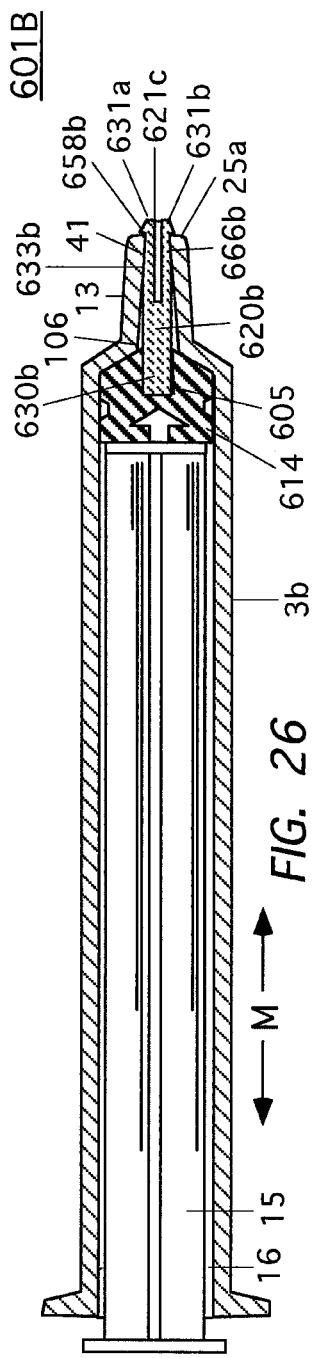
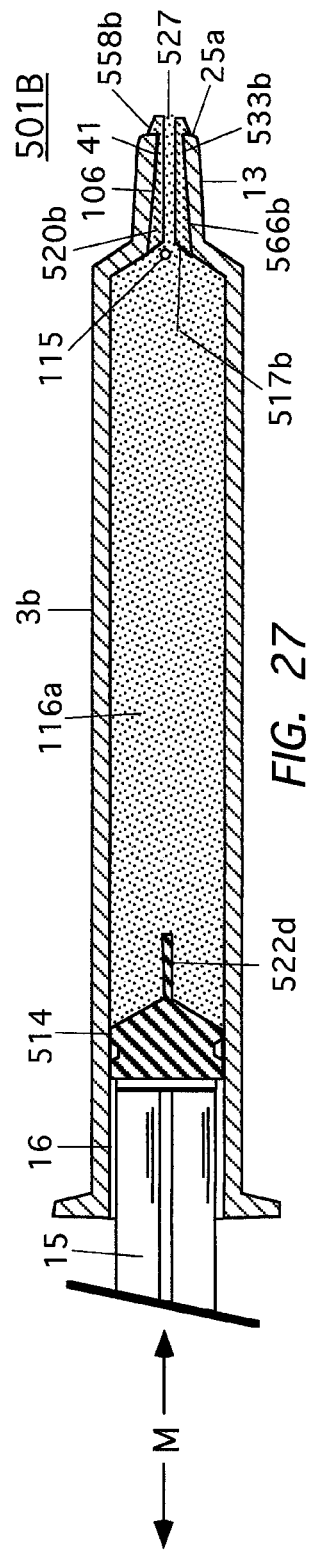

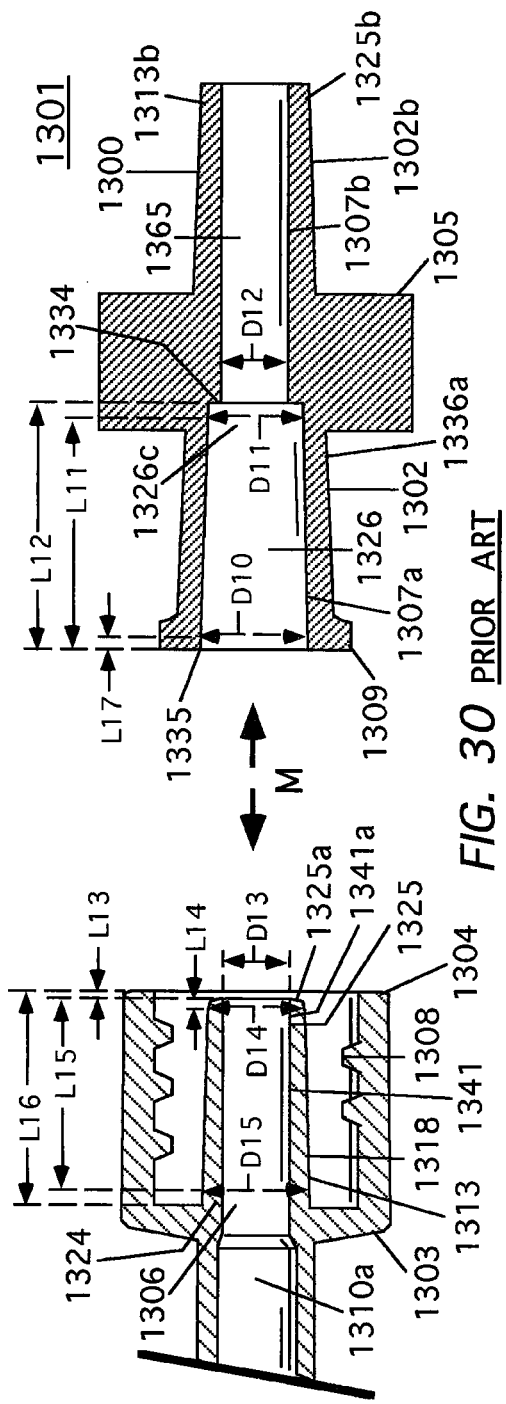
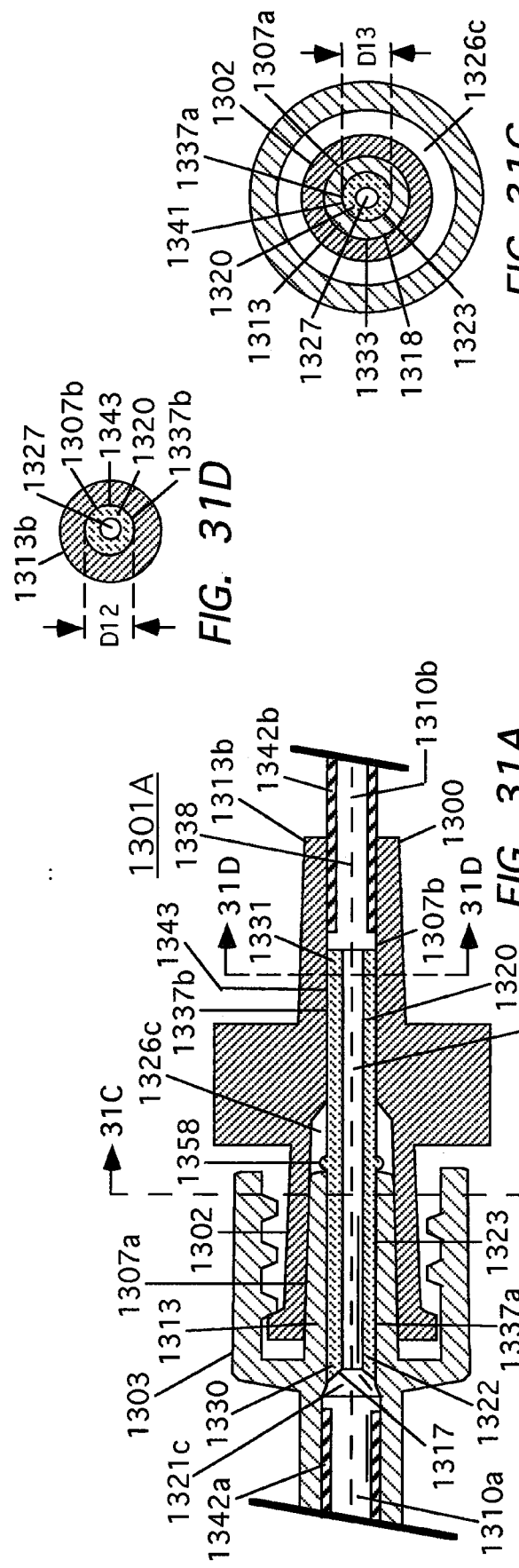
FIG. 30 PRIOR ART
FIG. 31A
FIG. 31C
FIG. 31D

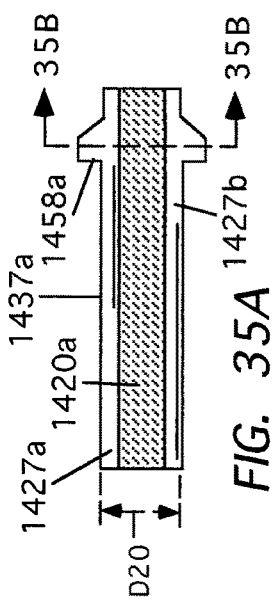
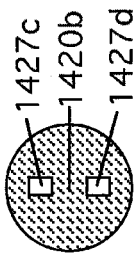
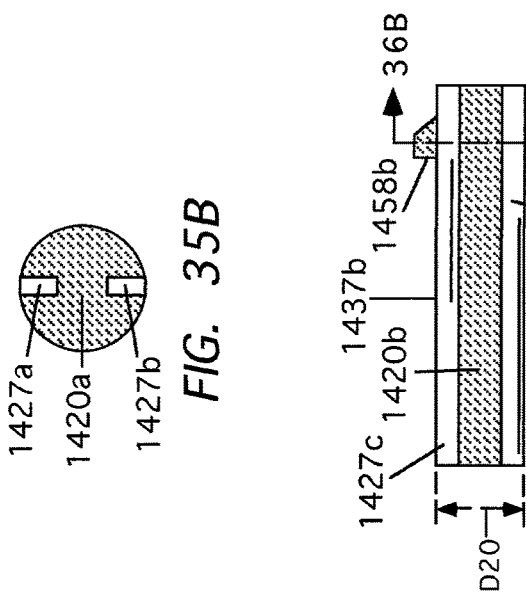
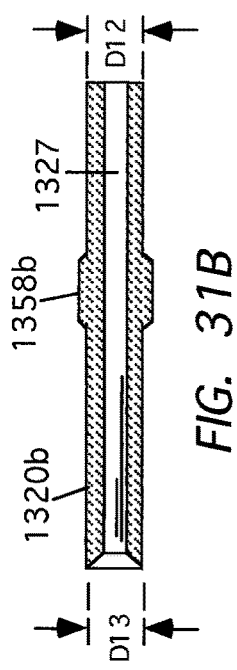
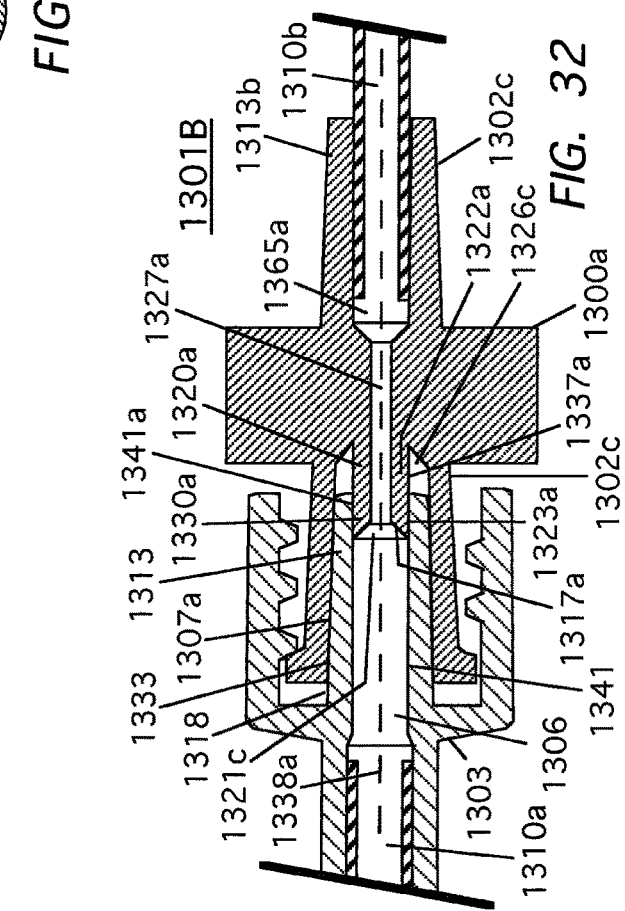

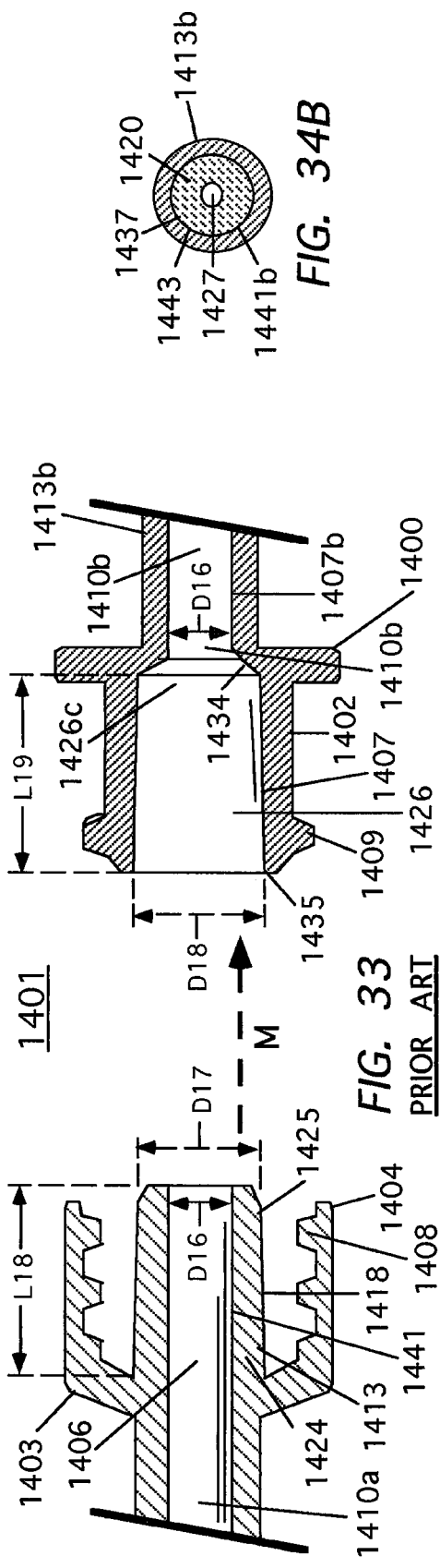
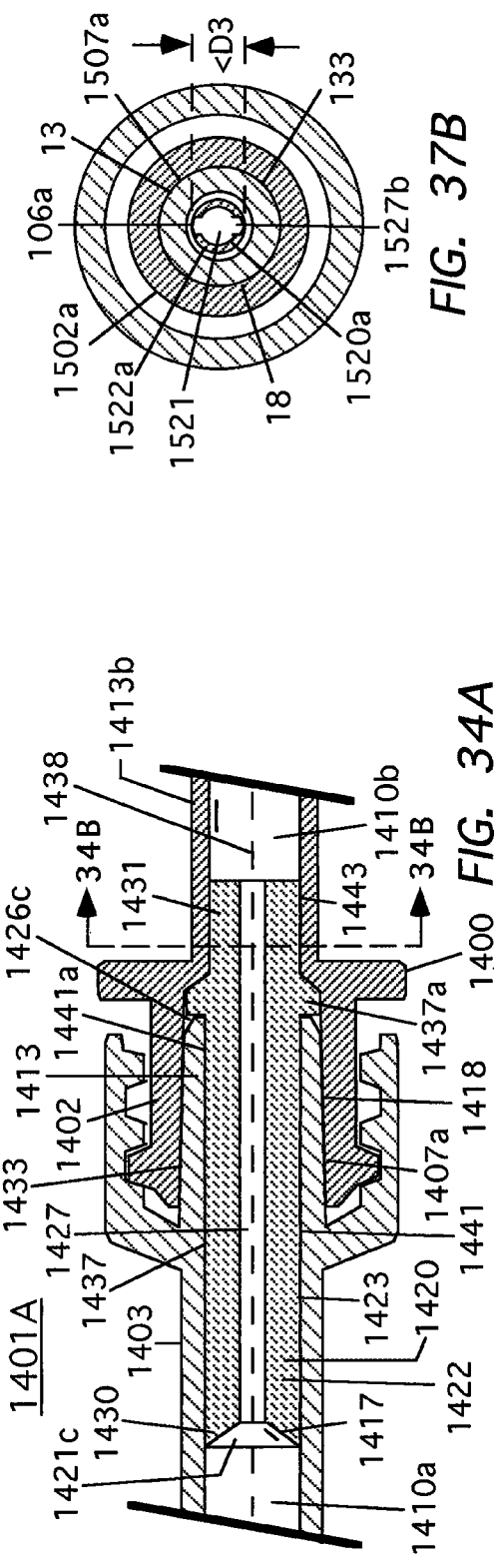

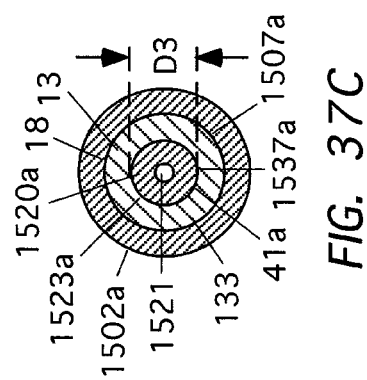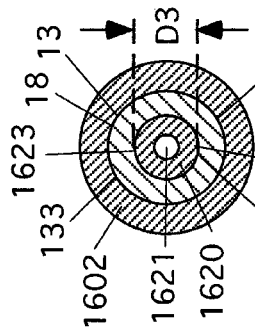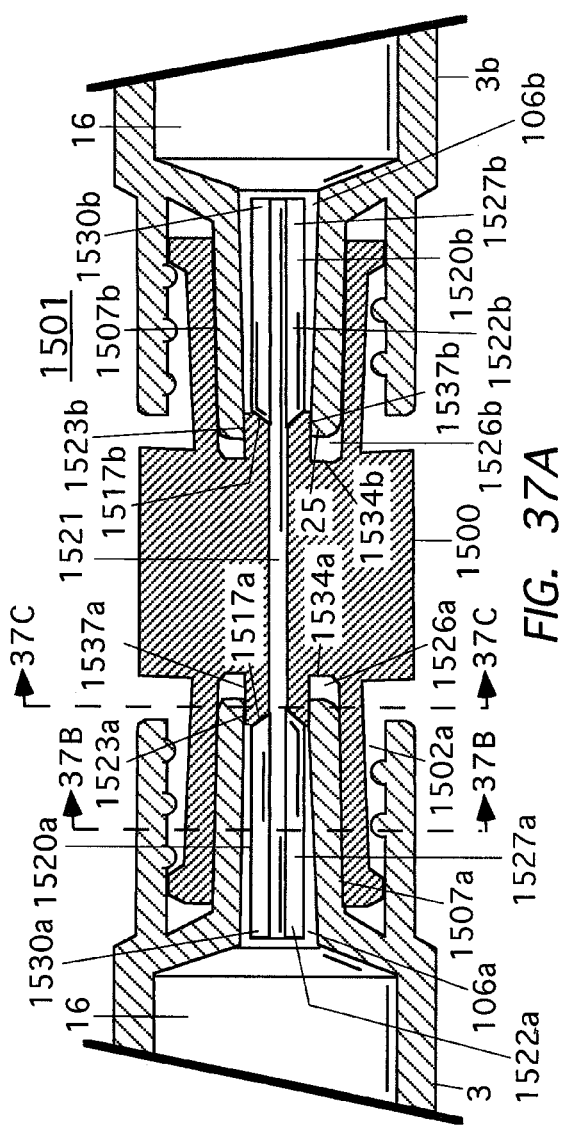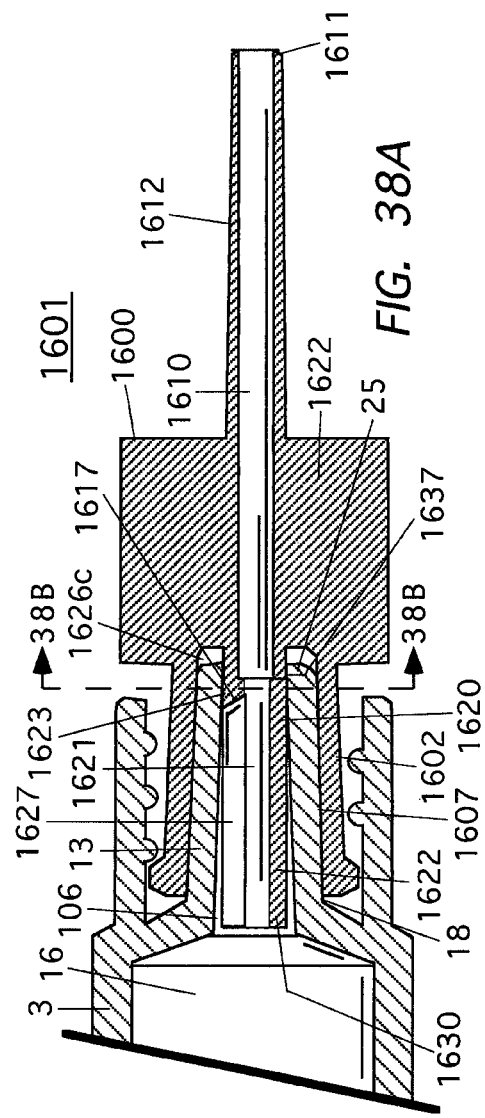

METHOD AND APPARATUS TO REDUCE THE DEADSPACE IN SYRINGES AND SMALL-BORE DEVICES

CROSS-REFERENCE TO RELATED APPLICATIONS

This application is a continuation of application Ser. No. 17/977,607, filed Oct. 31, 2022, which relates to and claims the benefit of filing dates of the following United States Provisional Patent Applications: (1) Ser. No. 63/360,809, filed Oct. 29, 2021; (2) Ser. No. 63/360,847, filed Nov. 1, 2021; (3) Ser. No. 63/361,425, filed Dec. 20, 2021; (4) Ser. No. 63/372,045, filed Feb. 7, 2022, and (5) Ser. No. 63/415,029, filed Oct. 11, 2022. Each of the above-referenced provisional patent applications is incorporated herein in by reference in its entirety.

FIELD

The present invention relates to a method and apparatus for delivering or dispensing fluids or gasses through one or more small-bore device, connector, fitting, dispenser, or adapter, singularly or in combination, for medical devices such as intravascular, enteral feeding, neuraxial or breathing systems.

BACKGROUND

Medical devices, such as syringes, catheters, ports, valves, fittings, tubing sets and IV fluid bags are well known in the art for delivering fluids, medication, contrast dyes, diluents, anesthesia, nutrition and gases and the like. Existing delivery devices may include unique designs to reduce the deadspace in the fluid path or interior through-passage such as permanently bonded needle/syringe combinations and retracting needle syringes. These devices do not conform to the ISO 10369-7 Luer Standard for hypodermic and intravascular applications, so their clinical use is limited and incompatible with the majority of luer-based devices, fittings and adapters universally used in medicine. Additional ISO 80369 Standards, including the neuraxial Luer Standard (ISO 80369-6) and enteral Luer Standard (ISO 80369-3) were established to specify the design of small-bore connectors, adapters and tubing for various clinical applications that are dissimilar as a result of tubing misconnections that resulted in harmful, and even fatal errors.

An example of the need to standardize medical connectors was evident at the 1988 U.S. Ramstein Air Base air show disaster in Germany when miscommunication between the US military and German paramedics resulted in the inability to place IV catheters and infuse the injured due to the incompatibility of two different intravenous connectors used by first responders.

Syringes are universally used in medicine and are provided sterile, in either a fillable or a prefilled configuration. The needle may be integrally attached to the syringe, or the syringe may include a luer fitting that comprises a press or slip fitting or a threaded luer-lock fitting for attaching a needle or other luer-based apparatus. Some enteral luer syringes are sold in a reusable, stainless steel configuration.

Hypodermic needles include a lubricant such as medical grade silicone on the needle shaft to reduce penetration drag force and minimize patient discomfort when a medicant is administered. The lubricant and beveled edge of the needle are compromised when the same needle is used to fill a syringe (piercing the elastomeric stopper of a medicine vial) and administer an injection. A low-cost fill needle can be used to aspirate medication or diluent into a fillable needle/syringe apparatus and then removed and replaced with a fresh, sterile needle or luer connector to administer the injection or infusion. Some fillable syringes include an integrally formed needle or may comprise a separate luer-based needle fitted to the syringe to fill the syringe with the prescribed dose of medicine or diluent. Any air trapped in the medication or fluid within a fillable syringe and needle or prefilled syringe must be expelled before the fluid is administered into tissue, a port, needleless valve or infusion stream or other luer-based device. To remove the air from the fluid in the syringe/needle apparatus, the filled syringe is positioned in an upright manner with the needle or luer fitting at the top. The syringe is repeatedly tapped on the side to release or purge any air pockets or bubbles from the fluid in the syringe and hub to rise and migrate up through the fluid path or interior through-passage of the syringe and luer hub and out of the distal end of the apparatus, that may include a hypodermic needle, as the plunger rod is advanced to the prescribed dose. The injection or infusion can then be administered.

The advantage of luer connectors is their interoperability between the male nozzle and female hub spanning a broad spectrum of medical devices, fields and procedures. The distal tapered, truncated or frustoconical cone or nozzle of a male luer syringe or male luer connector, having an interior cavity, is inserted within the interior cavity of a female luer hub, both forming a combined deadspace interior cavity with an inside diameter that exceeds the inside diameter of the through-passage or lumen of a hypodermic needle or infusion line. When the plunger rod/piston of a syringe is advanced to the distal end of the syringe barrel, the great majority of medicine or fluid is moved through the hollow luer nozzle and through a female luer hub, but the combined interior cavity of formed between the luer fittings leaves a deadspace of approximately 7-10% of a 0.5-milliliter (ml) dose within the luer apparatus and unadministered.

A number of U.S. patents and published applications describe medical needles having a means to reduce dead space in a fluid path. These are U.S. Publication No. 2011/0282298 (Agian et al), U.S. Pat. No. 5,964,737 (Caizza), U.S. Publication No. 2003/004720 (Steube), U.S. Pat. No. 5,902,269 (Jentzen), U.S. Pat. No. 5,902,277 (Jentzen), U.S. Pat. No. 6,010,486 (Carter et al.), U.S. Pat. No. 6,955,660 (Fisher) and U.S. Pat. No. 9,295,788 (Green).

None of these teachings address the aerodynamics of removing of air or gaseous bubbles from the fluid within an internal passageway of a hypodermic apparatus prior to administering an injection or infusion. When a drug or drug bolus are injected from a syringe, safe clinical practice is to remove all air from the fluid in the syringe or infusion device prior to administration. In the 2012 Accidental Intravenous Infusion of Air study published in the Infusion Nurses Society, Wilkins and Unverdorben observe that a spherical bubble as small as 0.2 mm may cause detectable cerebral ischemia. The International Electromechanical Commission (IEC) has published a standard, Part 2:24 1998-02(E):41 the safety of administering infusions. The IEC standard does not present a universally safe level of air infusion, so there is no maximum safe dose of air infusion. A clinical injection or infusion of air is rare but may precipitate an adverse or fatal event.

Air bubbles in liquid have a strong tendency to combine and coalesce and naturally tend to enlarge and take a spherical shape. When a bubble passes through a smaller, restricted orifice or channel like that in a small-bore connector or needle, the bubble or bubbles compress and form an ellipsoidal shape increasing surface tension that acts as an attachment force and tends to cling to a surface. One can sense the increased surface tension of a sphere by squeezing and hugging a beach ball filled with air.

Agian et al. '298 teaches a coupler comprising a solid, dose-sparing insert positioned within a luer syringe tip attached to a female hub with microneedles for administering an intradermal injection. The solid insert with closed ends is surrounded by an open flow path diametrically formed between the solid exterior of the insert and the surface of the inner wall of the nozzle of a male syringe tip and includes a dead-end interior cavity within the female hub outside the flowpath with surfaces where air bubbles can attach. The flow path narrows between the distal end of the solid insert and distal end of the inner cavity of the female luer hub forming a bottleneck, not only restricting fluid flow but also compressing any bubbles present in the fluid and increasing the surface tension and attachment force of any bubbles to the surfaces of the insert and female hub as fluid moves through the coupler. An air bubble or bubbles can attach to these surfaces during aspiration and release during the injection or infusion. There is no need to expel any air from the medication in the Agian et al. insert teaching since the injection is administered on the surface of the skin.

The interfacial phenomena of bubble formation and growth, and attachment or detachment from a surface in a fluid path must be considered in the design of small-bore devices where an air bubble or bubbles must be purged prior to administering or infusing a medicine, solution, anesthesia, or the like to a patient. If an air bubble or bubbles are not purged from the device and inadvertently enter the venous system, they get filtered out when the blood reaches the lungs. Air diffuses across the barrier between bloodstream and air in the lungs, being expelled back out of the blood and safely leaving our system. But if an air bubble or bubbles inadvertently enter the arterial system, they could cause an adverse event when reaching the heart where they can block a chamber and stall the pumping action or cut off blood flow in the brain and cause a stroke. Therefore, any restrictive, stepped or reducing feature in the fluid path of a small-bore device or connector must minimize or eliminate any rear-facing interfacial surface forming a dead spot for an air bubble or bubbles to cling to when filling or dispensing fluid from a syringe or infusion device.

A laminar flow fluid path, characterized by a smooth or regular path, is preferred in a small-bore device or devices to reduce the probability of interfacial bubble attachment and reduce or eliminate any turbulence.

The radius of a spherical bubble is directly proportional to the surface tension of the orifice, so when a bubble becomes elongated as it is squeezed as it moves through a restricted space tends to attach to the surface. Irregularities and dead spots where the flow stalls within the fluid path of a passageway also create an undesirable pocket of turbulence and a circular current for an air bubble or bubbles to attach to a surface.

The Jentzen '269 and '277 teachings are limited to a syringe/needle apparatus having a unique syringe piston stopper to expel the medication within the interior cavity of a male luer nozzle but leaves medication within the interior cavity of the female hub. Caizza '737 teaches a resilient member or sleeve, with an inside through-channel, displacing a portion of the interior cavity of the distal end of a female hub formed when a male luer nozzle is positioned within the female hub. The Carter '486 teaching is limited to a syringe/needle apparatus having a unique syringe stopper to expel the medication and retract a needle within the syringe barrel after the injection is administered. A retractable needle attached to an inner hub that includes a frangible portion and a piercing member are required to practice the '486 teaching. Additionally, retracting needles are well known to regurgitate fluid from the needle as the needle and hub retract into the syringe barrel, and to ooze fluid from the distal tip afterwards.

Steube '720 teaches a syringe attached to a needle having a female luer hub, designed to minimize fluid waste with an interior chamber formed within the elongated barrel tip (luer nozzle), comprising a needle hub attached to a needle, having a needle cavity or lumen, attached to an elongate needle support extending proximally through the length of the interior chamber of the elongated barrel tip and beyond the open proximal end of the needle hub. Elongate needle support includes a proximal end with a length configured to engage the elastomeric tip of the plunger when the fluid has been dispensed from the syringe barrel. When the '720 needle hub is attached to the syringe tip, a dead-end interior cavity is formed between the inside wall of the elongated barrel tip (luer nozzle) and outside wall of the needle support, trapping air or air bubbles in the fluid within the dead-end interior cavity when the syringe and attached needle hub are positioned with the needle pointing up when the user is attempting to remove any air from the fluid before use. The air or air bubbles trapped within the interior cavity surrounding the needle support can release and migrate into the fluid, when the syringe position is changed with the needle no longer pointing up and particularly when the needle is pointing down, and potentially be dispensed through the needle into a patient or port. Vernacare in the UK produces low deadspace needle based on the Steube teaching.

The Fisher '660 teaching is limited to an adapter, comprising three concentrically configured seals, that connects to a syringe comprising an expansion sleeve with a central hollow lumen formed through a deformable proximal nose, having an outside surface when positioned within a luer syringe nozzle, expands to engage the inside wall of the luer nozzle forming a first seal when a separate hollow shaft or pipe, with a second central lumen and outside wall, is inserted into the first lumen of the expansion sleeve, forming a second concentrical seal between the outside wall of the pipe and inside wall of the deformable nose. In order to practice the '660 teaching, the expansion sleeve comprises an outside conical collar disposed around the periphery of the deformable nose, with an inside wall forming a third seal concentrically disposed around the outside wall of the luer nozzle. The outside conical collar of the '660 adapter teaching is not compatible with a female luer hub per Part 7, therefore is unenabled and eliminated from any industrial or commercial use and cannot be practiced.

U.S. Pat. No. 5,858,000 (Novacek) teaches a multi-piece luer syringe having a retractable needle co-operable with a separate, moveable adapter, having an elongated, distally-formed nose adapted to fit inside the interior cavity of a female luer hub, positioned within the distal end of the syringe barrel. The adapter, having an open proximal end and open distal end defining a central axial passage, is formed within a proximal protrusion in the open proximal end positioned within the syringe barrel, extending to the distal end formed within a nose positioned within the interior cavity of a female luer hub, for engaging the proximal end of the hollow needle. The adapter, having a proximal face with grooves, is positioned within the interior cavity of the syringe barrel, extending laterally from the distal protrusion to the outside diameter and in communication with the central passage for venting air from the interior of the syringe barrel. The adapter is rotatably attachable to a piston and attached to a frangible plunger, and retractable into the syringe barrel by engaging and rotating the plunger-piston into the adapter after the injection is administered. An additional seal, between the outside wall of the moveable adapter and inside wall of the syringe barrel is required to practice this teaching.

U.S. Pat. No. 8,006,953 (Bennett) teaches a one-way valve in a female luer hub. U.S. Pat. No. 9,616,214 (Stout et al.) teaches a flush enhancing luer connector with a flow expansion channel and a flow diverter configured to divert the fluid flow to the periphery of the connecting female luer space during a flush procedure to increase mixing and turbulence in the dead space created by a male luer tip. U.S. Pat. No. 6,267,154 (Felicelli et al.) teaches a removable plug including a male luer nozzle plug which tightly fits within the inside surface of the female luer lock nozzle. U.S. Pat. No. 7,140,592 (Phillips) teaches a self-sealing valve in luer connector.

In 2021, a large medical device manufacturer recalled approximately 267 million flush prefilled saline syringes due to the potential for the plunger to reintroduce air back into the syringe and cause serious adverse outcomes.

The staked insulin needle/syringe combination devices are manufactured with a short needle with a very small lumen, ranging in size between 31 G×5/16 inches and 29 G×½ inches long, include a low deadspace or "dose-sparing" feature and serve a niche market where production infrastructure is limited. Intramuscular injections are administered for prophylactic (immunization) and curative purposes and normally are administered with a luer needle/syringe ranging between 25 G×1 inch and 21 G×1.5 inch sufficient to deliver the dose in the muscle at a depth prescribed by a doctor or pharmacist.

According to Bloomberg, approximately 12.7 billion doses of COVID-19 vaccine have been administered worldwide as of this filing. The World Health organization estimated the pre-COVID-19 global market for syringes was 16 billion units per annum and market reports estimate a 10.5% CAGR through 2027, so the global syringe market demand is estimated to grow and will increase to approximately 30 billion units per year in 5 years with the advent of COVID-19. The global syringe demand will continue now that the bivalent vaccine developed by Moderna and Pfizer, consisting of the original formula and a new vaccine targeting the Omnicron BA.4 and BA.5 sub-variants of the coronavirus, has met the US FDA standards for efficacy.

SUMMARY

The present inventions generally relate to small-bore medical devices, adapters and connectors having a reduced volume or low deadspace interior cavity formed by a volume-displacing member positioned within and displacing a portion of an individual or combined interior cavity of one or more small-bore devices. A liquid-tight and air-tight connection or seal is formed with or within one or more mating components where universal interoperability between a variety of medical devices is needed to provide clinical care to patients. A vent may be included to remove air or air bubbles from the fluid prior to the injection, infusion or flush. A streamline flowpath may be configured within the interior cavity or combined cavities of the devices, adapters and connectors.

Some implementations of the present inventions herein are disclosed in luer connectors configured in the format ISO 80369-7:2021(E) Small-bore connectors for liquids and gases in healthcare, Part 7: Connectors for intravascular or hypodermic applications (noted as Part 7 throughout this application), having the male luer nozzle tip extending beyond the distal end of the luer-lock collar. Another implementation disclosed herein is configured to be operable with neuraxial or NRfit® connectors and adapters in the format ISO 80369-6 Connectors for neuraxial applications (noted as Part 6 throughout this application), for administering medication into the subarachnoid or epidural space comprising a yellow color code. Another implementation disclosed herein is configured to be operable with enteral or ENfit connectors and adapters in the format ISO 80369-3 Connectors for enteral applications (noted as Part 3 throughout this application) for administering nutrition and gasses comprising a purple color code.

Additional implementations of the present invention are configured to be used with other small-bore connectors, fittings and adapters such as, but not limited to, connectors and adapters, both in a Luer-format and non-Luer format, for a single, or combination of two or more medical devices to administer, inject, pump, mix, withdraw or infuse fluids, medication, vaccines, diluent, gasses, nutrition, bone-void filler or the like to or from a patient, and connectors, fittings and adapters for transferring or infusing fluids or gasses to or from a patient through devices or tubes, and more particularly to connectors, fittings and adapters comprising a volume-displacing member, forming a substantially more uniformly-configured low deadspace interior fluid or gaseous flowpath. The volume-displacing member may be configured with a body having a through-passage or aperture with a tapered wall formed as a vent to funnel or remove air or air bubbles from the fluid within the one or more device or apparatus prior to administering the fluid. The volume-displacing member reduces the fluid, gas or air volume retention within the interior cavity of the one or more connector, adapter, fitting or device and may filter, regulate or monitor the fluid or gaseous flow within and through the flowpath of one or more connector, adapter, fitting or device.

One implementation of the present invention comprises a volume-displacing member configured to reduce the amount of medicine or diluent that remains within the flowpath, interior cavity, or deadspace of a luer syringe or male connector nozzle and female luer hub before, during or after the injection or infusion is administered to a patient or transferred to another device, such as a syringe or pump, an infusion line, IV fluid bag, for an IV push, primary IV administration of fluids or a secondary IV administration of fluids. One implementation of the present invention comprises a volume-displacing member, positioned within the combined interior deadspace cavity of a male luer nozzle or female luer hub, configured to reduce the amount of medicine or fluid within the combined interior cavity and includes a body with an interior through-passage with a vent or aperture formed to expel or remove air or air bubbles within the medication or fluid within the interior cavity before the injection or infusion is administered. One implementation of the present invention comprises a volume-displacing member positioned within the combined interior cavity of a male nozzle and female hub female luer hub configured with an inside through-passage completely separate from the distal interior deadspace cavity formed within the female hub. One implementation of the present invention is configured to optimize the volume of medicine or fluid withdrawn from a vial, dispensed into a syringe from a filling apparatus, or added to a prefilled syringe to the prescribed dose, leaving more of the medicine in the vial, filling apparatus or dispenser for subsequent doses.

One implementation of the present invention provides a stop or lip on the volume-displacing member to limit and standardize the depth the syringe nozzle can be positioned within the female hub. Some implementations of the volume-displacing member of the present invention displace a substantial amount of the cubic volumetric capacity, individually or in combination, within the combined interior deadspace cavity of the syringe nozzle and female hub. Additionally, some implementations of the volume-displacing member of the present invention are configured with a flowpath or interior through-passage of a luer-configured apparatus or device, maximizing the delivery of the intended fluid or gas dose.

One implementation of the present invention may also include a closure cap configured to reduce the amount of medicine or fluid in a prefilled syringe. One implementation of the present invention is configured to reduce the amount of medicine or fluid within the fluid path or interior cavity through-passage of a male luer nozzle. One implementation of the present invention is configured to reduce the amount of medicine or fluid within the fluid path or interior cavity of a female luer hub. Additionally, the present invention is configured to reduce the amount of medicine, diluent or gas that remains within a flowpath or interior cavity of one or more luer connectors or adapters having at least two different inside diameters before, during or after an injection, infusion or gas are administered.

One implementation of the present invention comprises a single luer apparatus where a syringe cap includes a volume-displacing member that extends into the interior cavity of the luer nozzle of a prefilled syringe. The volume-displacing, male luer syringe or female luer hub implementation of the present invention can easily be incorporated in existing multi-cavity luer tooling when the conventional cores need to be replaced, simply by upgrading the cores to form the volume-displacing member within a male luer nozzle or female luer hub. Retrofitting the new cores into existing tooling eliminates the need for costly new luer syringe, luer connector or luer hub tooling.

An even more cost-effective and time-saving improvement may be achieved by adding the separate volume-displacing member of the present invention within the individual or combined interior cavity of a female luer hub or male luer nozzle or at the distal end of the nozzle of a luer syringe.

One implementation of the present invention comprises a volume-displacing member, positioned within the interior cavity of a NRfit® device or connector, configured to reduce the amount of anesthetic that remains within the interior cavity, before, during or after the anesthesia is administered to a patient. One implementation of the present invention comprises a volume-displacing member, positioned within the interior cavity of a NRfit® device or connector, configured to form at least one continuous interior seal to lower the risk of a flammable gas anesthesia leak into a surgical setting. One implementation of the present invention comprises a volume-displacing member, positioned within the interior cavity of an ENfit device or connector, configured to reduce the amount of liquid nutrition that remains within the interior cavity, before, during or after the liquid nutrition is administered to a patient. One implementation of the volume displacing member of the present invention having a through-passage with an inside wall with an inside diameter configured to gauge the flowrate of a fluid or gas through the device or apparatus and include color-coded system distinguishing each flowrate parameter.

The use of volume-displacing members as disclosed herein would significantly reduce insulin waste within luer needle/syringes used to inject insulin. The people living with type 2 diabetes worldwide was estimated at 405 million in 2018 and is expected to increase to 510 million in 2030, translating to an increase in the need for the 1,000 IU insulin vials from 516 million vials in 2018 to 633 million vials in 2030. It is possible a 10% reduction of insulin waste could be achieved by the adoption of the luer needle/syringe of the present invention translating to approximately 51,600 liters or 13,631 gallons of insulin per year, based on 516 million vials, that could be utilized and injected, rather than now disposed of and placed in the medical waste stream.

According to some implementations of the present invention an assembly is provided in which a volume displacing member occupies deadspace within one, or between two or more neuraxial syringes, hubs, connectors, fittings, dispensers or adapters per Part 6.

According to some implementations of the present invention an assembly is provided in which a volume displacing member occupies deadspace within one, or between two or more enteral syringes, hubs, connectors, fittings, dispensers, or adapters per Part 3.

According to some implementations of the present invention an assembly is provided in which a volume displacing member occupies deadspace within one, or between two or more intravascular luer syringes, hubs, connectors, fittings, dispensers or adapters per Part 7.

According to some implementations of the present invention a luer apparatus is provided with a flowpath or interior through-passage having an improved laminar-flow regime, without ridges, steps, dead-ends or sharp points, facilitating and optimizing the smooth, orderly movement of fluid or gas, with reduced turbulence, and without lateral mixing, swirls, eddies or subcurrents within the flowpath or interior cavity of one or more luer connectors.

According to some implementations, apparatus are provided that include a female luer hub and male luer syringe, comprising connectors, adapters, fittings or devices having an interior cavity with volume-displacing member, for intravascular use formed with a rigid material having a modulus of elasticity either in flexure or in tension greater than 3,433 MPa to comply with Section 3.7 of Part 7, for neuraxial use formed with a rigid material having a nominal modulus of elasticity either in flexure or in tension greater than 950 MPa complying with Section 4.2 of Part 6, and for enteral use formed with a rigid material having a nominal modulus of elasticity either in flexure or in tension greater than 700 MPa complying with Section 4.2 of Part 3.

These and other objects, features and advantages of the present invention will become evident in view of the following detailed description taken in conjunction with the accompanying drawings.

BRIEF DESCRIPTION OF THE DRAWINGS

FIG. 2C is a cross-sectional side view of the prior art female luer hub of FIGS. 1, 2A and 2B.

FIG. 3A is a cross-sectional side view of one implementation of a low deadspace luer needle/syringe apparatus of the present invention in an assembled configuration.

FIG. 3B is an isometric view of the volume-displacing member of FIG. 3A.

FIG. 3C is a full top view of the volume-displacing member of FIG. 3A with at least one radial protrusion formed on the distal end.

FIG. 3D is a full top view of one implementation of the volume-displacing member with at least one concave recess formed on the distal end.

FIG. 3E is a cross-sectional front view of the low deadspace needle/syringe apparatus of FIG. 3A in axis 3E-3E.

FIG. 3F is a cross-sectional front view of the low deadspace needle/syringe apparatus of FIG. 3A in axis 3F-3F.

FIG. 4A is a cross-sectional side view of one implementation of a low deadspace needle/syringe apparatus having a volume-displacing member positioned within a female luer hub attached to a male luer nozzle.

FIG. 4B is a full top view of the volume-displacing member of FIG. 4A.

FIG. 4C is a cross-sectional front view of the low deadspace luer apparatus of FIG. 4A in axis 4C-4C.

FIG. 5A is a cross-sectional side view of one implementation of a low deadspace luer apparatus having a laminar flowpath configured within the combined interior cavity.

FIG. 5B is a cross-sectional side view of one implementation of a low deadspace luer apparatus with an integrally-formed volume-displacing member joined with a separate volume-displacing member.

FIG. 5C is a full top view of the separate volume-displacing member of FIG. 5B.

FIG. 5D is a cross-sectional side view of the separate volume-displacing member of FIG. 5C having a plurality of inside through-passages.

FIG. 6A is a cross-sectional side view of one implementation of a low deadspace luer apparatus comprising a volume-displacing member mechanically coupled to the female luer hub attached to a male luer nozzle.

FIG. 6B is a cross-sectional side view of the volume-displacing member of FIG. 6A with at least one annular recess formed in the distal end.

FIG. 6C is a cross-sectional side view of one implementation of the volume-displacing member of the present having an elongate body with at least one convex annular ring formed around the outside diameter of the distal outside wall.

FIG. 6D is a cross-sectional front view of the volume-displacing member of FIG. 6A in axis 6D-6D.

FIG. 7A is a cross-sectional side view of one implementation of a method of the assembly process of positioning the volume-displacing member within a female luer hub.

FIG. 7B is a cross-sectional side view of a method of the assembly process of the low deadspace device with a mandrel mechanically securing the volume-displacing member within a female luer hub.

FIG. 7C is a cross-sectional side view of the method of the assembly process of the low deadspace luer apparatus with the volume-displacing member mechanically secured within the female luer hub.

FIG. 8B is an isometric view of the volume-displacing member of FIG. 8A.

FIG. 8C is a cross-sectional side view of one implementation of a volume-displacing member having a proximal end with a reduced outside diameter.

FIG. 8D is a full front view of the volume-displacing member of FIGS. 8A and 8B.

FIG. 8E illustrates one implementation of a two-piece volume-displacing member of the present invention.

FIG. 8F is a cross-sectional front view of the low deadspace apparatus of FIG. 8A in axis 8F-8F.

FIG. 8G is a full side view of one piece of the two-piece volume-displacing of FIG. 8E.

FIG. 9 is a cross-sectional side view of one implementation of a luer nozzle of the present invention having a distally-formed interior cavity with an inside wall with an equal inside diameter.

FIG. 10A is a full top view of one implementation of the singularly formed volume-displacing elongate member of the present invention having an enlarged distal body.

FIG. 10B is a cross-sectional side view of one implementation of the low deadspace luer apparatus in a first, pre-assembled position.

FIG. 10C is a cross-sectional side view of one implementation of the low deadspace luer apparatus in a second, assembled position.

FIG. 10D is a cross-sectional front view of the low deadspace luer apparatus of FIG. 10C in axis 10D-10D.

FIG. 11A is a cross-sectional side view of a low deadspace luer apparatus in a first pre-assembled position.

FIG. 11B is a cross-sectional side view of the low deadspace luer apparatus of FIG. in a second, assembled position.

FIG. 11C is a full side view of the volume-displacing member according to one implementation with an enlarged distal body with an extended proximal portion.

FIG. 12B is a cross-sectional side view of the method of the assembly process using the male nozzle to position the volume displacing member within a female hub.

FIG. 12C is a cross-sectional side view of the method of the assembly process of the low deadspace luer apparatus of FIG. 12B with the male nozzle positioning the volume displacing member within the female hub FIG. 12D is a cross-sectional side view of the assembly process of the low deadspace luer apparatus of FIG. 12C having the volume-displacing member mechanically lock-fit within the interior cavity of a female luer hub.

FIG. 12E is a cross-sectional front view of the low deadspace luer apparatus of FIG. 12C in axis 12E-12E having a plurality of resilient radial portions concentrically compressed as the elongate member is advanced within the female luer hub.

FIG. 12F is a cross-sectional front view of the low deadspace luer apparatus of FIG. 12D in axis 12F-12F having the volume-displacing member inserted in the female luer hub.

FIG. 14A is a cross-sectional side view of one implementation of a low deadspace luer apparatus with a volume-displacing member positioned within the interior cavity of a male luer nozzle and distal interior cavity of a female luer hub attached to a syringe.

FIG. 14B. is a cut-away side view of the volume-displacing member of FIG. 13A.

FIG. 14C is a cross-sectional side view of one implementation of a low deadspace luer apparatus with a volume-displacing member, with at least one distal hook or lip, positioned within the interior cavity of the luer nozzle.

FIG. 14E is a cross-sectional front view of the low deadspace syringe apparatus of FIG. 14A in axis 14E-14E.

FIG. 15A is a cross-sectional side view of one implementation of a low deadspace luer syringe apparatus with a volume-displacing member positioned within the combined interior cavity of a female hub and a syringe nozzle.

FIG. 15B is full top view of the volume-displacing member of FIG. 15A.

FIG. 15C is cross-sectional side view of the volume-displacing member of FIG. 15A.

FIG. 15D is a cross-sectional front view of the low deadspace syringe apparatus of FIG. 15A in axis 15D-15D.

FIG. 18 is a cross-sectional side view of one implementation of a low deadspace prefilled luer syringe with a volume-displacing member positioned within the luer nozzle of the syringe.

FIG. 19 is a cross-sectional side view of one implementation of a low deadspace pre-filled syringe with a syringe cap with a volume-displacing member and a fluid or moisture-sensing, color-changing leak-detecting ring or plate.

FIG. 20A is a cross-sectional side view of one implementation of a smart low deadspace pre-filled, tamper-resistant luer syringe apparatus with a syringe cap with a volume-displacing member and an outside collar with an attached and intact frangible label with a frangible wireless RFID tag.

FIG. 20B is a cross-sectional side view of the smart low deadspace pre-filled luer syringe apparatus of FIG. 20A with a torn outside label on a syringe cap with a RFID tag transmitting a signal the seal has been broken.

FIG. 21A is a cross-sectional side view of a low deadspace luer syringe apparatus with a female hub attached to a luer nozzle with an integrally formed volume-displacing member.

FIG. 21B is a cross-sectional front view of the low deadspace luer syringe apparatus of FIG. 21A in axis 21B-21B.

FIG. 22A is a cross-sectional side view of a low deadspace luer syringe comprising a female hub attached to a syringe nozzle with an integrally formed volume-displacing member positioned between two interior through-passages.

FIG. 22B is a cross-sectional front view of the low deadspace luer syringe apparatus of FIG. 22A in axis 22B-22B comprising a volume-displacing member integrally formed with the inside wall of the luer nozzle by two opposing integrally-formed strips or ribbons.

FIG. 23A is a cross-sectional side view of another implementation of the low deadspace luer syringe of the present invention comprising a female luer hub attached to a syringe nozzle with an integrally formed elongate strip extending the length of the integrally formed volume-displacing member with a distal end with chamfered endwall or face.

FIG. 23B is a cross-sectional front view of the low deadspace luer syringe apparatus of FIG. 23A in axis 23B-23B.

FIG. 24 is a cross-sectional front view of one implementation of a low deadspace luer syringe apparatus comprising a female luer hub attached to a male nozzle with an integrally formed volume-displacing member surrounded by a plurality of through-passages formed by a plurality of integrally formed, elongate strips.

FIG. 25 is a cross-sectional side view of the method of the assembly process of one implementation of the present invention illustrating a cross-sectional side view of a low deadspace syringe shown in a first, pre-assembled position FIG. 26 is a cross-sectional side view of the method of the assembly process of one implementation of the present invention of a low deadspace syringe shown in a second, assembled position with the volume-displacing member lock-fit within the luer nozzle.

FIG. 27 is a cross-sectional side view of one implementation of a low deadspace syringe of the present invention in a ready-to-use state.

FIG. 30 is a cross-sectional side view of the prior art luer lock connector apparatus in the neuraxial or NRfit® configuration or Part 6 of the ISO Standard having a first male connector and a second female connector in a first, separated position.

FIG. 31A is a cross-sectional side view of a low deadspace luer lock NRfit® connector apparatus of the present invention, having a first male connector with a first interior cavity joined to a second female connector with a second interior cavity forming a combined interior cavity and a volume-displacing member positioned within the combined cavity.

FIG. 31B is a cross-sectional side view of the low deadspace NRfit® volume-displacing member of the present invention having a body with a proximal end and a distal end having differing outside diameters, and a medial body having a larger outside diameter.

FIG. 31C is a cross-sectional front view of the volume-displacing member of FIG. 31A in axis 31C-31C.

FIG. 31D is a cross-sectional front view of the volume-displacing member of FIG. 31A in axis 31D-31D.

FIG. 32 is a cross-sectional side view of one implementation of the low deadspace NRfit® apparatus of the present invention with a male luer nozzle attached to a female luer hub with an interior cavity with integrally-formed volume-displacing member, having an inside through-passage, positioned within the interior cavity of the male luer nozzle.

FIG. 33 is a cross-sectional side view of the prior art luer lock connector apparatus of the present invention in the enteral or ENfit configuration or Part 3 of the ISO Standard having a first male connector and a second female connector shown in a first, separated position.

FIG. 34A is a cross-sectional side view of the low deadspace ENfit luer lock connector apparatus of the present invention, having a first male connector with a first interior cavity joined to a second female connector forming a combined interior cavity and a volume-displacing member positioned within the combined cavity.

FIG. 34B is a cross-sectional front view of the volume-displacing member of FIG. 34A in axis 34A-34A.

FIG. 35A is a cross-sectional side view of the ENfit volume-displacing member of the present invention having an enlarged medial body formed between an elongated proximal body and an elongated distal body with opposing through-passages formed along the outside wall.

FIG. 35B is a cross-sectional front view of the volume-displacing elongate member of FIG. 35A in axis 35B-35B.

FIG. 36A is a cross-sectional top view of the ENfit volume-displacing member of the present invention having with an enlarged medial body formed between a proximal end and a distal end, with at least one through-passage formed in the outside wall of the body.

FIG. 36B is a cross-sectional front view of the volume-displacing member of FIG. 36A in axis 36B-36B comprising a body with opposing through-passages formed along the outside wall and through the medial portion.

FIG. 37A is a cross-sectional side view of a low deadspace male luer-to-male luer adapter connector of the present invention connecting a first syringe with a second syringe.

FIG. 37B is a cross-sectional front view of the low deadspace male luer-to-male luer adapter of FIG. 40 in axis in axis 37B-37B.

FIG. 37C is a cross-sectional front view of the low deadspace male luer-to-male luer adapter of FIG. 37A in axis 37C-37C.

FIG. 38A is a cross-sectional side view of a male luer syringe attached to a low deadspace fill needle of the present invention having a female luer hub, with a distal blunt-tipped needle configured with an integrally-formed volume-displacing member positioned within the interior cavity.

FIG. 38B is a cross-sectional front view of the low deadspace formed fill needle of FIG. 38A in axis 38B-38B.

DETAILED DESCRIPTION OF THE DRAWINGS

A number of low deadspace syringes and small-bore devices are disclosed herein. In the following description, numerous specific details are set forth in order to provide a thorough understanding of the present invention. However, it will be obvious to one of ordinary skill in the art that the invention may be practiced without these specific details. In other instances, well-known structures and processing steps have not been shown in particular detail in order to avoid unnecessarily obscuring the present invention. Additionally, it should be noted that the invention is applicable to a variety of intravascular, enteral feeding, neuraxial or breathing systems, such as connectors, adapters, fittings, in-line infusion valves, hubs, a needle with a sharpened distal tip, a needle with curved distal tip, a Huber needle, any hollow-bore needle with a distal tip, a needle having a blunt tip used as a fill needle or to access a infusion port, a pipette used in research, a needleless valve, a vial adapter, a stopcock, a syringe adapter, spike port adapter or an infusion line used to administer or withdraw fluid, gasses and medicine to or from a patient. Any implementation of volume-displacing member in this application may be formed singularly or separately, and be combined by a number of methods, including but not limited to injection molding, a folding clam-shell configuration, stamping, progressive-dye fabrication, extruding, ultrasonic welding, adhesive bonding, interference fit, press fit, friction fit, compression fit, heat welding, a threaded means or the like. It is appreciated, however, that the present invention is not limited to these devices.

It is understood that the low deadspace syringes and small-bore devices disclosed herein in regard to syringes and female hubs can easily be adapted to all types of other devices where a needle, connector, adapter, infusion line or fitting may be used, including, but not limited to injection needles, infusion sets, anesthesia, nutritional feeding and to flush infusion lines.

Figure 1:
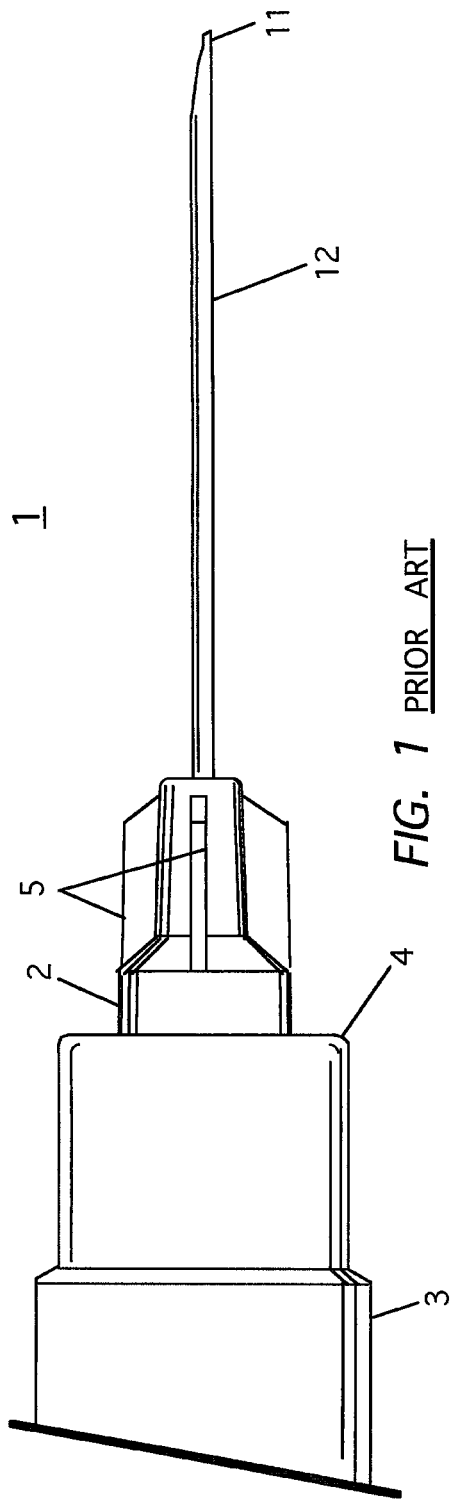
FIG. 1 is a full side view of an example of a prior art luer-lock syringe/needle apparatus joined by luer connectors.
Figure 2B:
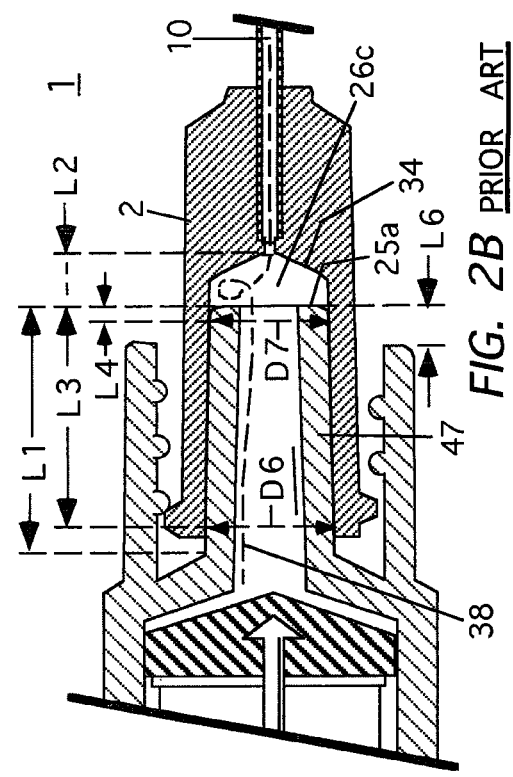
FIG. 2B is a cross-sectional side view of the prior art syringe/needle apparatus of FIG. 2A.

FIGS. 1-2B illustrate a conventional, luer needle/syringe combination 1 that is the most widely used syringe configuration worldwide due to the broad range of uses (injections, infusions, flushes, and the like), interoperability and connectivity to numerous luer connectors, fittings, adapters and devices, ease of filling with any variety of medicine, vaccine, therapeutic, fluid or gas, is relatively inexpensive in cost and ease of mass-manufacture with significant existing production lines in place throughout the world. Two luer configurations are shown, a luer-lock configuration shown in FIGS. 1-2B and other drawings in this application, and a luer-slip configuration, shown in FIGS. 3A and 4A and other drawings in this application.

FIG. 1 illustrates a full side view of a prior art luer lock syringe/needle apparatus 1 comprising a hollow, elongate needle 12 having a sharpened distal tip 11 attached to a female luer hub 2 rotated onto to a distal luer-lock collar 4 of the syringe 3, with a needle hub 2 having at least one elongate rib 5 formed to engage a scabbard to facilitate rotational attachment or removal of the hub 2 from the syringe 3.

Figure 2A:
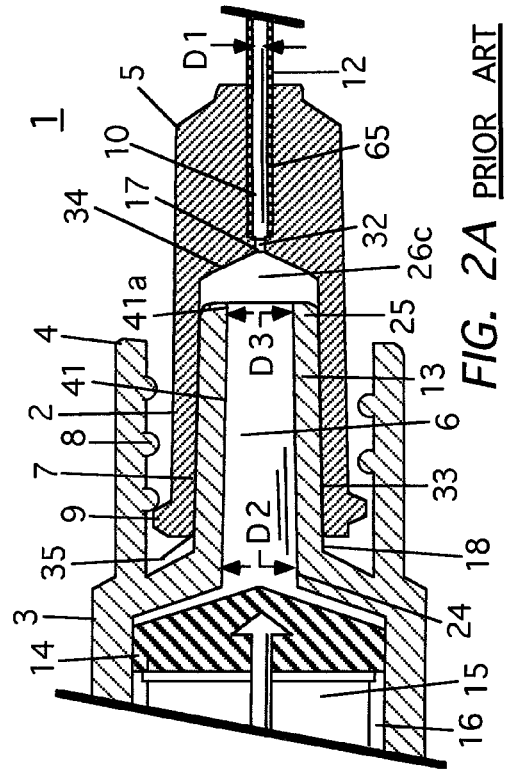
FIG. 2A is a cross-sectional side view of the prior art luer-lock apparatus of FIG. 1 having a combined interior deadspace cavity.

FIG. 2A comprises a cross-sectional side view of the prior art luer needle/syringe apparatus 1 of FIG. 1 comprising a luer-lock syringe 3, having a hollow barrel cavity 16 and a male luer nozzle 13 with a first interior cavity 6, positioned within the interior cavity 26 of a female luer hub 2, as shown in FIG. 2C, with an attached elongate needle 12. The elongate needle 12 has a distal sharpened end 11 and a hollow lumen 10 having a first inside diameter parameter D1, that varies depending on the needle gauge, attached within the distal lumen 65 of a female hub 2. The female hub 2 comprises an inside sidewall 7 with a 6% nominal frustoconical taper defining the interior cavity 26 with an open proximal end 35 and a second distal interior cavity 26c, formed by an endwall 34, in communication with a concentrically-centered opening or aperture 32 formed within a stop or lip 17 for positioning the proximal end of the needle in the distal lumen 65. The mass-manufactured syringe body, male connectors and female hubs are translucent in practice in order to observe and allow any air or air bubbles to be removed from the fluid or medicine prior to delivery to a patient, port or infusion line. The female hub 2 includes at least one proximal flange or lug 9 to mechanically engage the inside locking threads 8 of the distal luer-lock collar 4 by rotating the female hub 2 onto the nozzle 13. The female hub 2 may include a threaded portion rather than the lug 9 to secure the hub 2 to a luer-lock syringe 3 or a male luer connector having a port, port adapter, needleless valve, intravenous tubing connector, intravenous fluid bag or the like.

The hollow barrel cavity 16 must be filled with medication from a vial, or an automated syringe filler where the needle 12 is attached after the syringe barrel cavity 16 is filled. When a vial is used, air is drawn into the syringe barrel cavity by moving the plunger rod 15 and piston 14 away from the needle by the approximate amount of the desired dose, then the air is injected through the needle into the vial to create a positive pressure to displace the fluid as the desired dose is drawn from the vial through the needle into the syringe barrel cavity. The elastomeric piston 14, forms an annular seal with the inside barrel wall and is selectively slidable within the barrel cavity 16. The syringe nozzle 13 has a frustoconically tapered outside sidewall 18 and an inside sidewall 41 with distal opening 41*a* defining the interior cavity 6 formed from the open proximal end 24 terminating at the distal end 25 having an endwall or face 25*a*. The interior cavity 6 may be tubularly-configured with an inside wall having an equal inside diameter along its length or may include an inside sidewall having a variably-tapering inside diameter shown herein. The open proximal end 24 of the interior cavity 6 has an inside sidewall 41 formed with a second inside diameter parameter D2, measuring between a minimum of 2.9 mm or 0.114 inches per Part 7 and an assumed maximum of 3.68 mm or 0.145 inches in practice. The distal opening of the syringe nozzle is formed with a third inside diameter parameter D3, measuring a between a minimum of 1.14 mm or 0.045 inches in practice to a maximum of 2.9 mm or 0.114 inches per Part 7. The syringe nozzle 13, as is used in clinical practice and shown through this application, is configured with a substantially equal wall thickness 47, as shown in FIG. 2B, to avoid curing shrinkage or deformation issues during the injection molding process and ensure an air and liquid-tight seal 33 is formed between the conical mating surface of the outside frustoconical sidewall 18 of the male nozzle 13 and the inside frustoconical sidewall 7 of the female hub 2 when the connectors and adapters are joined together.

In ISO 7886-1:2017, the requirements and test methods are specified for verifying the design of empty sterile single-use hypodermic syringes, with or without needle, made of plastic or other materials and intended for the aspiration and injection of fluids after filling by the end-users. The maximum deadspace allowed within the inside cavity of the luer nozzle under ISO 7886-1:2017 is as follows: 1 ml-3 ml syringe=0.07 ml; 5 ml syringe=0.075 ml; and 10 ml syringe=0.10 ml. The present invention is configured to significantly reduce the allowed deadspace within the inside cavity of the luer syringe nozzle, allowing additional doses to be harvested and administered from a multidose vial.

The flowrate between the female connectors and male connectors per Table D.1 per Part 7 ranges from 0 ml/minute to 1,200 ml/minute for syringes, needles, IV tubing sets, retention mechanisms, IV catheters, IV catheter ports, stopcocks, adaptors and medication compounding adapters.

FIG. 2B illustrates a cross-sectional side view of the prior art luer-lock needle/syringe apparatus of FIG. 2A comprising a luer syringe 3 having a male nozzle 13, with an interior cavity 6 forming a first deadspace, positioned within the interior cavity 26 of the female hub 2, as shown in FIG. 2C. A distal interior cavity 26*c* is now formed between the inside endwall 34 of the female hub 2 and outside endwall 25*a* of the syringe nozzle 13, forming second deadspace where air or air bubbles within the fluid can stall or linger and tend to attach to the inside walls formed along the flowpath when the syringe 3 is filled with fluid. Any air or air bubbles attached to the inside walls or that linger within the distal interior cavity may subsequently release into the fluid being injected, flushed or infused into a patient. A circuitous or varying through-passage flowpath 38, shown in a broken line, is formed between the syringe barrel cavity 16, the interior cavity 6 of the male nozzle 13, swirling within interior cavity 26*c* and advancing through the aperture 32 and into the needle lumen 110.

The distal end 25 of the nozzle 13 is configured with an outside wall 18 with an outside diameter parameter D7, measuring between a minimum of 3.97 mm and maximum of 4.035 mm or between 0.156 inches and 0.159 inches for rigid material, and between a minimum of 3.97 mm and maximum of 4.072 mm or between 0.156 inches and 0.160 inches for semi-rigid material, at the position L4 where the male taper of outside diameter of tip of nozzle 13 measures 0.75 mm or 0.0295 inches (basic dimension) from distal endwall 25*a* of the tip of the nozzle 13, per Part 7.

The tapered outside wall 18 of the proximal end 24 of the syringe nozzle 13 is configured with an outside diameter parameter D6 measuring between a minimum of 4.375 mm and maximum of 4.440 mm or between 0.172 inches and 0.1748 inches for rigid material, and between a minimum of 4.375 mm and maximum of 4.447 mm or between 0.172 inches and 0.1762 inches for semi-rigid material, at the position L3 where the outside diameter measures 7.5 mm or 0.295 inches (basic dimension) from the distal endwall 25*a* per Part 7. The projection of the nozzle 13 is configured with a length of L6, measuring a minimum of 2.1 mm or 0.083 inches from the distal end of the thread collar 4 to the distal endwall 25 per Part 7.

FIG. 2C is a cross-sectional side view of the prior art female luer hub of FIGS. 2A and 2B having a distal interior cavity 26*c*, as shown in FIG. 2B, with an inside sidewall 7 having fourth distal inside diameter parameter D4, measuring between a minimum of 3.820 mm and maximum of 0.3.865 mm or 0.150 inches and 0.152 for rigid material, and between a minimum of 3.793 mm and maximum of 0.3.893 or 0.149 inches and 0.153 for semi-rigid material, at the position L5 where the inside diameter of the hub 2 measures 7.5 mm or 0.295 (basic dimension) from proximal open end 35.

The open proximal end 35 of the interior cavity 26 has a fifth inside diameter parameter D5, measuring between a minimum of 4.225 mm and a maximum of 4.270 mm or between 0.166 inches and 0.168 inches for rigid material, and measuring between a minimum of 4.198 mm and maximum of 4.298 mm or 0.165 inches and 0.169 inches for semi-rigid material, at the position L4, where the inside diameter of the female taper measures 0.75 mm or 0.0295 inches (basic dimension) from the open proximal end 35 per Part 7.

The interior cubic volume of the distal interior cavity 26 of the female hub 2 varies in volume depending on each manufacturer's interior configuration and how tightly needle hub 2 is secured to the nozzle 13 of the syringe 3 and how accurately the parts are injection molded. Although the medication or fluid remaining in the prior art interior cavity 6 of a luer nozzle and interior cavity 26 of luer needle hub 2 may seem small, in aggregate terms the adoption of the low deadspace luer device or apparatus of the present invention will allow fillable luer syringes, prefilled luer syringes, single and multi-dose vials of medicine to be more accurately filled without including additional fluid volume to accommodate for the varying interior cavity configurations forming a deadspace in the current luer devices. Additionally, the fluid or medicine retained within the deadspace of the prior art luer device, connector or apparatus is disposed into the medical waste stream, requiring additional energy to evaporate the fluid before combustion occurs during incineration.

FIGS. 3A-3F illustrate a syringe apparatus 101 of the low deadspace syringe/needle apparatus 101 of the present invention in a ready-to-use state with a male luer-slip syringe 3b joined to a female luer needle hub 102 that has separate singularly-formed, volume-displacing member 120 positioned within the combined interior cavity of the apparatus. The volume-displacing member 120 has an elongate body 122 with an outside wall 137 with an outside diameter D8, as shown in FIG. 3B, that is smaller than the inside diameter D3 of the distal aperture 41a of the syringe nozzle 13 as shown in FIG. 2A. The volume-displacing member 120 has a closed proximal end 130 and an inside through passage 121 originating in the outside wall 137 and terminating at the open distal endwall 144. In use, a flowpath 138, shown in a broken line, is formed between the syringe barrel cavity 16, the inside sidewall 41 of the male nozzle 13, the outside wall 137 and inside through-passage 121 of the volume-displacing member 120 and the distal interior cavity 126c of the female hub 102 and the needle lumen 110. The volume-displacing member 120 is configured to reduce the interior cubic volumetric capacity within the combined interior cavity and the interior through-passage is configured to vent or remove air or air bubbles from fluid within the combined interior cavity. The implementations of the volume-displacing member, or the male or female small-bore connecters of the present invention throughout this application may be formed with a rigid material produced from metal, medical-grade plastic resin, including but not limited to polycarbonate or a blend of resins, or from a semi-rigid or resilient material produced from a medical-grade plastic resin, including but not limited to polypropylene, silicone, polyurethane, polyethylene, polyesters or a blend of resins that may provide a superior sealing interface between the components. As an example, polypropylene is a self-lubricating plastic resin with a low coefficient of friction and hydrophobic properties.

The luer-lock syringes, luer-slip syringes, loss of resistance luer syringes, luer flush syringes or luer syringes having a resilient, blo-fill, collapsible barrel or reservoir used in clinical practice or shown throughout this application are interchangeable with each other, and with the hubs, needles, connectors, adapters and fittings disclosed herein. The volume-displacing member of the present invention may be formed within, or added to a syringe configured with a resilient, blo-fill, collapsible barrel or reservoir, or a prefilled syringe, small-bore connector, infusion line, adapter or fitting, and the female hub of the present invention may be configured with a needle, fill needle, tube, adapter, connector or the like.

FIGS. 3A-3F illustrate other implementations of a volume-displacing member 120. In the example of FIG. 3A, the volume-displacing member 120 is shown being a part of a needle/syringe apparatus 101.

According to one implementation of the present invention, FIG. 3A illustrates a cross-sectional side view of the low deadspace luer syringe/needle apparatus 101 in a ready-to-use state comprising a volume-displacing member 120 positioned within the interior cavity 106 of a male nozzle 13. The volume-displacing member 120 has an outside wall 137 with an outside diameter D8, as shown in FIG. 3B, measuring less than the inside diameter D3 of the distal opening 41a of the syringe nozzle 13 as shown in FIG. 2A. The female hub 102 includes an attached elongate needle 112 with a hollow lumen 110 having an inside diameter D1, and a sharpened distal tip 111. The female hub 102 is joined with the male nozzle 13 of the luer-slip syringe 3b that includes a plunger rod 15 and piston 14 shown in a deployable position and is moveable within the syringe barrel cavity 16 to fill or empty the syringe 3b. The volume-displacing member 120 comprises an elongate body 122, with a closed proximal end 130 and an inside through-passage 121, separating a first resilient distal end 131a and a second resilient distal end 131b, terminating at the distal endwall or face 144a and 144b respectively, as shown in FIG. 3B. The resilient distal ends are mechanically secured by a press or compression-fit into a distal nest 145 formed within the interior cavity of the female hub. A flowpath 138, shown in a broken line, is formed within the combined interior cavity that includes the interior cavity 126c of the female hub 102 and is configured to move fluid and air into the aperture 132 and lumen 110 of the needle when the plunger 15 and piston 14 are advanced toward the needle 112.

When the syringe 3b is mated with the female hub 102, the outside wall 18 of the luer nozzle 13 forms a liquid-tight and air-tight seal 133 with the inside sidewall 107 of the female hub 102. A reduced volume or amount of medication remains within the interior cavity of luer nozzle after fluid within syringe is dispensed through the needle. When a needle hub is attached to a conventional luer syringe, the volume-displacing member of the present invention displaces a majority of cubic volumetric fluid and minimizes the deadspace within the interior cavity of luer nozzle. The syringes illustrated with the present invention may comprise a multi-chamber syringe or multi-barrel syringe. The closed, solid proximal end of volume-displacing member of the present invention may be formed in a number of ways to conform, co-operate and form a seal with distal end of syringe piston when syringe plunger is advanced to distal end of syringe barrel cavity to expel fluid or medicine from any syringe described and disclosed in this application.

The outside wall of the distal end of volume-displacing member of the present invention may be joined to the inside wall of a distal nest of a female hub by a number of processes or methods, including but not limited to ultrasonic welding, adhesive bonding, interference-fit, press-fit, friction-fit, compression-fit, heat-welding, an interlocking interface, threads or the like.

The implementations of volume-displacing member of the present invention may be fabricated or configured comprising any number of shapes, including but not limited to elongated, annular, radial, geometric, multi-sided, tubular, reducing or expanding and may include at least one through-passage or side-passage, forming at least one liquid or gaseous flowpath or interior through-passage with or within at least one luer connector, adapter or fitting, configured to vent air or air bubbles from liquid or gas within the luer connector or connectors before use, and reduce the cubic volume within an interior cavity of a small-bore connector or combined cavities of small-bore connectors before, during or after use.

FIG. 3B is an isometric view of a volume-displacing member 120 of FIG. 3A comprising an elongate body 122 with outside wall 137 having outside diameter D8, with closed proximal end 130 at least one through-passage 121, originating in outside wall 137 and terminating at the distal endwalls 144a and 144b, with the through-passage 121 separating a first resilient distal end 131a and a second resilient distal end 131b.

FIG. 3C is a full side view of the volume-displacing member 120 of FIG. 3A having an elongate body 122 with a first arcuate convex or geometrically-configured protrusion 158a formed around the periphery of first radially-configured resilient distal end 131a, and second arcuate convex or geometrically-configured protrusion 158b formed around the periphery of second radially-configured resilient distal end 131b formed to mechanically secure and mate the volume-displacing member 120 within a female luer hub that includes a nest with an inside wall with a concave recess not shown in this application. The protrusions 158a and 158b form a lip configured to engage the distal end 552 of a mandrel 550, as shown in FIG. 7B, to assist with the assembly of the volume-displacing member 120 into a female luer hub 102.

FIG. 3D is a full side view of one implementation of the volume-displacing member 120a having elongate body 122a with a first concave recess 146a formed around the periphery of first radially-configured resilient distal end 131a and a second concave recess 146b formed around the periphery of second radially-configured resilient distal end 131b. The concave recesses 146a and 146b are configured to mate with a convex annular ring 158d formed in the inside wall 141d of the distal nest 145d of the female hub 102d as shown in FIG. 7C.

FIG. 3E is a cross-sectional front view of the low deadspace luer syringe/needle apparatus 101 of FIG. 3A. in axis 3E-3E illustrating a luer nozzle 13 attached to a needle hub 102, with the volume-displacing member 120 positioned within and reducing the cubic volumetric capacity of the inside cavity 106 of the syringe nozzle 13. A portion of the flowpath 138 is formed between the inside sidewall 41 of the male nozzle 13 and the outside wall 137 of the volume-displacing member 120, allowing the movement of air and fluid between the syringe barrel cavity 16 and needle lumen 110 when the plunger rod 15 and piston 14 are moved in the syringe 3b as shown in FIG. 3A.

FIG. 3F is a cross-sectional front view of the luer syringe apparatus of FIG. 3A in axis 3F-3F having the volume-displacing member positioned within, and reducing the cubic volumetric capacity of the inside cavity 106 of the syringe nozzle 13. A portion of the flowpath 138 is formed between the inside through-passage 121 of the volume-displacing member 120 and the interior cavity 106 of the male nozzle 13 allowing the movement of air and fluid between the syringe barrel cavity 16 and needle lumen 110 when the plunger rod 15 and piston 14 are moved in the syringe 3b as shown in FIG. 3A.

FIGS. 4A-4C illustrate other implementations of the volume displacing member 120b.

FIG. 4A is a cross-sectional side view of one implementation of the low deadspace needle/luer-slip syringe apparatus 101A of the present invention having singularly-formed volume-displacing member 120b, having a first distal end 131a and a second distal end 131b, as shown in FIG. 4B, securely positioned within a female hub 102a with an interior distal nest 145a with inside sidewall 141a with an inside diameter that is configured to form a press or compression-fit with the outside arcuate walls 137a and 137b of the distal ends 131a and 131b as shown in FIG. 4B. The volume-displacing member 120b is configured with an elongate body 122b and a closed proximal end 130b, with opposing inside through-passages 121b and 121d converging with through-passage 121a terminating in a distal endwalls 144a and 144b, as shown in FIG. 4B. The first inside through-passage 121b and second opposing inside through-passage 121d are separated by at least one appendage 160 with opposing inside walls 169 and 169d. A flowpath 138a, shown in a broken line, is formed from the syringe barrel cavity 16 through interior cavity 106 of luer nozzle 13, continuing to through-passages 121b, 121d and 121a of volume-displacing member 120b, and interior cavity 126c and aperture 132 of the female hub 102a, and lumen 110 the needle 112, configured to vent air or gas 115 from the fluid 116 and reduce the inside cubic volumetric capacity within apparatus 101A when the plunger rod 15 and piston 14 are advanced toward the distal end of the syringe 3b. The tapered inside wall 134b of distal nest 145a is configured to funnel fluid 116 and air 115 from through-passage 121a into the aperture 132 and needle lumen 110.

FIG. 4B is a full top view of the volume-displacing member 120b of FIG. 4A having elongated body 122b, with outside walls 137a and 137b may be configured with an outside diameter ≥D3 at distal ends 131a and 131b to form a press or compression-fit when located within the distal opening 41a of the male nozzle 13, as shown in FIG. 4A. The outside walls 137a and 137b at the proximal closed end 130b may be configured with an outside diameter <D3 to facilitate placement of the elongate body 122b within the distal opening 41a of the male nozzle 13. A radiused or chamfered outside corner may be formed on the proximal end of the volume-displacing member of the implementations of the present invention to facilitate the assembly within a luer nozzle.

FIG. 4C is a cross-sectional front view of the low deadspace needle/syringe apparatus 101A of FIG. 4A in axis 4C-4C having the volume-displacing member 120b positioned within the interior cavity 106 of the male nozzle 13 concentrically positioned within the distal interior cavity 126c of the female hub 102a. The first inside through-passage 121b and second inside through-passage 121d form a portion of the flowpath 138a, as shown in FIG. 4A, within the interior cavity 106 of the syringe nozzle 13. The outside walls 137a and 137b of distal ends 131a and 131b, as shown in FIG. 4B, also form a first radial interface 23a and a second radial interface 23b with the inside sidewall 41 at the distal opening 41a configured with an inside diameter D3 of the male nozzle 13.

FIGS. 5A and 5B illustrate luer apparatus 101B and 101C of the low deadspace syringe or small-bore connectors of the present invention with a male luer nozzle attached to a female luer hub with an interior cavity with an integrally-formed volume displacing member positioned within the distal opening 41a of the male nozzle 13.

According to one implementation of the present invention, FIG. 5A. is a cross-sectional side view of the low deadspace luer apparatus 101B with joined small-bore connectors comprising a male luer nozzle 13 attached to a female luer hub 102b with a with a needle 112 attached to the distal lumen 165 and an opposing integrally-formed volume-displacing member 120c with body 122c formed within the distal interior cavity 126c. The body 122c of the volume-displacing member 120c is formed with an outside wall 137c and an open proximal end 130c with a tapered inside wall 117 defining an interior cavity 121c that is in communication with a concentrically-centered through-passage or bore 121e and lumen 110 of the needle 112. The outside wall 137c has an outside diameter that forms a liquid and air-tight seal 123 with the inside diameter D3 of the distal aperture or opening 41*a* of the male nozzle 13. The low deadspace luer apparatus 101B comprises a combined interior cavity with a streamline or laminar flowpath 138*b*, shown in a broken line, formed between the syringe barrel cavity 16 the interior cavity 106 of the luer nozzle 13 the interior cavity 121*c* and through-passage 121*e* of the female hub 102*b* continuing into the lumen 110 of the needle 112, is configured move air or air bubbles and fluid into or out of the apparatus 101B. The tapered inside wall 117 of interior cavity 121*c* is configured as a vent to funnel air or air bubbles and fluid out of the apparatus 101B. The volume-displacing member 120*c* is configured to reduce both the inside cubic volumetric capacity within the combined interior cavity and the fluid or gas remaining within in the flowpath 138*b* after use. The flowpath 138*b* is separated from and bypasses the distal interior deadspace cavity 126*c* formed between the distal end 25 of the luer nozzle 13 and distal endwall 134*c* of female hub 102*b*. A tube or the like, rather than the needle 112, can be assembled within the lumen 165 of the female hub 102*b* prior to packaging, sterilization and use.

A common or combined interior cavity with a forwardly-configured flowpath is formed within the one or more small-bore device, devices, connector or connectors of the present invention and is preferably formed between the hollow barrel cavity of a syringe or hollow tubing, the interior cavity of the male nozzle, the at least one inside through-passage of the volume-displacing member and aperture of the needle hub, continuing into the lumen of a needle or hollow tubing or other component that can be attached within the distal lumen of the female hub configured as a vent to funnel and remove air or air bubbles and the fluid within the combined interior cavity.

According to one implementation of the present invention, FIG. 5B is a cross-sectional side view of a two-piece volume-displacing member located within the low deadspace luer apparatus 101C comprising a male luer nozzle 13 attached to a female luer hub 102*c* having a first integrally-formed volume-displacing member 120*d* joined with a second separate volume-displacing member 120*e*. The first volume-displacing member 120*d* includes an interior cavity 121*c* with a tapering endwall 117*a* formed within a proximal male nozzle 145*b* with an outside wall 145*c* formed within the distal interior cavity 126*c*, attached to a second, separate volume-displacing member 120*e* having distal female collar 131*e* with an inside wall 139*e* defining a nest 121*f*, as shown in FIGS. 5C and 5D, configured with an inside diameter D9 configured to form a press-fit or compression-fit with the outside diameter of the outside wall 145*c* of the male nozzle 145*b* forming a first liquid and air-tight seal 143*c*. The attachment of the female collar 131*e* to the male nozzle 145*b* may also comprise an ultrasonic weld, adhesive bond, interference fit, friction fit, heat weld, matching threads or the like. The outside wall 137*d* of the volume-displacing member 120*d* has an outside diameter that forms a liquid and air-tight seal 123*a* with the inside diameter D3 of the distal aperture 41*a* of the male nozzle 13, isolating the streamline flowpath 138*c*, shown in a broken line, from the distal interior deadspace cavity 126*c* of the female hub 102*c*. The outside wall 137*e* of the volume-displacing member 120*e*, as shown in FIG. 5C, has an outside diameter that forms a second liquid and air-tight seal 123*b* with the inside diameter of the distal aperture 41*a* of the male nozzle 13. A streamline or laminar flowpath 138*c*, shown in a broken line, formed between the syringe barrel cavity 16 the interior cavity 106 of the luer nozzle 13 the interior cavities 121*b* and 121*d*, as shown in FIG. 5D, of the volume-displacing member 102*e* and the interior cavity 121*c* and through-passage 121*e* of the female hub 102*c* continuing into the needle lumen 110, is configured to move air or air bubbles and fluid into or out of the apparatus 101C. The tapered inside wall 117*a* of interior cavity 121*c* is configured as a vent to funnel air or air bubbles and fluid out of the apparatus 101C. The volume-displacing member 120*e* is configured to reduce both the inside cubic volumetric capacity within the combined interior cavity and the fluid or gas remaining within in the flowpath 138*c* after use.

When the volume-displacing member 120*d* and volume-displacing member 120*e* are joined together, the opposing tapered distal inside walls 117*c* and 117*d*, as shown in FIG. 5D, are configured to funnel fluid and air from the interior cavity 106 of the syringe nozzle 13 into the opposing through-passages 121*b* and 121*d* into the interior cavity 121*c* and through-passage 121*e* and into the needle lumen 110, or lumen of tube attached to the female hub 102*c*. The volume-displacing member 120*e* is configured with tapered inside walls 117*c* and 117*d* and at least one inside appendage 160*e* formed by opposing inside walls 169*c* and 169*d* defining the opposing inside through-passages 121*b* and 121*d*.

FIG. 5C is a full top view of the volume-displacing member 120*e* of FIG. 5B having an elongate body 122*e* with an outside wall 137*e* with at least one medial inside through-passage or opening 121*b* and a distal collar 131*e* with a distal endwall 144*e*.

FIG. 5D is a cross-sectional side view of the volume-displacing member 120*e* of FIG. 5B and having an elongate body 122*e* with an outside wall 137*e*, as shown in FIG. 5C, with opposing distal tapered inside walls 117*c* and 117*d* and at least one inside appendage 160*e*, as shown in FIG. 5B, formed by opposing inside walls 169*c* and 169*d* defining two opposing medial inside through-passages 121*b* and 121*d* converging into an open distal nest 121*f* formed within a distal female collar 131*e*, as shown in FIG. 5C, by an inside wall 139*e* with an inside diameter D9.

FIGS. 6A-6D illustrate the luer apparatus 101D of one implementation of the low deadspace luer syringe of the present invention with a singularly-formed, separate volume-displacing member 120*f*, mechanically positioned within the interior cavity 126*c* of a female luer hub 102*d*.

FIG. 6A. is a cross-sectional side view of one implementation of the low deadspace luer apparatus 101D of the present invention with a singularly-formed, separate volume-displacing member 120*f*, positioned within the interior cavity 126*c* of a female luer hub 102*d* and interior cavity 106 of a male luer nozzle 13. The female luer hub 102*d* includes an inside wall 141*d* with annular ring 158*d* having convex profile forming a distal nest distal 145*d* and an attached needle 112 with a lumen 110. The volume-displacing member 120*f* comprises a singularly-formed elongate body 122*f* configured with an outside wall 137*f*, a closed proximal end 130*f* and a distal end 131*f*, as shown in FIG. 6B, and opposing through-passages 121*b* and 121*d*, originating in the outside wall 137*f* converging with a concentrically centered distal through-passage 121*e* terminating in the distal endwall 144*f*, as shown in FIG. 6B. The outside wall 137*f* of the body 122*f* has an outside diameter configured to form a first liquid air-tight seal 123*c* with the distal opening 41*a* with an inside diameter D3 of the male luer nozzle 13, and second liquid and air-tight seal 143*f* is formed by the outside wall 137*f* of the distal end 131*f* with the inside wall 141*d* of the distal nest 145*d* of the female luer hub 102*d*. The inside diameter of the nest 145*d* may be formed with an inside diameter that is larger or smaller than the inside diameter D3 of the male nozzle 13, and may form a liquid and air-tight seal with a substantially matching outside diameter of the outside wall 137f of the distal end 131f of the volume-displacing member 120f.

The volume-displacing member 120f comprises at least one concave recess 146d formed within and around the distal outside wall 137f, as shown in FIG. 6B, configured to form a lock-fit and mate with the annular concave protrusion or ring 158d formed in the distal nest 145d of the female hub 102d. A smooth or laminar flowpath 138d, shown in a broken line, formed between the syringe barrel cavity 16, the interior cavity 106 of the male nozzle 13 and through-passages of 121b, 121d and 121e of the volume-displacing member 120f and the aperture 132 of the needle hub 102d and lumen 110 of the needle 112, is configured move air or air bubbles and fluid into or out of the apparatus 101D. The tapered inside walls 117c and 117d of interior cavity 121c are configured as a vent to funnel air or air bubbles and fluid out of the apparatus 101D. The volume-displacing member 120f is configured to reduce both the inside cubic volumetric capacity within the combined interior cavity and the fluid or gas remaining within in the flowpath 138d after use. The flowpath 138d is separated from and bypasses the distal interior deadspace cavity 126c formed within female hub 102d.

FIG. 6B. is a cross-sectional side view of one implementation of the volume-displacing member of FIG. 6A. with an elongate body 122f and a first inside through-passage 121b and second opposing through-passage 121d, as shown in FIG. 6A, separated by at least one inside appendage 160f with opposing sidewalls 169b and 169b, converging with an axial through-passage 121e terminating in the distal endwall 144f. The body 122f includes two opposing tapered inside walls 117c and 117d, defining the distal end of the inside through-passages 121b and 121d formed between outside wall 137f and axial through-passage 121e.

FIG. 6C is a cross-sectional side view of the volume-displacing member 120g of the present having elongate body 122g with a distal endwall 144g and at least one annular one annular ring 158e with a convex profile formed around distal outside wall 137e. The at least one annular ring 158e of volume-displacing member 120g is configured to mate with an annular convex recess formed within the nest of a female hub, not shown in this application, forming a mechanical coupling between the volume-displacing member 120g and a female hub.

FIG. 6D is a cross-sectional front view of the volume-displacing member 120f of FIG. 6A in axis 6D-6D, having an elongate body 122f, as shown in FIG. 6B, with an inside through-passage 121e, positioned within the inside cavity 106 of the distal opening 41a of the male nozzle 13 as shown in FIG. 6A. The outside wall 18 of nozzle 13 forms a first liquid and air-tight seal 133 with inside sidewall 107 of the female hub 102d, and the outside wall 137f of the volume-displacing member 120f forms a second liquid and air-tight seal 123c with inside wall 41 of the male nozzle 13.

FIGS. 7A-7C illustrate one implementation of a method of loading and assembling the volume-displacing member 120f of FIG. 6A into a female hub 102d with a mandrel 550, and can be used as a method to assemble any implementation of volume-displacing member of the present invention within this application into an appropriately configured female luer hub of the present invention within this application before, during or after another component is joined to each device or apparatus, including but not limited to, a hypodermic needle, a blunt needle, a hollow tube, a valve, an extension set or the like.

FIG. 7A is one implementation of a cross-sectional side view of the method of the assembly process of the low deadspace luer apparatus 101D of the present invention shown in a first position with the volume-displacing member 120f and female luer hub 102d separated from each other, having volume-displacing member 120f ready to be placed within interior cavity 556 of a mandrel 550 having outside wall 551 and a distal endwall 552.

FIG. 7B. is a cross-sectional side view of the method of the assembly process of the luer apparatus 101D of FIG. 7A. shown in a second position with the volume-displacing member 120f positioned within female luer hub 102d by the mandrel 550. The distal end 144f of volume-displacing member 120f is now mechanically lock-fit within the interior nest 145d, as shown in FIG. 7A, by the mated engagement between the annular ring 158d of the distal inside wall 141d, as shown in FIG. 7A, of the female hub 102d and annular recess 146d of the outside wall 137f of the body 122f.

FIG. 7C. is a cross-sectional side view the method of the assembly process of the low deadspace luer apparatus 101D of FIGS. 7A. and 7B. shown in a third, assembled position with the volume-displacing member 102f lock-fit within the female hub 102d whereby the proximal end of a needle, tube or the like can be positioned and secured within the distal lumen 165, as shown in FIG. 7, of the female hub 102d prior to packaging, sterilization and use.

FIGS. 8A-8D illustrate one implementation of the low deadspace luer syringe apparatus 301 of the present invention having a one-piece volume-displacing member 320 or 320c that may be positioned onto a male nozzle 345 formed within the interior cavity 126c female luer hub 102g.

Figure 8A:
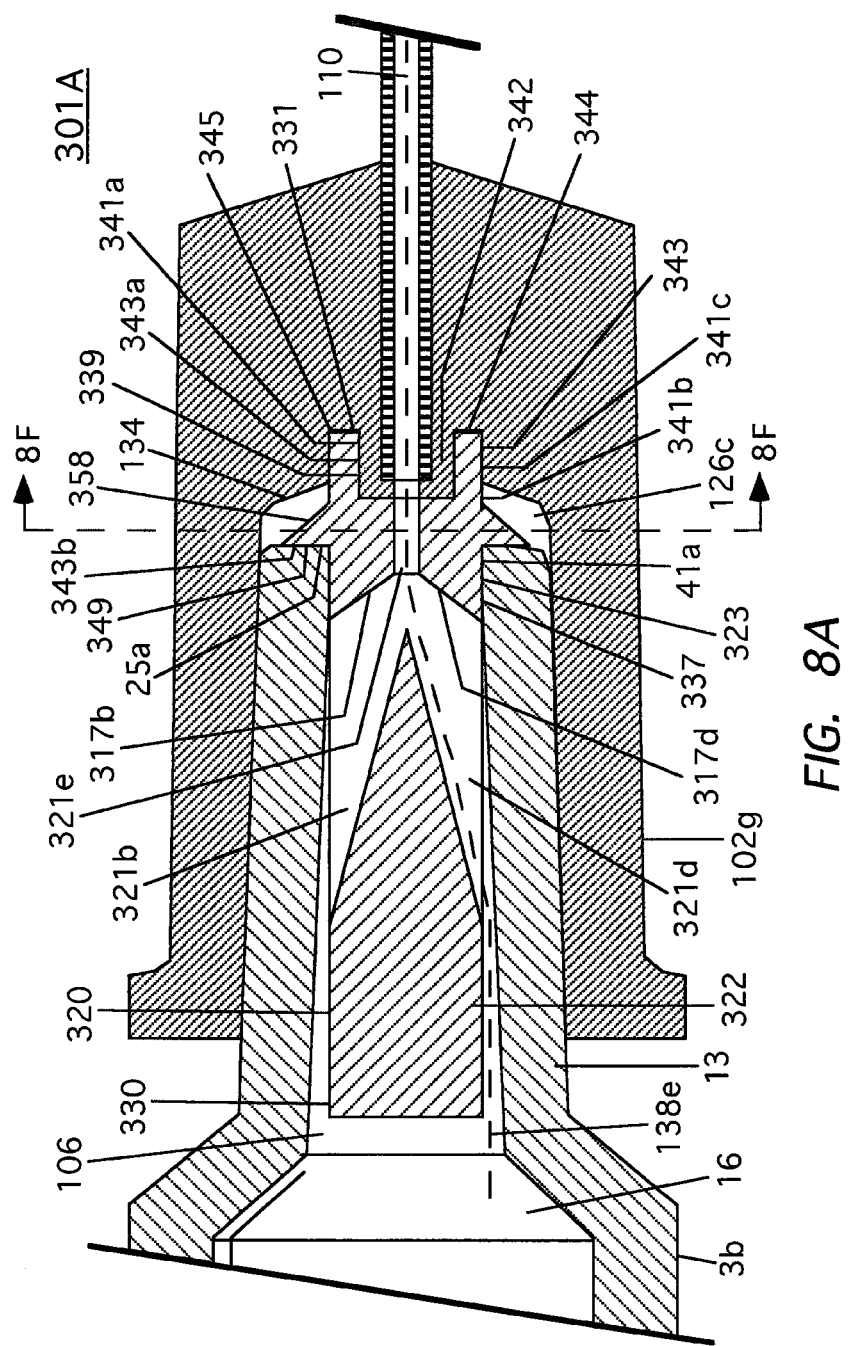
FIG. 8A is a cross-sectional side view of one implementation a volume-displacing member within a female luer hub and male luer nozzle having a combined interior cavity with a streamline flowpath.

According to one implementation of the present invention, FIG. 8A is a cross-sectional side view of the low deadspace luer apparatus 301A of the present invention in a ready-to-use state comprising a syringe 3b with a male luer nozzle 13 attached to a female luer hub 102g with a singularly-formed (monolithic) volume-displacing member 320 positioned within the interior cavity 106 of the male nozzle 13 and the distal deadspace interior cavity 126c of the female luer hub 102g. According to other implementations the volume displacing member 320 may not be a monolithic structure and may comprise multiple parts. The volume-displacing member 320 comprises an elongate body 322 with an outside wall 337, a closed proximal end 330 and a distal collar 331 formed by an outside wall 341b and inside wall 341a defining a distal hollow interior/female nest 321f, as shown in FIG. 8B, in communication with through passage 321e. The distal collar 331 is co-operable with and mateable to a collar/male nozzle 342 located surrounded by an annular groove/nest 345 of the distal interior cavity 126c of the female luer hub 102g. As shown in FIG. 8A, according to some implementations, the collar 342 is formed as a part of the female luer hub 102g. When the collar 331 is joined to collar 342, a first liquid and air-tight seal 343a is formed between the inside wall 341a of the collar 331 and outside wall 339 of collar 342. The female luer hub 102g includes an interior deadspace cavity 126c formed between the distal endwall 25a of the syringe nozzle 13 and distal endwall 134 of the female hub 102g. According to some implementations, at least one forwardly-configured, streamline or laminar flowpath 138e is formed between the hollow cavity 16, the interior cavity 106 of the male nozzle 13 and through-passages 321b, 321d and 321e formed within the volume-displacing member 320 and continuing through the needle lumen 110, is configured to allow fluid and any entrapped air or air bubbles to move out of the apparatus 301A through the distal end 111 of the needle 12. The tapered inside walls 317b and 317d of through-passages/openings 321b and 321d are configured as a vent to funnel air or air bubbles and fluid out of the apparatus 301A. The volume-displacing member 320 is configured to reduce both the inside cubic volume within the interior cavity 106 of male nozzle 13 and the fluid or gas remaining within the flowpath 138e after use. The flowpath 138e is separated from and bypasses the distal interior deadspace cavity 126c formed within female hub 102g.

The distal collar 331 comprises an outside wall 341b with an outside diameter configured to form a second liquid and air-tight seal 343 with the inside wall 341c of distal nest 345 of female luer hub 102g. A third liquid and air-tight seal 323 is formed between the outside wall 337 of the body 322 and the inside wall (diameter D3) of the distal opening 41a of the male nozzle 13. The outside wall 337 may include an annular ring with a convex profile or a protrusion 358 and may include a proximal endwall 349 configured to engage the distal endwall 25a of male nozzle 13, forming a fourth liquid and air-tight seal 343b, further separating the distal interior deadspace cavity 126c from the combined interior cavity of the flowpath 138e before, during or after use. The protrusion 358 may also act as a stop to limit the depth the male luer nozzle 13 can be positioned within the interior cavity 126 of a female luer hub 102g to reduce the probability of over-tightening a female hub onto a male nozzle of a luer lock device or connector. The annular ring or geometrically-configured protrusion 358, may be formed on the outside wall of the body of any implementation of the volume-displacing member of the present invention described herein to form a liquid and air-tight seal with the distal endwall of a male luer nozzle and limit and control the depth the male luer nozzle can be positioned within the interior cavity of a female luer hub.

The low deadspace luer apparatus of a number of the implementations of the present invention described herein, include a combined interior cavity characterized by a smooth or laminar flowpath formed from the syringe barrel cavity through the interior cavity of the luer nozzle continuing through the at least one inside through-passage of the volume-displacing member and continuing through the lumen of an attached needle or tube, bypassing the larger diameter interior deadspace cavity formed within the female luer hub distal to the male nozzle.

FIG. 8B. is an isometric view of the singularly-formed volume-displacing member 320 of FIG. 8A having an elongate body 322 with closed proximal end 330 and outside wall 337 and a distal endwall 344 with a distal collar 331 with an outside wall 341b and inside wall 341a defining a hollow nest/interior 321f in communication with the concentrically-formed through-passage 321e branching into opposing through-passages 321d and 321b, as shown in FIG. 8A, having a distal endpoint 337b at length L7 from the distal endwall 344. The body may include an annular ring 358, having convex or geometric profile, formed between the endpoint 337b and distal endwall 344. The outside wall 337 portion formed between the distal endwall 344 and endpoint 337b is formed with an outside diameter configured to form a liquid and air-tight seal 323 with the inside diameter D3 of the distal opening 41a of a male nozzle 13, as shown in FIG. 8A. The proximal end 330 may include reduced outside diameter, as shown in FIG. 8C, configured as a lead-in, to facilitate ease of insertion of volume-displacing member into distal aperture of a male luer nozzle before it is selectively attached to a female luer hub.

FIG. 8C is a cross-sectional side view of one implementation of the volume-displacing member 320a the present invention having elongate body 322a, having a proximal end 330a with an outside wall 337a with an outside diameter less than D3 formed as a lead-in to facilitate placement of the volume-displacing member into a male nozzle or another male connector as shown throughout his application. An annular protrusion 358a with a convex or geometric profile may be formed on the outside wall 337b between the distal end 344 and endpoint 337b, as shown in FIG. 8B, and may be segmented into a plurality of radial arcs.

FIG. 8D is a full front view of the volume-displacing member of FIG. 8A with a distal collar 331 configured with a distal nest 312f formed with at least one inside through-passage 321e and an annular protrusion 358 formed on outside wall 337, as shown in FIG. 8B, of the volume-displacing member 320.

FIG. 8E is a cross-sectional side view of a two-piece volume-displacing member of the present invention comprising a first volume-displacing member 320c joined with a second separate volume-displacing member 320d. The first volume-displacing member 320c includes a distal collar 331c with a hollow distal nest 321f, formed with an inside through-passage 321e and an interior cavity 321 with an inside proximal wall 371 formed within the open proximal end 330c. The collar 331c is configured with an outside wall 337b with an outside diameter less than D3 that increases to an outside diameter 337c configured to form a liquid and air-tight seal with the inside diameter D3 of the inside opening 41a of a male nozzle 13, as shown in FIG. 8A. The second volume-displacing member 320d includes a body 322d, as shown in FIG. 8G, with an outside wall 337d with an outside diameter substantially matching 337c, a closed proximal end 330d and a distal appendage 360d with outside walls 369b and 369d, as shown in FIG. 8G. A medial outside wall 337e is formed between the proximal end 330d and appendage 360d and includes an outside diameter configured to form a press-fit or compression-fit with the inside diameter of the inside wall 371 of the open proximal end 330c joining the first 320c and second 320d volume-displacing members together.

Figure 8H:
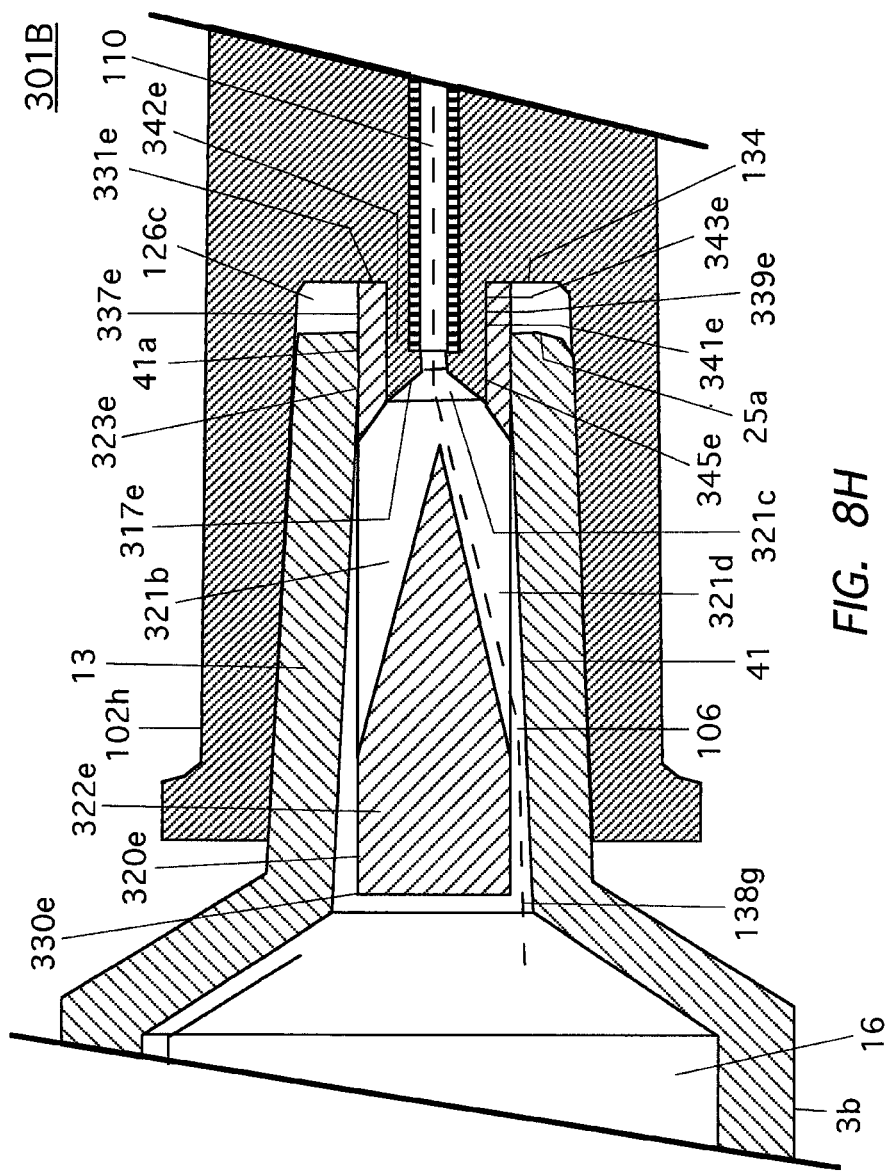
FIG. 8H is a cross-sectional side view of one implementation of a volume-displacing member positioned within a female luer hub.

FIG. 8H is a cross-sectional side view of the low deadspace luer apparatus 301B of one implementation of the present invention in a ready-to-use state comprising a syringe 3b with a male luer nozzle 13 attached to a female luer hub 102h with a singularly-formed (monolithic) volume-displacing member 320e positioned within the interior cavity 106 of a male nozzle 13 and the distal deadspace interior cavity 126c of the female luer hub 102h. According to other implementations the volume-displacing member may not comprise a monolithic structure but may instead comprise multiple parts fitted together. The volume-displacing member 320e is configured with an elongate body 322e, a closed proximal end 330e and an open end configured with a distal collar 331e with a distal nest/interior 345e. The distal interior cavity 126c of the female luer hub 102h is configured with a collar 342e that may be formed with a tapered inside wall 317e defining a proximal interior cavity 321c. A proximal endwall, formed perpendicular to the needle lumen 110 axis, may be substituted for the tapered inside wall 317e at the proximal end of the nozzle 342e. The collar 331e is press-fit or compression-fit onto collar 342e formed within the distal interior cavity 126c of the female hub 102h, whereby the inside wall 341e of the distal collar 331e is co-operable with and mateable to the outside wall 339e of collar 342e, forming a first liquid and air-tight seal 343e. A second liquid and air-tight seal 323e is formed between the outside wall 337e of the body 322e and the inside wall (diameter D3) of the distal opening 41a of the male nozzle 13. At least one forwardly-configured flowpath 138g, shown in a broken line, formed between the hollow cavity 16, the inside cavity 106 of the male nozzle 13 and through-passages/openings 321b and 321d and interior cavity 321c of the volume-displacing member 320e, and continuing through the needle lumen 110, is configured move air or air bubbles and fluid into or out of the apparatus 301B. The tapered inside wall 317e of interior cavity 321c is configured as a vent to funnel air or air bubbles and fluid out of the apparatus 301B. The volume-displacing member 320e is configured to reduce both the inside cubic volumetric capacity within the combined interior cavity and the fluid or gas remaining within in the flowpath 138g after use. The flowpath 138g is separated from and bypasses the distal interior deadspace cavity 126c formed within female hub 102h.

FIG. 8G is a full side view of the volume displacing member 320d of FIG. 8E comprising a body 322d with an outside wall 337d, a closed proximal end 330d and a distal appendage 360d with outside walls 369b and 369d. The medial outside wall 337e includes an outside diameter configured to form a press-fit or compression-fit with the inside diameter of the inside wall 371 of the open proximal end 330c of the first volume-displacing member 320c as shown in FIG. 8E.

FIG. 8F is a cross-sectional front view of the low deadspace apparatus of FIG. 8A in axis 8F-8F, having the volume-displacing member 102g configured with at least one inside through-passage 321e separated from the interior deadspace cavity 126c of the female hub 102g.

FIG. 9 is a cross-sectional side view of luer nozzle 113c of the present invention having an elongated distal opening 141a and a frustoconically-tapered outside wall 118 per Part 7. An inside sidewall 141c defines a first proximal frustoconical interior cavity 106c openly formed with second distally-formed elongate interior cavity 106d, having inside sidewall 141b with consistent inside diameter D3 and a length L10 having a parameter originating at distal endwall 125c and proximally formed up to 3 mm or 0.118 inches within the syringe nozzle 113c. The consistent distal inside diameter D3 is configured to increase length of the liquid and air-tight seal, or any other counterpart seal in this application, formed between inside wall 141b of distal opening 141a of male nozzle 113c and outside wall of the implementations of the volume-displacing member of the present invention.

FIGS. 10A-10D illustrate one implementation of the low deadspace luer apparatus 201 and of the present invention having a one-piece volume-displacing member 220 with an enlarged distal body 231, that may be positioned within an interior cavity 106 of a luer nozzle 13 and interior cavity 226 of a female luer hub 202.

FIG. 10A is a full top view of one implementation of the singularly formed volume-displacing member 220 of the present invention having an elongate body 222, with an outside wall 237 with a first outside diameter ≤D3 and closed proximal end 230, an inside through-passage 221, as shown in FIG. 10B, formed by an inside appendage 260 by opposing sidewall 269b and 269d, as shown in FIG. 10B, terminating at distal endwall 244 of enlarged distal body 231 with outside wall 237a. The outside wall 237a of distal body 231 may include a frustoconical taper reducing from the proximal endwall 249 to the distal endwall 244.

FIG. 10B illustrates a cross-sectional side view of the low deadspace luer apparatus 201 of FIG. 10A in a first position, prior to assembly, comprising a female luer hub 202 having a proximal open end 235 and frustoconical inside sidewall 207 defining an interior cavity 226 in communication with a distal interior cavity 226c formed by a distal sidewall 241 and closed endwall 234, with an aperture 232 connected with the lumen 210 of the needle 212. The volume-displacing member 220 is configured with an elongate body 222, with an outside wall 237 with a first outside diameter ≤D3 and closed proximal end 230, an inside through-passage 221, formed by an inside appendage 260 with opposing sidewalls 269b and 269d, terminating at distal endwall 244 of enlarged distal body 231 as shown in FIG. 10A, with outside wall 237a having a second outside diameter substantially equal to D4. The female hub 202 having an inside distal sidewall 241 formed distal to at least one annular ring 205 configured as a stop or protrusion 257 to form a mechanical lock-fit to retain the proximal endwall 249 of the enlarged distal body 231 of volume-displacing member 220 within the interior cavity 226c. The volume-displacing member 220 having an elongate body 222, comprising first outside diameter ≤D3 with a closed proximal end 230, and at least one through-passage 221 extending from outside wall 237 to distal endwall 244 of the at least one enlarged distal body 231 having outside sidewall 237a sealingly co-operable and mateable with inside sidewall 241 having second outside diameter substantially equal to D4. The distal endwall 244 may also form an additional liquid and air-tight seal with the endwall 234 of the hub 202 when the enlarged body 231 is positioned within interior cavity 226c.

FIG. 10C is a cross-sectional side view of one implementation of the low deadspace luer apparatus 201A of the present invention in a second, assembled position having a singularly formed volume-displacing member 220b, with an elongate body 222b with an outside wall 237b with a first outside diameter ≥D3 and at least one enlarged distal body 231a with a second outside diameter substantially equal to D4, positioned within the distal interior cavity 226c of a female luer hub 202a. The volume-displacing member 220b is formed with a first inside through-passage 221b and second opposing through-passage 221d, separated by at least one inside appendage 260a formed by opposing sidewalls 269b and 269d, converging together and communicating with a concentrically-centered through-passage 221e, terminating in the distal endwall 244a of the distal body 231a. The elongate body 222b has an outside wall 237b with an outside diameter configured to form a first annular liquid and air-tight seal 223 with the inside diameter D3 of the distal opening 41a of the male nozzle 13, and a second liquid and air-tight seal 243a is formed by the outside wall 237c of the enlarged distal body 231a and the inside sidewall 241 and endwall 234 in a distal interior cavity 226c, as shown in FIG. 10B, within the female luer hub 202a. At least one flowpath 138f, shown in a broken line, is formed between the hollow cavity 16, the inside cavity 106 of the male nozzle 13 and through-passages 221b, 221d and 221e formed within the volume-displacing member 220b, and continuing through the needle lumen 110. The flowpath 138f is configured as a vent to remove air or gas from the fluid in the apparatus and reduce the inside cubic volumetric capacity within the combined interior cavity. In use, the flowpath 138f is physically separated from the distal deadspace cavity 226c now displaced by the enlarged body 231b. The female hub 202a includes an inside sidewall 241 with at least one annular ring or protrusion, 205 forming a stop 257 configured to form a mechanical lock-fit with the proximal endwall 249, as shown in FIG. 10B, to retain the enlarged distal body 231a of the volume-displacing member 220b within the distal cavity 226c.

FIG. 10D is a cross-sectional front view of the low deadspace luer apparatus 201A of FIG. 10C invention in axis 10D-10D having a distal body 231a positioned within and displacing the cubic capacity of the distal interior cavity 226c of the female hub 202a, as shown in FIG. 10C. The outside wall 237c of the enlarged distal body 231a forms a liquid and air-tight seal 243a about the periphery of inside wall 241 of distal interior cavity 226c. The inside through-passage 221e within luer apparatus 201A bypasses the distal interior cavity 226c of the female luer hub 202a, as shown in FIG. 10C.

FIG. 11A illustrates a cross-sectional side view of one implementation of the luer apparatus 401 of the present invention comprising a female luer hub 402 and separate volume-displacing member 420c in a first position prior to assembly. Female luer hub 402 having an inside sidewall 407 with a proximal open end 435 and a distal endwall 434 defining the interior cavity 426 and distal interior cavity 426c, with an aperture 432, formed in the endwall 434, in communication with the lumen 410 of a needle 412. The distal interior cavity 426c is configured with an inside sidewall 441 with a first annular ring 405a and a second annular ring 405b having a first inside diameter, that may be continuous or segmented, formed on either side of a medial annular recess 446a configured with a second larger inside diameter. A second annular recess 446b, as shown in FIG. 11B, with a second inside diameter is formed distal to annular ring 405b. The volume-displacing member 420c is configured with an elongate body 422c, as shown in FIG. 11B, having an outside wall 437c formed with an outside diameter ≤D3 with two distal enlarged opposing resilient arcuate portions or bodies 431a and 431b, separated by an inside through-passage 421, having a proximal endwall 449c and an outside wall 437d with one radially-formed concave recess 445 formed between convex arcs 458b and 458c. The through-passage 421 originates in the outside wall 437c of the elongate body 422c and terminates at distal endwall 444a of arcuate portion 431a and distal endwall 444b of arcuate bodies 431a and 431b. The annular recesses 446a and 446b have an outside diameter substantially equal to D4 configured to mate with the radial arcs 458b and 458c to lock-fit the volume-displacing member 420c with the female hub 402, as shown in FIG. 11B.

FIG. 11B is a cross-sectional side view of the low deadspace luer apparatus of FIG. 11A shown in a second, assembled position attached to a luer syringe 3b, having the volume-displacing member 420c positioned within the cavity 426 of female luer hub 402 as shown in in FIG. 11A, whereby the enlarged distal bodies 431a and 431b of volume-displacing member 420c are mechanically secured and lock-fit within distal cavity 426c of the hub 402 by the stop 457 engaging the endwall 449c of arcuate portion 458c, as shown in FIG. 11A, when the resilient distal arcuate portions 431a and 431b are advanced axially through of annular ring 405a, recess 446a and annular ring 405b. Distal endwalls 444a and 444b, as shown in FIG. 11A, engage the endwall 434 of hub 402. The through-passage 421 of the volume-displacing member 420c is configured to vent air or gas from the fluid in the apparatus and reduce the inside cubic volumetric capacity within the combined interior cavity.

FIG. 11C is a full side view of the volume-displacing member 420 of one implementation of the present invention having singularly-formed elongate member 420b with proximal body 422b, with closed end 430b formed with two distal opposing resilient arcuate portions 431a and 431b having an outside diameter substantially equal to D4, and a proximally extending portion or body 470 with a proximal endwall 449b configured to displace an additional portion of the interior cavity 426 of a female hub 402 as shown in FIGS. 11A and 11B.

Figure 12A:
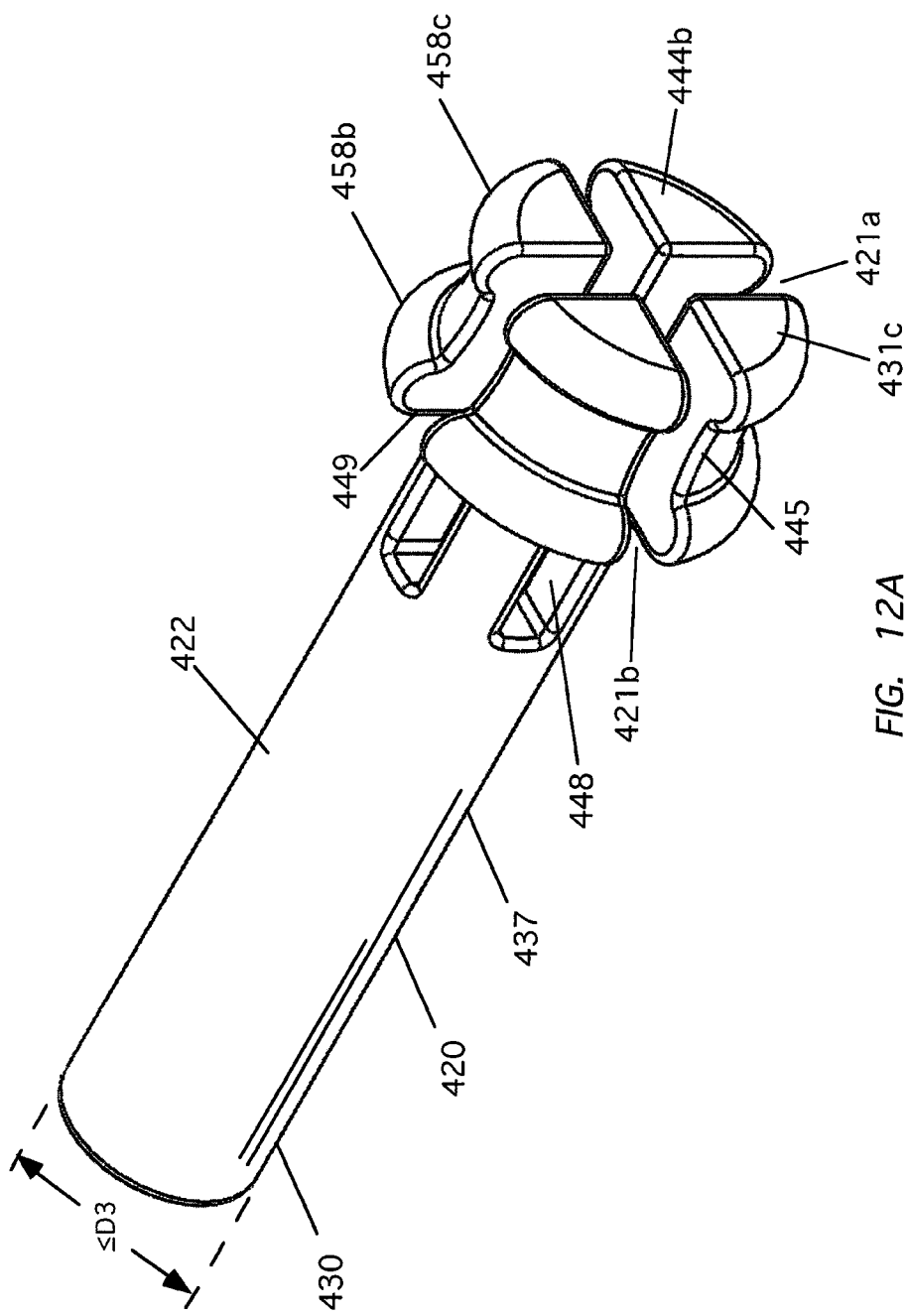
FIG. 12A is an isometric view of one implementation of a volume-displacing member having a plurality of distal apertures formed within the enlarged distal end.

FIG. 12A is an isometric view of the volume-displacing member 420 of one implementation of the present invention comprising elongate body 422, with outside wall 437 having first outside diameter ≤D3 with closed proximal end 430 and formed with four resilient arcuate distal portions 431a, 431b, 431c and 431d, separated by inside through-passages 421a and 421b. The resilient distal portions are configured with an outside wall 437 with an outside diameter substantially equal to D4, with one radially-formed concave recess 445 formed between the radially-formed convex arcs 458b and 458c. An inside through-passage 448 originates in the elongate body 422 and communicates with through-passages 421a and 421b.

FIGS. 12B-12F illustrate one implementation of a method of loading and assembling volume-displacing elongate member 420 into female hub 402 using a male nozzle 13.

FIG. 12B is a mixed cross-sectional and full side view of the method of the assembly process of the low deadspace luer apparatus 401B of the present invention shown in a first position with the components separated, having a male nozzle 13 with distal endwall 25a co-operable with the proximal endwall 449 of a volume-displacing member 420 having a plurality of apertures 421a and 421b, shown in a first, uncompressed position as an opening or width L8, formed and separating four resilient arcuate distal portions 431a, 431b, 431c and 431d that will be advanced into a female luer hub 402.

FIG. 12C is a cross-sectional side view of the method of the assembly process of the low deadspace luer apparatus 401B of FIG. 12B. in a second position having the nozzle 13, holding and axially advancing the volume-displacing member 420 into the interior cavities 426 and 426c of female hub 402. The interior cavity 426c is configured with inner annular rings 405a and 405b separated by a medial recess 446a having an inside wall 441 with an inside diameter configured and sized to urge outer radial walls 437a of distal portions 458c and 458b of resilient distal segments 431a, 431b, 431c and 431d of volume-displacing member 420 to concentrically compress as the distal portions 458c and 458b move through the inside diameters of annular rings 405 and 405b.

FIG. 12D is a cross-sectional side view of the assembly process of the low deadspace luer apparatus of FIG. 12C shown in a third position, ready to be attached to a needle 112, tube or the like, having the resilient radial portions 431a, 431b, 431c and 431d positioned and seated within distal interior cavity 426c of the female luer hub 402 by the first interference or lock-fit formed between the stop 457 in the annular convex ring 405a and the endwall 449, as shown in FIG. 12B, and a second interference or lock-fit between annular convex ring 405b and concave recess 445, as shown in FIG. 12B.

FIG. 12E is a cross-sectional front view of the low deadspace luer apparatus of FIG. 12C. in axis 12E-12E, having a volume-displacing member 420 with through-passages 421a and 421b, separating the resilient radial portions 431a, 431b, 431c and 431d, in a second concentrically compressed position C, as shown by arrows, with the through-passages 421a and 421b having a narrowed, open span L9, as radial portions 431a, 431b, 431c and 431d of volume-displacing member 420 are advanced and inserted in the female hub 402.

FIG. 12F is a cross-sectional front view of the method of the assembly process of the luer apparatus of FIG. 12D in axis 12F-12F shown in a third position having the volume-displacing member 420 inserted with in the female luer hub 402. When the volume-displacing member 420 is positioned and seated within distal cavity 426c of hub 402, the resilient portions 431a, 431b, 431c and 431d decompress and rebound to their as-manufactured or originally formed position, consistent with the first configured position of FIG. 12B.

Figure 13:
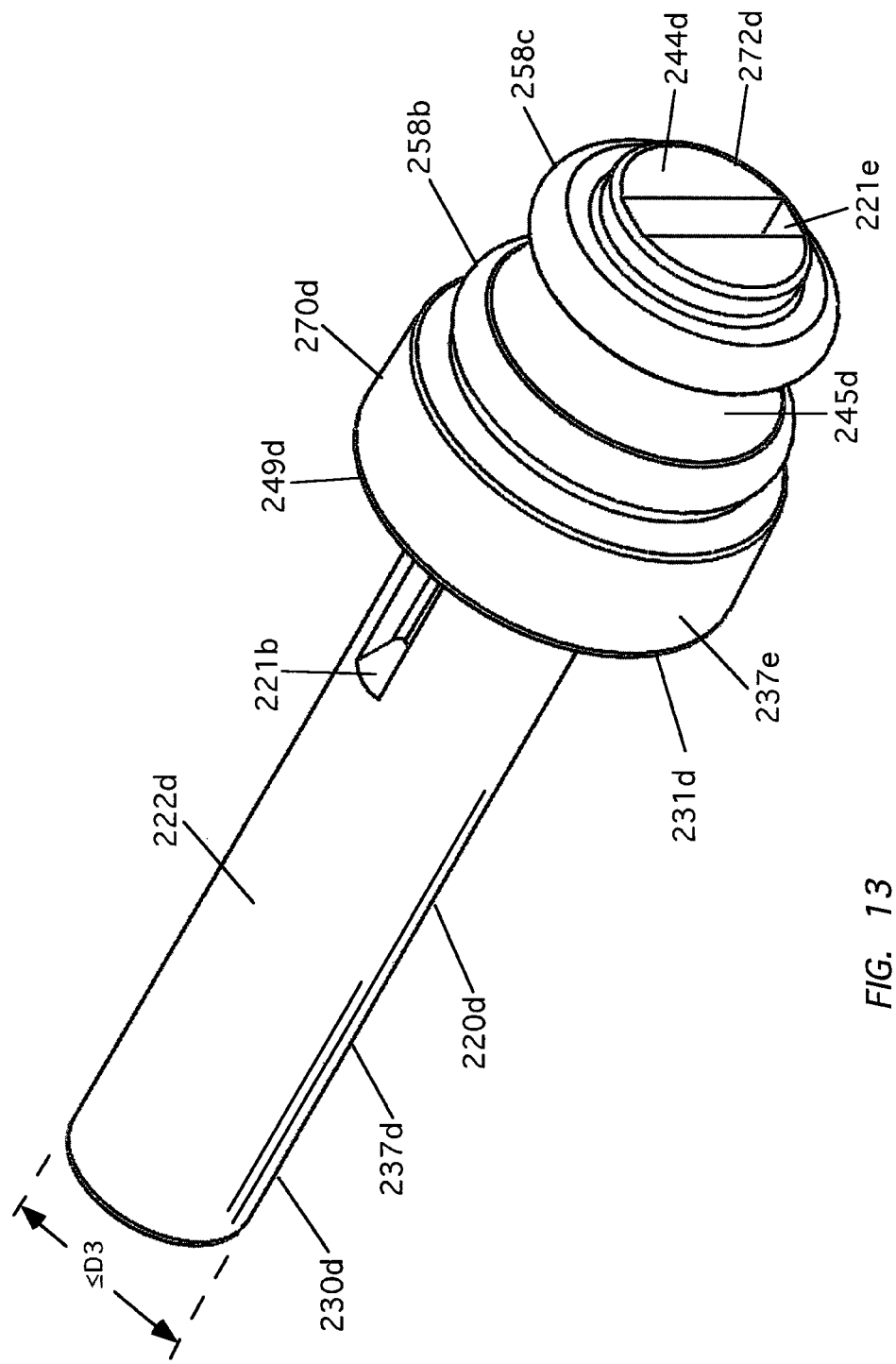
FIG. 13 is an isometric view of one implementation of a volume-displacing member having an elongate body and an enlarged distal end with a plurality of annular rings having varying outside diameters.

FIG. 13. is an isometric view of one implementation of the volume-displacing member 220d of the present invention having an elongate body 222d and at least one inside through-passage 221b, originating in the outside wall 237d, in communication with distal through-passage 231e terminating in the distal endwall 244d. The outside diameter of the elongate body 222d is configured with an outside diameter ≤D3. The volume-displacing member 220d is configured with an enlarged distal body 231d with a distal nozzle 272d and a medial recess 245d formed between annular rings 258b and 258c with a proximal end 270c with a proximal endwall 249d and a tapered outside sidewall 237c configured with an outside diameter substantially equal to D4. The distal annular rings 258b and 258c may comprise an equally-configured outside diameter or differing outside diameters.

FIGS. 14A-14C and 14E illustrate a low deadspace luer apparatus 501 of the present invention with a luer-slip syringe 3b attached to female luer hub 102. The volume-displacing members 520 or 520b can be assembled into the interior cavity of the male nozzle through the hollow cavity 16 by a mandrel or a plunger/piston as shown in FIG. 27.

FIG. 14A is a cross-sectional side view of one implementation of the low deadspace luer apparatus 501 of the present invention shown in a ready-to-use state, comprising a volume-displacing member 520 positioned within the interior cavity 106 of the nozzle 13 of a luer-slip syringe 3b and distal interior cavity 126c of a female hub 102. The separate volume-displacing member 520 comprises an elongate body 522 configured with an inside through passage or lumen 527 extending from the open proximal end 530 to the open distal end 531, as shown in FIG. 14B, with an endwall 544 and an outside sidewall 566 with a frustoconical taper configured to form a compression or slip fit forming a first liquid and air-tight seal 523 along length of the frustoconical taper of the inside wall 41 of the nozzle 13. When the syringe apparatus 501 is positioned with the needle 112 pointing up, the frustoconical endwall 517 of the proximal end 530 is configured to funnel and vent air within the fluid of the syringe barrel cavity 16 into the inside through-passage 527 when the plunger rod 15 and piston 14 are advanced toward the female hub 102. The distal endwall 544 extends beyond the distal endwall 25a of the nozzle 13 to engage and co-operate with the distal endwall 134 of the interior cavity 126c of the female hub 102, forming a second liquid and air-tight seal 543, excluding any communication of the through passage 527 with the interior cavity 126c of the luer hub 102. A laminar flowpath 538, shown in a broken line, is formed between the syringe barrel cavity 16, the inside through passage 527 and needle lumen 110. The volume-displacing member 520 and is configured to reduce both the inside cubic volumetric capacity within the distal cavity 126c of hub 102 and interior cavity 106 of syringe nozzle 13 and the fluid or gas remaining within in the flowpath 538 after use.

FIG. 14B is a cut-away view of the volume-displacing member of FIG. 14A with an inside through passage 527 formed from the open proximal end 530 to the open distal end 531.

FIG. 14C is a cross-sectional side view of one implementation of the low deadspace male syringe apparatus of the present invention comprising a luer-slip syringe 3b with a separate volume-displacing member 520b positioned within the interior cavity 106 of the male nozzle 13. The volume-displacing member 520b is configured with a resilient distal end 531b with at least one distal hook, lip or protrusion 558 with a proximal face or endwall 549 configured form a lock-fit and a liquid and air-tight seal 543 with the endwall 25a of the nozzle 13. After the at least one lip 558 is compressed and advanced through the distal inside opening 41a of the syringe nozzle 13, the at least one portion 558 rebounds and decompresses to a position consistent with the as-manufactured configuration prior to assembly. The inside wall 41 of the nozzle 13 is configured to form a second liquid and air-tight seal 523b with the outside wall 566b of the volume-displacing member 520b. Through passage 527 may include an inside diameter configured with a frustoconical profile reducing from the proximal end 530b to the distal end 531b to assist with core extraction during the manufacturing process.

Figure 14D:
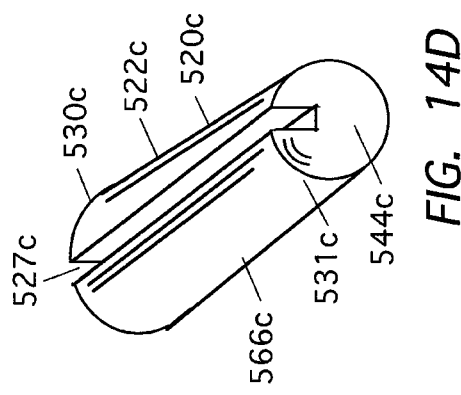
FIG. 14D is an isometric side view of one implementation of a volume-displacing member with at least one channel formed along the outside frustoconical wall.

FIG. 14D an isometric view of one implementation of the volume-displacing member 520c of the present invention comprising an elongate body 522c, with a distal endwall 544c, with at least one through passage, slot or channel 527b formed axially along the outer wall 566c, extending from the proximal end 530c to the distal end 531c. The outside wall 566c may be configured to include a substantially 6% frustoconical taper.

FIG. 14E is a cross-sectional front view of the low deadspace syringe apparatus of FIG. 14A in axis 14E-14E having the volume-displacing member 520 positioned within the male nozzle 13 with an inside diameter D3 formed in the distal opening 41a of the male nozzle 13 as shown in FIG. 14A. The inside wall 107 of the female hub 102 is configured to form a first liquid and air-tight seal 33 with outside wall 18 of syringe nozzle 13, and the inside wall 41 of the nozzle 13 is configured to form a second liquid and air-tight seal 523 with the outside wall 566 of the volume-displacing member 520.

FIG. 15A is a cross-sectional side view of one implementation of the low deadspace luer syringe apparatus 601 of the present invention comprising a volume-displacing member 620 positioned within the interior cavity 106 of a male luer nozzle 13 and distal interior cavity 126c of a female luer hub 102 attached to a syringe 3b. The volume-displacing member 620 comprises a body 622 with an outside wall 637 with opposing inside through-passages 621b and 621d converging with a distally-formed concentrically-centered through-passage 621e, as shown in FIG. 15C, terminating in endwall 644 having an outside diameter <D3 as shown in FIG. 15C. The distal end 631 of the volume-displacing member 620 is configured with frustoconically-reducing outside wall 666 configured to form a first liquid and air-tight seal 623 with the inside opening 41a of the male nozzle 13. The seal 623 forms a friction or compression-fit to maintain position of volume-displacing member 620 within male nozzle 13 before, during or after use. The distal end 631 extends beyond the distal end 25a of the male nozzle 13 and the distal endwall 644 engages the distal endwall 134 of the female hub 102 forming a second liquid and air-tight seal 643, excluding any communication of the through-passage 621e with the interior cavity 126c of the luer hub 102. As shown in FIG. 15C, the body 622 includes two opposing tapered distal inside walls 617c and 617d and an inside appendage 660 formed by tapered inside walls 669 and 669a, defining the inside through-passages 621b and 621d formed with through-passage 621e configured to funnel fluid and air or air bubbles into or out of the low deadspace apparatus 601. A smooth or laminar flowpath 638, shown in a broken line, is formed between the syringe barrel cavity 16, the interior cavity 106 of the male nozzle 13 and through-passages of 621b, 621d and 621e of the volume-displacing member 620 and the lumen 110 of the needle 112.

FIG. 15B is full top view of the volume-displacing member of FIG. 15A comprising an elongate body 622 with a closed proximal end 630, as shown in FIG. 15A, with an outside diameter ≥D3 and at least one inside through-passage/opening 621b having at least one inside appendage 660.

FIG. 15C is cross-sectional side view of the volume-displacing member of FIGS. 15A and 15B comprising an elongate body 622 formed with opposing distal tapered inside walls 617c and 617d and at least one inside appendage 660 formed by opposing inside walls 669 and 669a defining two opposing inside through-passages 621b and 621d converging a distally-formed through-passage 621e terminating in the distal endwall 644 as shown in FIG. 15A.

FIG. 15D is a cross-sectional front view of the low deadspace syringe apparatus of FIG. 15A of the present invention in axis 15D-15D having the volume-displacing member 620 with at least one inside through-passage 621e separated from and passing through the interior deadspace cavity 126c of the female hub 102.

Figure 16B:
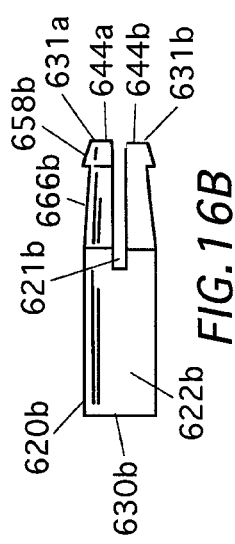
FIG. 16B is a full side view of one implementation of a volume-displacing member having an inside through-passage and a distally formed tapered outside wall with a distal lip or hook.
Figure 16A:
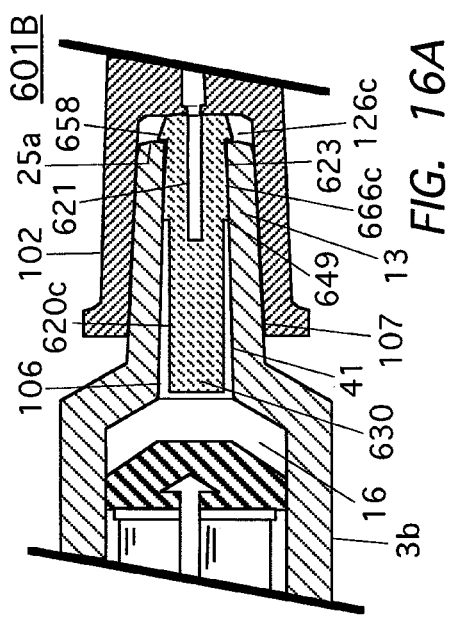
FIG. 16A is a cross-sectional side view of one implementation of a low deadspace luer syringe apparatus with a volume-displacing member positioned within a luer nozzle attached to a female hub.

FIG. 16A is a cross-sectional side view of one implementation of the low deadspace syringe apparatus 601B of the present invention shown in a ready-to-use state, comprising a volume-displacing member 620c positioned within the interior cavity 106 a male luer nozzle 13 and distal interior cavity 126c of a female luer hub 102 attached to a syringe 3b. The volume-displacing member 620c comprises a distally formed tapered frustoconical outside wall portion 666c configured to form first compressive, wedge fit and liquid and air-tight seal 623a with the inside wall 41 of the nozzle 13, and a distal lipped portion 658 configured to hook over and form a lock-fit with the distal endwall 25a of the syringe nozzle 13.

FIG. 16B is a full side view of one implementation of the volume-displacing member 620b of the present invention having an elongate body 622b with an inside through-passage 621b separating a first distal arcuate end 631a with an endwall 644a and a second, opposing distal arcuate end 631b with an endwall 644b.

Figure 17C:
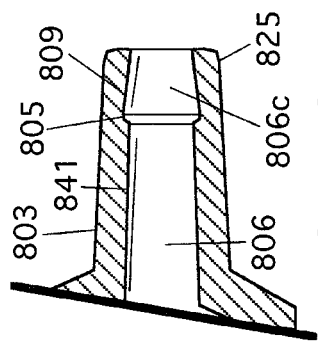
FIG. 17C is a cross-sectional side view of the luer nozzle of FIG. 17A.
Figure 17B:
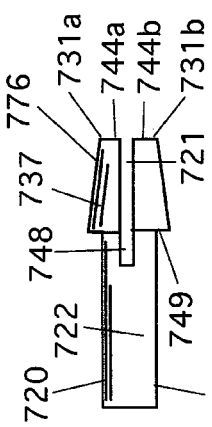
FIG. 17B is a full side view of the volume-displacing member of FIG. 17A having a resilient distal end with an enlarged tapered body configured to form lock-fit with a recess within a syringe nozzle.
Figure 17A:
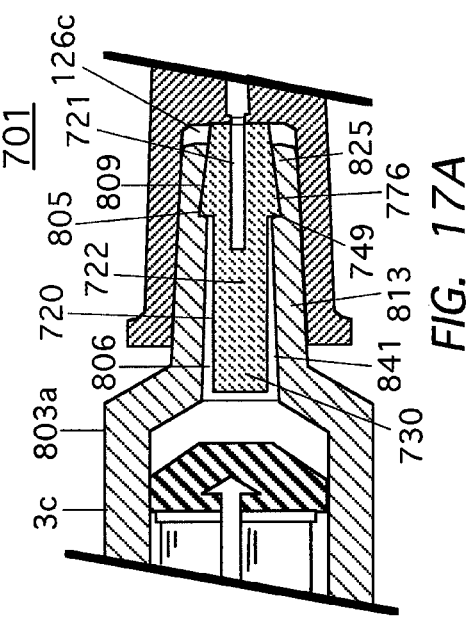
FIG. 17A is a cross-sectional side view of one implementation of a low deadspace luer syringe apparatus with a volume-displacing member with a frustoconical distal end positioned within a frustoconical recess formed within a luer nozzle attached to a female hub.

FIG. 17A is a cross-sectional side view of one implementation of the low deadspace syringe apparatus 701 of the present invention shown in a ready-to-use state comprising a volume-displacing member 720 positioned within the interior cavity 806 a male luer nozzle 813 and distal interior cavity 126c of a female hub 102 attached to a syringe 3c. The syringe nozzle 813 comprises an inside wall 841 and a distal frustoconical recess 806c, as shown in FIG. 17C, formed by inside wall 809 with a proximal inside corner 805 configured to mate with and engage the outside wall 776 and the proximal endwall 749 of the distal body 737 of the volume-displacing member 720 as shown in FIG. 17B. The volume-displacing member 720 is formed with at least one through-passage 721, as shown in FIG. 17B configured to vent air or gas from the fluid in the apparatus 701 and reduce the inner cubic volumetric capacity within the interior cavities 806 and 806c of the nozzle 813 as shown in FIG. 17C.

FIG. 17B is a full side view of the volume-displacing member 720 of FIG. 17A having an elongate body 722 with a closed proximal end 730 and an inside through-passage 721 separating a first distal arcuate end 731a with an endwall 744a and a second opposing arcuate end 731b with side or endwall 744b, and an enlarged distal portion or head 737 with a distally reducing frustoconical tapered wall 776 and a proximal endwall 749.

FIG. 17C is a cross-sectional side view of the syringe nozzle of FIG. 17A comprising a luer-slip syringe 803 with a syringe nozzle 813 having a distal end 825, the interior cavity 806 and an enlarged inside cavity 806c formed by a distally tapering inside wall 809 and proximal side or corner 805 of the syringe nozzle 813.

FIG. 18 is a cross-sectional side view of one implementation of the pre-filled low deadspace luer syringe apparatus 901 of the present invention comprising a luer-slip syringe 3b with a nozzle 25 closed by selectively removable low deadspace syringe cap 900, having volume-displacing member 920 in a first sealing position within the interior cavity 106 of a male nozzle 13. The cap 900 is configured with a volume-displacing member 920 with an elongate body 922 with an outside wall 937, with a distal end 931 with an outside diameter configured to form first liquid and air-tight seal 923 with the inside diameter D3 of the inside wall 41 of distal opening 41a of the syringe nozzle 13. The endwall 25a of the nozzle 13 forms a second liquid and air-tight seal 943 with the distal inside endwall 934 of the syringe cap 900. The cap 900 comprises a proximally extending outer, annular sleeve or collar 954 having an inside wall 907a configured to mate and form a third liquid and air-tight seal 933 with the outer frustoconical wall 18 of the male nozzle 13. The first seal 923 is supplemented by second seal 943 and third seal 923 to maintain a plurality of contact surfaces keeping the fluid 116a sterile within the syringe nozzle 13 prior to use. The syringe nozzle 13 and syringe cap 900 may be configured to have a plurality of seals 923, 933 and 943 to seal fluid with the syringe 3b but may include at least one seal needed to maintain the sterility of the fluid 116a within the syringe 3b.

FIG. 19 is cross-sectional side view of one implementation of the smart, leak-sensing, pre-filled low deadspace luer syringe apparatus 901B of the present invention comprising a luer-lock syringe 3 with a nozzle 13 closed and sealed by a selectively removable low deadspace syringe cap 900b, having a volume-displacing member 920 in a first position within the interior cavity 106 of the nozzle 13. The cap 900b is configured with at least one proximal lug or threaded portion 9 to form a mechanical attachment with the threads 8 formed within the distal luer-lock collar 4 when the cap 900b is rotated onto the syringe 3. The syringe 3 or syringe cap 900b may include an annular or segmented leak-detection member 960 having a color-changing, fluid-sensitive pigment. It is imperative that the medicine, therapeutic or vaccine 116a within the hollow cavity 16 syringe 3 remains sterile before use. The leak-detection member 960 includes an irreversible hydro-chromic pigment (usually black or blue), where any color change will visually alert an individual in the supply-chain at least one seal 923, 933 or 943 between the syringe nozzle 13 and syringe cap 900b is leaking and has been breached. Leak-detection component 960 may comprise a lint-free fabric or lint-free cellulose-based substrate formed, printed or impregnated with an irreversible, hydro-chromic pigment. The syringe nozzle 13 and syringe cap 900b may be configured to have a plurality of seals 923, 933 and 943 to seal fluid 116a with the syringe 3 but may include at least one seal needed to maintain the sterility of the fluid 116a within the syringe 3. The seals 923, 933 and 943 of FIG. 19 are configured with the same contact surfaces formed at the interfaces described in the nozzle 13 and cap 900 of FIG. 18. The prefilled cap 900b is normally formed with a solid-colored material and the syringe 3 is normally formed with a translucent material, so the leak-sensing member 960 is positioned where it is visible through the syringe collar 4. The leak-sensing member or ring 960 may be positioned within distal interior cavity 126c of the female hub disclosed in this application to visually identify a breach of at least one liquid and air-tight seal formed on the outside diameter of the volume displacing member of the present invention.

FIG. 20A is a cross-sectional side view of one implementation of the smart, tamper-resistant, capped pre-filled low deadspace luer syringe apparatus 901C of the present invention in a first, sealed, capped position. The interior cavity 106 of the syringe nozzle 13 is closed by a selectively removable low deadspace syringe cap 900c configured with a resilient volume-displacing member 920 with a distal end 931 with an outer wall 937 forming a liquid and air-tight seal 923 with the inside wall 41 of the distal opening 41a of the syringe nozzle 13. The volume-displacing member 920 is shown in a first sealed position within the interior cavity 106 of the luer nozzle 13. The syringe nozzle 13 and syringe cap 900c may be configured to have a plurality of seals 923, 933 and 943 to seal fluid with the syringe, but may include at least one seal needed to maintain the sterility of the fluid within the syringe. The seals 923, 933 and 943 of FIG. 20A are configured with the same contact surfaces formed at the interfaces described in the nozzle 13 and cap 900 of FIG. 18. The syringe apparatus 901C includes a RFID tag 973 attached to a frangible, adhesive backed label 970, having a proximal end 971 and a distal end 972. The frangible label 970 wraps around the circumference of the cap 900c and the syringe 3, keeping the components joined together. The label 970 may include a machine readable and human readable data information per the Health Industry Bar Code Supplier Labeling Standard, providing a Unique Device Identification system designating the device, expiration date, method of sterilization, catalog number, manufacturer and contents within the syringe 3. An intact label 970 indicates the cap 900c has not been re-positioned or removed from the syringe 3. The syringe apparatus 901C may also include a leak-detection component 960 of syringe apparatus 901B. The readable data establishes a chain of custody and makes the syringe and medication traceable from the source and identifies the patient the medication was administered to.

The Radio Frequency Identification system comprises two components: readers and tags. The RFID tag emits radio waves with its identity and other information to a reader having an antenna. A passive RFID tag does not include a battery and is powered by the reader. An active RFID tag is powered by a battery.

FIG. 20B is a cross-sectional side view of the smart, low deadspace pre-filled luer syringe apparatus of FIG. 20A comprising a luer-lock syringe 3 and syringe cap 900c, in a second and opened position. When the syringe cap 900c is removed from the syringe 3, the RFID tag 973 transmits or broadcasts a decodable signal 980 to a RFID reader 981 indicating the label 970 has been torn and one or more seals 923, 933 and 943 between syringe 3 and syringe cap 900c have been broken or breached. The signal 980 may also be transmitted from the RFID tag 973 on distal portion 972 of the label 970 on the cap 900c.

FIG. 21A a cross-sectional side view of the low deadspace luer syringe apparatus 1001 of the present invention comprising a luer-slip syringe 1003 with a hollow barrel 16 formed with the interior cavity 1006 of a nozzle 1013, having at least one integrally-formed volume-displacing member 1020 formed within the syringe nozzle 1013 and is connected together by at least one integrally-formed strip 1068, shown between two broken lines, formed at distal end 1025 with the inside wall 1041 of the nozzle 1013 and the outside wall 1037 of the volume-displacing member 1020. The volume-displacing member 1020 is configured with an elongate body 1022, a closed proximal end 1030 and a distal end 1031 with at least one distal aperture 1021 in communication with at least one through passage 1027, formed alongside the axial length of the inside wall 1041 of the nozzle 1013 and the outside wall 1037 of the elongate member 1020, forming a flowpath 1038 for venting air and fluid from the inside cavity of the syringe apparatus. The inside sidewall 1041 of the luer nozzle 1013 of the present invention may be formed in a cylindrical configuration with a consistent outside diameter forming a hollow cavity between the outside wall 1037 of the volume-displacing member 1020.

The at least one integrally-formed strip 1068 and the at least one through passage 1027 formed alongside the axial length of the inside wall 1041 of nozzle 1013 and outer wall 1037 of elongate body 1022 allows the volume-displacing member 1020 to be injection molded and singularly-formed with and within the nozzle 1013 by a single injection shot and cycle. Additionally, a substantially uniformly-thick wall section 1047 of the nozzle 1013 can be molded, curing evenly and forming the required, smooth, conical mating surface outside wall 1018 ensuring an air and liquid-tight seal is formed with the conical mating surface inside wall 107 of the female luer hub 102.

FIG. 21B is a cross-sectional front view of the syringe apparatus of FIG. 20A in axis 21B-21B comprising a female luer hub 102 attached to a male nozzle 1013, as shown in FIG. 21, integrally-formed with a connective strip 1068 and the outside wall 1037 of the elongate body 1022 having an outside diameter <D3. At least one axially extending through passage 1027 is formed along the length of the inside wall 1041 of the nozzle 1013 and the outside wall 1037 of the volume-displacing member 1020 as shown in FIG. 21.

FIG. 22A is a cross-sectional side view of the low deadspace luer syringe apparatus 1001B of the present invention comprising a syringe 1003b in a ready-to-use state with a distal nozzle 1013b configured with integrally-formed elongate strips 1068a and 1068b, as shown in FIG. 22B, molded within the interior cavity 1006b and surrounded by opposing through passages 1027a and 1027b formed alongside the axial length of the nozzle 1013b and outside wall 1037, as shown in FIG. 22B, of the volume-displacing member 1020b. The axial length of the elongate member 1020b may be formed by shortening distal end 1031b to form a recessed bowl, pocket or nest within the distal opening 1041a of the nozzle 1013b. A shortened distal end 1031, 1031b or 1031c forming a recessed nest within the distal opening 1041a, 1041b or 1041c of the nozzle 1013, 1013b and 1013c respectively, would be compatible with a number of intravenous connectors currently used to inject medicine or the like into an infusion line. The distal end 1031*b* of volume-displacing member 1020*b* may be formed proximal to, equal to, or distal to distal end 1025*b* of the nozzle 1031*b*.

FIG. 22B is a cross-sectional front view of the low deadspace syringe apparatus of FIG. 22A in axis 22B-22B comprising a female luer hub 102 attached to a luer syringe 1003*b* with a nozzle 1013*b*, as shown in FIG. 22, integrally-formed with a first connective strip 1068*a* and a second connective strip 1068*b* and a volume-displacing member 1020*b* having a plurality of axially extending through passages 1027*a* and 1027*b* formed alongside the body 1022*b*. The distal opening 1041*b* of the nozzle 1013*b*, as shown in FIG. 22, is configured with an inside diameter D3.

FIG. 23A is a cross-sectional side view of another implementation of the low deadspace luer syringe apparatus 1001C of the present invention comprising a luer-slip syringe 1003*c* with a hollow barrel 16 formed with the interior cavity 1006*c* of a nozzle 1013*c* with distal end 1025*c* and at least one integrally-formed elongate strip 1068*c*, shown between two broken lines, extending the length of the volume-displacing member 1020*c*, reducing the cubic volume within the interior cavity 1006*c*. At least one through passage 1027 is formed alongside the integrally-formed volume-displacing member 1020*c*, in communication with at least one distal aperture 1021*c*, as shown in FIG. 23A, formed with a distal cavity 1050, forming a fluid and gaseous path, configured as a vent to remove air or air bubbles from the fluid within the syringe 1003*c* before the fluid is dispensed to a patient or other luer apparatus.

FIG. 23B is a cross-sectional front view of the luer syringe apparatus of FIG. 23A in axis 23B-23B comprising a female luer hub 102 attached to a luer syringe 1003*c* with a syringe nozzle 1013*c*, with at least one singularly-formed, axial strip 1068*c* extending the length of the singularly-formed volume-displacing member 1020*c*, with at least one through passage 1027, distal cavity 1050 and distal aperture 1021*c*.

The method of monolithically forming volume-displacing member 1020, 1020*b*, 1020*c* or 1020*d* with hub 1003, 1003*b*, 1003*c* or 1003*d* and luer nozzle 1013, 1013*b*, 1013*c* or 1013*d* of the present invention comprises: first, filling molten plastic resin into the first cavity forming hub 1003, 1003*b*, 1003*c* or 1003*d* and luer nozzle 1013, 1013*b*, 1013*c* or 1013*d*; second, filling molten plastic resin into the at least one cavity forming the least one or more strip 1068, 1068*b*, 1068*c* and 1068*d*; and third, filling molten plastic resin into the cavity forming elongate body 1022, 1022*b* 1022*c*, 1022*d* of volume-displacing member 1020, 1020*b*, 1020*c* or 1020*d* as molten plastic resin displaces the air within the cavities.

FIG. 24 is a cross-sectional front view of one implementation of the low deadspace syringe apparatus of the present invention comprising a female luer hub 102 attached to a luer nozzle 1013*d* with a plurality of singularly-formed, axial strips 1068*a*, 1068*b* and 1068*c*, that may be formed along a portion of, or the entire length of the integrally-formed volume-displacing member 1020*d* for reducing the inner cubic volume within the interior cavity 1006*d*. Through-passages 1027*d*, 1027*e* and 1027*f* are formed along the axial length of the volume-displacing member 1020*d*.

FIGS. 25 and 26 illustrate a luer syringe apparatus 601 and 601D of the present invention comprising the method of assembling separate volume-displacing member 620, or 620*b*, into the interior cavity 106 of the syringe nozzle 13 by advancing the plunger rod 15 and piston 614 configured with a cavity or pocket 605 for releasably holding the proximal end 630 of the volume-displacing member 620, or 620*b*. When the plunger 15, piston 614 and volume-displacing member 620, or 620*b* are moved to the distal end of the syringe 3*b*, the distal end 631 of the elongate member 620 is positioned within the interior cavity 106 of the syringe nozzle 13. This implementation of the method of assembly eliminates the need for a separate, time-consuming assembly step whereby a mandrel is used to place the volume-displacing member within the luer nozzle of the present invention. A three second savings in cycle-time assembling 100,000,000 volume-displacing members of the present invention into the equivalent number of syringe nozzles translates to a reduction of approximately 9.5 years of assembly time.

FIG. 25. illustrates the low deadspace luer syringe apparatus 601 of FIG. 15A comprising a luer-slip syringe 3*b* with a hollow barrel 16, having a plunger rod 15 and piston 614 having a cavity or pocket 605 in a first position disposed at the proximal end of the hollow inner cavity 16, with the cavity 605 releasably holding the proximal end 630 of the elongate body 622 of the volume-displacing member 620. The plunger rod 15, piston 614 and volume-displacing member 620 are axially moveable "M" within the barrel 16.

FIG. 26 illustrates the low deadspace luer syringe apparatus 601B of the present invention comprising a luer-slip syringe 3*b* with a hollow barrel 16, with the plunger rod 15 and piston 614 having a cavity or pocket 605 shown in a second, assembled ready-to-fill position disposed at the distal end of syringe 3*b*, with the volume-displacing member 620*b* of FIG. 16B positioned and lock-fit within interior cavity 106 of syringe nozzle 13 as shown in FIG. 25. The distal end 631*b* of the volume-displacing member 620*b* is configured with a tapered outside wall 666*b* forming a compressive liquid and air-tight seal 633*b* with the inside wall 41 of the syringe nozzle 13. A lock-fit formed between the endwall 25*a* of the nozzle 13 and the lip 658*b* of the volume-displacing member 620*b*.

FIG. 27 illustrates a luer low deadspace syringe apparatus 501B of the present invention in a ready-to-use state. The volume-displacing member 520*b* is assembled and lock-fit into the interior cavity 106 of the syringe nozzle 13 of syringe 3*b*. The plunger rod 15 is secured to the piston 514 configured with a distal elongate member 522*d* configured to push the fluid 116*a* within the through-passage 527 from the syringe 3*b* into an attached needle, port or infusion line when the barrel 16 is emptied. The through-passage 527 of the volume-displacing member 520*b* is releasably positioned on the elongate member 522*d* during the assembly process. When the plunger rod 15 and piston 514 are advanced to the distal end of the hollow barrel 16, the volume-displacing member 520*b* is pushed through the interior cavity 106 of the nozzle 13 and the distal lip 558*b* extends past the endwall 25*a* of the nozzle 13, locking the volume-displacing member 520*b* within the interior cavity 106 of the nozzle 13.

Figure 28:
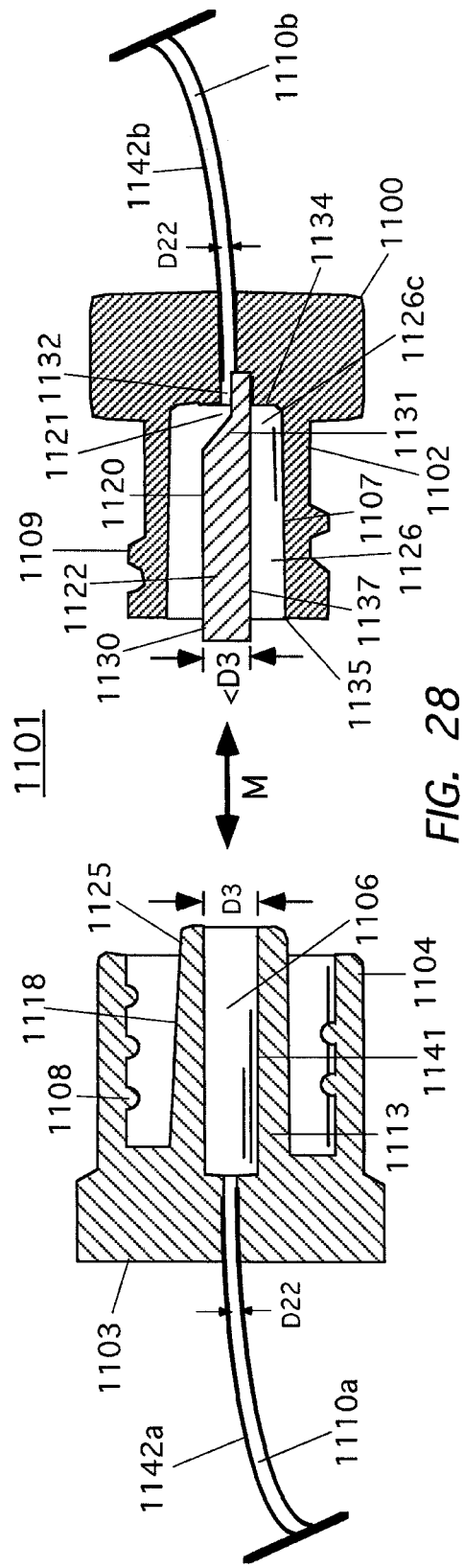
FIG. 28 is a cross-sectional side view of a low deadspace luer-lock infusion line apparatus having a first male connector and a second female connector having a volume-displacing member, separated from each other.

FIG. 28 is a cross-sectional side view of the low deadspace luer lock connector apparatus 1101 of another implementation of the present invention with a first male connector 1103 separated from a second female connector 1100. The male connector 1103 is attached to a hollow tube 1142*a* with an inside diameter D22 within a lumen 1110*a* in communication with the interior cavity 1106 of a frustoconical male nozzle 1113 configured with an inside diameter D3 formed within the inside sidewall 1141 and an outside wall 1118 with distal end 1125 and endwall 1125*a*. A distal collar 1104 includes inside threads 1108 for accepting threads or lugs of a separate female luer lock connector. A second female luer hub 1102 is configured with an inside sidewall 1107 and a distal endwall 1134 defining a frustoconical interior cavity 1126. A volume-displacing member 1120, configured with an elongate body 1122 and an outside wall 1137 with an outside diameter <D3 and a closed proximal end 1130 and a distal end 1131 with an inside through-passage 1121, is positioned with in the interior cavity 1126. The female hub 1102 is attached to a trailing hollow tube 1142b with a lumen 1110b having inside diameter D22 in communication with the interior cavity 1126c. The volume-displacing member 1120 can be positioned within cavity 1126 of the hub 1102 reduce the interior cubic capacity of cavity 1126. Hub 1100 is attachable onto hub 1103 by rotating the outside threads 1109 into the threads 1108 of the collar 1104.

Figure 29:
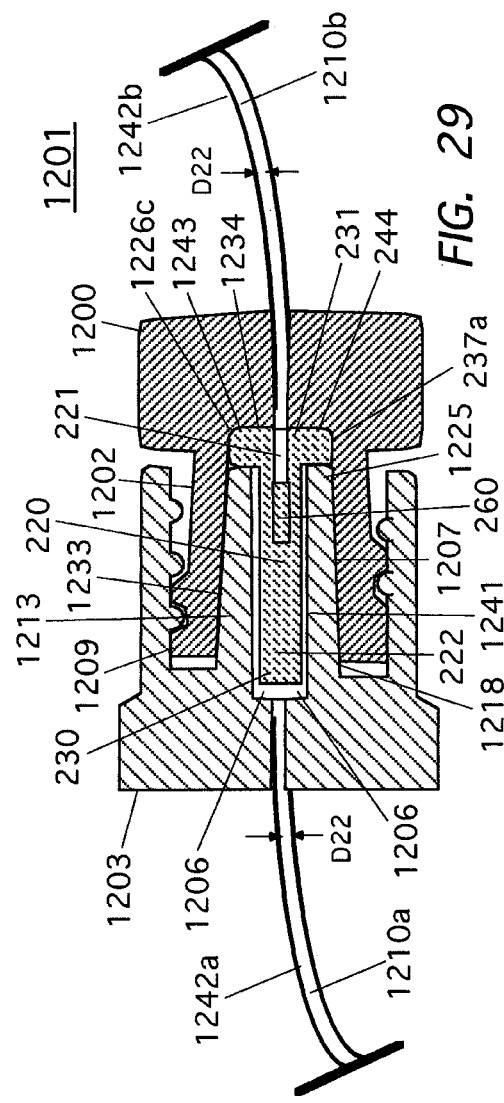
FIG. 29 is a cross-sectional side view of a low deadspace luer lock infusion line connector apparatus having the first male connector and a second female connector having a volume-displacing member with an enlarged distal body, shown in a second position joined with each other.

FIG. 29 is a cross-sectional side view of the low deadspace luer lock connector apparatus 1201 of the present invention with a first connector 1203 joined with a second connector 1200 with a volume-displacing member 220 of FIG. 10A is positioned within an interior cavity 1206 of a male nozzle 1213 configured to reduce the volumetric capacity within the interior cavity of the connectors 1200 and 1203. The volume-displacing member 220 is configured with an elongate body 222 with a closed proximal end 230 and an enlarged distal end 231 and an outside wall 237a and an endwall 244 with a through passage 221 in communication with the interior cavity 1206 and lumen 1210b of the tube 1242b and lumen 1210a of the tube 1242a. A first liquid and air-tight seal 1233 is formed between the outside wall 1218 of the male nozzle 1213 and the inside wall 1207 of the hub 1202, and a second liquid and air-tight seal 1243 is formed between the outside wall 237a of the enlarged head 231 and the inside wall 1234 of the interior cavity 1226c. The flowrate between the female connectors 1100 or 1200 and male connectors 1103 and 1203 respectively is configured on the inside diameter D3 of the tubing 1242a and 1242b and ranges from 0 ml/minute to 1,200 ml/minute to conform with Table D.1 of Part 7. The volume-displacing member may be configured with a through-bore forming a laminar flow path between the proximal lumen 1110a and distal lumen 1110b, allowing the outside wall of the volume displacing member to form a liquid and air-tight seal with the inside wall of the male nozzle and an inside wall of the distal interior cavity of the female hub as shown in the volume-displacing member 520 of FIG. 14A.

FIG. 30 illustrates a cross-sectional side view of the prior art luer lock connector apparatus 1301 shown in the neuraxial or NRfit® configuration of the ISO Standard—Small bore connectors for liquids and gases in healthcare applications—Part 6: Connectors for neuraxial applications, with a male connector 1303 separated from a female connector 1300. The male connector 1303 is configured with a proximal lumen 1310a configured with the inside cavity 1306 of the male nozzle 1313 having an inside sidewall 1341. The nozzle 1313 includes a conical mating surface outside sidewall 1318 with a proximal end 1324, a distal end 1325 with an endwall 1325a, surrounded by a fixed outside collar 1304 having inside threads 1308 for accepting the threads or lugs 1309, as shown in the female luer hub connector 1300. The female connector 1300 is configured with proximal hub 1302 with a conical mating surface inside wall 1307a formed between an open proximal end 1335 and a distal endwall 1334, defining an interior cavity 1326 and a medial interior cavity 1326c. A distal male nozzle 1313b is configured with an inside wall 1307b formed with the endwall 1334 and a distal end or nozzle 1325b defining a distal interior cavity 1365. The medial interior cavity 1326c is openly connected to the interior cavity 1365 and interior cavity 1326. The female hub connector 1300 may include at least one fin 1305, not shown here, to rotate the hub connector 1300 onto the male connector 1303. When the connectors 1303 and 1300 are joined together, a deadspace is formed within the combined interior cavity 1306, 1326c and 1365. The male connector 1303 and female connector 1300 are configured in a luer-lock configuration whereby the lugs or threads 1309 of the female hub 1302 form a lock-fit with the threads 1308 of the outside collar 1304 when the female connector 1300 is rotated onto the male connector 1303. The female connector and male connector may also comprise a slip fit configuration, whereby lugs 1309 of the female connector 1300 and threaded collar 1304 of male connector 1303 are not included.

Per part 6, the male nozzle 1313 is configured with an interior cavity 1306 with an inside sidewall 1341 and a distal inside opening 1341a having an inside diameter parameter D13, measuring between a nominal/maximum diameter of 1.15 mm/2.30 mm or 0.0455 inches/0.0905 inches. The male connector 1303 can be configured with a syringe, female hub, adapter or another luer device. The male nozzle 1313 is configured with an outside wall 1318 having a 5% nominal taper with a distal end 1325 having an outside diameter parameter D14, measuring between a minimum/ nominal/maximum diameter of 3.17 mm/3.21 mm/3.25 mm or 0.1358 inches/0.1381 inches/0.1405 inches at the position L14, where the male taper of outside diameter of the distal end 1325 of the nozzle 1313 measures 0.5 mm or 0.0196 inches (basic dimension) from the distal endwall 1325a. The outside wall 1318 of the proximal end 1324 of the male nozzle 1313 is configured with an outside diameter parameter D15, measuring between a minimum/nominal/maximum diameter of 3.45 mm/3.51 mm/3.57 mm or 0.1358 inches/0.1381 inches/0.1405 inches, at position L15, where the male taper of outside diameter of proximal end 1324 measures 6.5 mm or 0.2559 inches (basic dimension) from distal endwall 1325a. The overall length of the nozzle 1313 is configured with a length parameter L16, measuring between a minimum/nominal/maximum length of 8.13 mm/8.38 mm/8.63 mm or 0.320 inches/0.3299 inches/ 0.3397 inches and the length of the 5% tapered conical mating surface of the outside wall 1318 is configured measuring a minimum/nominal length of 8.00 mm/8.30 mm or 0.3149 inches/0.3267 inches in a rotatable collar device. The inside opening 1341a or distal endwall 1325a is recessed, equal to or longer than the distal end of the collar 1304, and configured with a length parameter L13, measuring between a minimum/nominal/maximum length of −0.40/ 0.00/0.40 mm or −0.0155/0.00/0.0155 inches.

The depth of 5% female taper of the interior cavity 1326 and distal inside cavity 1326c of the female hub 1302, without or with lugs 1309, is configured with a length parameter L12 measuring between a minimum/nominal/ maximum length of 8.20 mm/8.45 mm/8.70 mm or 0.3228 inches/0.3326 inches/0.3425 inches between the open proximal end 1335 and endwall 1334. The proximal open end 1335 of the interior cavity 1326 of the hub 1302 is configured with an inside diameter parameter D10, measuring between a minimum/nominal/maximum length of 3.40 mm/3.43 mm/3.46 mm or 0.133 inches/0.135 inches/0.136 inches at the position L17, where the female taper of inside diameter of the hub 1302 measures 0.5 mm or 0.0196 inches (basic dimension) from the proximal end 1335 of the female hub 1302. The distal interior cavity 1326b of the female hub 1302 is configured with an inside diameter parameter D11, measuring between a minimum/nominal/maximum diameter of 3.07 mm/3.13 mm/3.19 mm or 0.1208 inches/0.1232 inches/0.1255 inches, at the position L11 where the female taper of inside diameter of the female hub 1302 measures 6.5 mm or 0.2559 inches (basic dimension) from proximal open end of hub 1302 of lock connector hub 1300. The interior cavity 1365*a* formed in the distal nozzle 1313*b* is configured with an inside diameter parameter D12, measuring between a nominal/maximum diameter of 1.5 mm/2.3 mm or 0.059 inches/0.0905 inches.

FIG. 31A is a cross-sectional side view of the low deadspace luer lock connector apparatus 1301A of the present invention in the Part 6, neuraxial or NRfit® configuration having a male connector 1303 joined to a female connector 1300. A volume-displacing member 1320 is positioned within the combined interior cavity 1306, 1326*c* and 1365, as shown in FIG. 30, and includes a through-passage 1327 connecting the proximal lumen 1310*a* with the distal lumen 1310*b*. The volume-displacing member 1320 is configured with an elongate body 1322 with an open distal end 1331 with an outside wall 1337*b* and an open proximal end 1330 with an interior cavity 1321*c* formed by a conical inside wall 1317 for funneling fluid or gas into the through-passage 1327. An annular ring 1358, having convex or geometric profile may be formed on the outside wall 1337*a* of the body 1322 as a stop or lip to limit and standardize the depth the nozzle 1313 can be positioned within the female hub 1302. The annular ring 1358 may also be configured to engage the distal endwall 1325*a*, as shown in FIG. 30, of the nozzle 1313 when the volume-displacing member 1320 is assembled into the female hub 1302. The proximal end 1330 includes an outside wall 1337*a* with an outside diameter configured to form a first liquid and air-tight seal 1323 with the inside diameter D13 of the inside wall 1341, as shown in FIG. 30, of the nozzle 1313 and the distal end 1331 includes an outside wall 1337*b* configured to form a second liquid and air-tight seal 1343 with the inside diameter D12 of the inside wall 1307*b* of the distal nozzle 1313*b*. A laminar flowpath 1138 is formed between the proximal lumen 1310*a* of the male connector 1303, the interior cavity 1321*c* and through-passage 1327 of the volume-displacing member 1320, the distal interior cavity 1365 and the distal lumen 1310*b* of the female connector 1300, separating the deadspace formed within interior cavity 1326*c* from the flowpath 1338. The seals 1323 and 1343 formed by the volume-displacing member 1320 also reduce the probability of the hazard created when anesthetic gases or reagents, such as divinyl ether, ethyl chloride, ethyl ether, and ethylene, that form flammable explosive mixtures with air, oxygen, or nitrous oxide, leak from the patient's anesthetic breathing circuit into the air of an operating room during delivery of the anesthesia.

FIG. 31B is a cross-sectional side view of the low deadspace NRfit® volume-displacing member 1320*b* of the present invention with a proximal end 1330*b* with an outside diameter substantially equal to D13, and a distal end 1331*b* with an outside diameter substantially equal to D12, with a medial body 1358*b* having a larger outside diameter configured to displace a portion of the interior cavity 1326*c* of the female hub 1302.

FIG. 31C is a cross-sectional front view of the low deadspace NRfit® apparatus of FIG. 31 in axis 31C-31C, with the through-passage 1327 of the volume-displacing member 1320 separated from and bypassing the deadspace formed within the interior cavity 1326*c*. A first liquid and air-tight seal 1323 is formed between the outside wall 1337*a* of the volume-displacing member 1320 and the inside wall 1341 of the nozzle 1313. A second liquid and air-tight seal 1333 is formed between the outside wall 1318 of the nozzle 1313 and the inside wall 1307*a* of the female hub 1302.

FIG. 31D is a cross-sectional front view of the low deadspace NRfit® apparatus of FIG. 31 in axis 31D-31D, with a through-passage 1327 formed within the volume-displacing member 1320. A liquid and air-tight seal 1343 is formed between the distal outside wall 1337*b* of the volume-displacing member 1320 and the inside wall 1307*b* of the distal nozzle 1313*b*.

FIG. 32 is a cross-sectional side view of one implementation of the low deadspace NRfit® apparatus 1301B of the present invention with a male connector 1303 with a male nozzle 1313 attached to a female connector 1300*a* with a female luer hub 1302*c* with a distal interior cavity 1326*c* with integrally-formed volume-displacing member 1320*a* with a body 1322*a* positioned within the interior cavity 1306 of a male nozzle 1313. The volume-displacing member 1320*a* is configured with a body 1322*a* with an open proximal end 1330*a* and tapered inside wall 1317*a* defining a conical interior cavity 1321*c* formed with a through-passage 1327*a* in communication with a lumen 1365*a* formed in the distal nozzle 1313*b* of the female hub 1302*c*. The tapered wall 1317*a* is configured to funnel and direct pressurized anesthetic fluid or gas from the proximal lumen 1310*a* through the inside through-passage 1327*a* and into the distal lumen 1365 formed within the distal nozzle 1313*b*. The volume-displacing member 1320*a* reduces the inside cubic volumetric capacity within the combined interior cavity formed between the male connector and female connector. The outside diameter of the body 1322*a* is configured to form a first liquid and air-tight seal 1323*a* between the outside wall 1337*a* of the volume-displacing member 1320*a* and the inside diameter D13 of the inside wall 1341 of the distal opening 1341*a*, as shown in FIG. 30, of the nozzle 1313 and a second liquid and air-tight seal 1333 is formed between the outside wall 1318 of the nozzle 1313 and the inside wall 1307*a* of the female hub 1302*c*. A laminar flowpath 1338*a* is formed between the proximal lumen 1310*a* of the male connector 1303, the interior cavity 1306 of the nozzle 1313, the interior cavity 1321*c* and through-passage 1327 and distal lumen 1310*b* of the female hub 1302*c*.

To conform with Table D.1 of Part 6: the flowrate of the neuraxial part/component to which the luer connector is applied follows: the flowrate within and between a Spinal needle (bolus) or Epidural/regional nerve block needle (bolus) of the present invention having a volume-displacing member is between 0 ml/hour (h) to 3,600; the flowrate within and between a Catheter connector (bolus) or Catheter connector (infusion) of the present invention having a volume-displacing member is between 0 ml/h to 1,500 ml/h; the flowrate within and between a Filter (infusion) or Filter (bolus) or Infusion line of the present invention having a volume-displacing member is between 0 ml/h to 600 ml/h, the flowrate within and between a Wound infiltration component or standard Syringe of the present invention having a volume-displacing member is between 0 ml/h to 3,600 ml/h; and the flowrate within and between a loss of resistance syringe of the present invention having a volume-displacing member is between 0 ml/h to 10,000 ml/h.

FIG. 33 illustrates a cross-sectional side view of the prior art luer lock connector apparatus 1401 shown in the enteral or ENfit configuration of the ISO Standard—Small bore connectors for liquids and gases in healthcare applications—Part 3: Connectors for enteral applications, with a male connector 1403 separated from a female connector 1400. The male connector 1403 is configured with an inside cavity 1406 of the male nozzle 1413 having an inside sidewall 1441. The nozzle 1413 includes a conical mating surface outside sidewall 1418 with a proximal end 1424 and a distal end 1425 with an endwall 1425a, surrounded by a fixed outside collar 1404 having inside threads 1408 for accepting the threads or lugs of the female luer hub connector 1400. The female connector 1400 is configured with proximal hub 1402 with a conical mating surface inside wall 1407 formed between an open proximal end 1435 and a distal endwall 1434, defining an interior cavity 1426 and a medial interior cavity 1426c. A distal male nozzle 1413b is configured with an inside wall 1407b formed with the endwall 1434 defining an interior cavity 1410b. The interior cavity 1426c is openly connected and formed between the interior cavity 1410b and cavity 1410b. The female connector 1400 may include at least one fin 1405, not shown here, to rotate the female hub 1402 onto the nozzle 1413 of the male connector 1403. When the connectors 1403 and 1400 are joined together, a deadspace is formed within the combined interior cavity 1406, 1426c and 1410b. The male connector 1403 and female connector 1400 are configured in a luer-lock configuration whereby the lugs or threads 1409 of the female hub 1402 form a lock-fit with the threads 1408 of the outside collar 1404 when the female connector 1400 is rotated onto the male connector. The female connector and male connector may also comprise a slip fit configuration, whereby lugs 1409 of the female connector 1400 and threaded collar 1404 of male connector 1403 are not included.

Per Part 3, the male nozzle 1413 is configured with an interior cavity 1406 with an inside sidewall 1441 and a distal inside opening 1441 having an inside diameter parameter D16, measuring between a nominal/maximum diameter of 0.00 mm/2.90 mm/2.95 mm or 0.00 inches/0.114 inches/ 0.116 inches. The male connector 1403 can be configured with a syringe, female hub, adapter or another luer device. The outside wall 1418 at the tip of the 6% male taper of the nozzle 1413 is configured with an outside diameter parameter D17, measuring between a minimum/nominal/maximum diameter of 5.36 mm/5.41 mm/5.46 mm or 0.211 inches/0.213 inches/0.215 inches. The length parameter L18 of the outside wall 1418 at the distal tip of the 6% male taper of the nozzle 1413 to the inside end of the collar 1404 is configured with a minimum length of 6.82 mm or 0.268 inches without a nominal or maximum length and the distal end of the 6% taper is formed with a distal frustoconical tip configured with an angle having a minimum/nominal/maximum parameter of 40°/45°/50°.

The depth of female taper of the interior cavity 1426 of the female hub 1402, without or with lugs 1409, is configured with a length parameter L19 measuring between a minimum/nominal/maximum length of 7.04/7.14 mm/7.24 mm or 0.277 inches/0.281 inches/0.285 from the open proximal end 1435 to the medial endwall 1434. The proximal open end 1435 of the interior cavity 1426 of the hub 1402 is configured with an inside diameter parameter D18, measuring between a minimum/nominal/maximum length of 5.64 mm/5.69 mm/5.74 mm or 222 inches/0.224 inches/ 0.226 inches. The distal lumen 1410b of the connector 1400 is configured with an inside sidewall 1407b having an inside diameter parameter D16, measuring between a nominal/ maximum diameter of 2.90 mm/2.95 mm or 114 inches/ 0.116 inches.

FIG. 34A is a cross-sectional side view of one implementation of the low deadspace ENfit apparatus 1401A of the present invention with a male luer connector 1403 with a proximal lumen 1410a and opposing male nozzle 1413, with an interior cavity 1406, as shown in FIG. 33, formed within the inside wall 1441 and an outside wall 1418, attached to a female luer connector 1400 with a hub 1402 with a distal interior cavity 1426c with a volume-displacing member 1420 with a body 1422 positioned within the interior cavity 1406 of the male nozzle 1413, as shown in FIG. 33, and distal lumen 1410b of the female connector 1400. The volume-displacing member 1420 is configured with an open proximal end 1430 and tapered inside wall 1417 defining an interior cavity 1421c formed with a through-passage 1427 in communication with the proximal lumen 1410a and the distal lumen 1410b formed in the distal nozzle 1413b of the female hub 1402. The tapered wall 1417 is configured to funnel and direct fluid, nutrition or gasses from proximal lumen 1410a through the volume displacing member 1420 and into the distal lumen 1410b. The outside diameter of the body 1422 is configured to form a first liquid and air-tight seal 1423 between the outside wall 1437 of the volume-displacing member 1420 and the inside diameter D16 of the inside wall 1441 of the nozzle 1413, and a second liquid and air-tight seal 1433 is formed between the outside wall 1418 and the inside diameter D16 of the inside wall 1407b of the distal interior cavity 1410b of the nozzle 1413b. A laminar flowpath 1438 is formed between the proximal lumen 1410a of the male connector 1403, through-passage 1427 of the volume-displacing member and distal lumen 1410b of the female connector 1400.

FIG. 34B is a cross-sectional front view of the low deadspace ENfit apparatus of FIG. 34A in axis 34B-34B, with the volume-displacing member 1420 positioned within the distal lumen 1410b of the female hub 1402. The through-passage 1427 traverses through and is separated from the distal interior cavity 1426c of the female hub 1402, as shown in FIG. 34. A liquid and air-tight seal 1443 is formed between the outside wall 1437 of the volume-displacing member 1420 and the inside diameter D16 of the inside wall 1441 of the nozzle 1413b.

FIG. 35A is a cross-sectional side view of the ENfit volume-displacing member 1420a of the present invention having an elongate body 1422a with a proximal end 1430a and a distal end 1431a with an enlarged medial body 1458a with opposing through-passages 1427a and 1427b formed along the outside wall 1437a.

FIG. 35B is a cross-sectional front view of the volume-displacing member of the of FIG. 35A in axis 35B-35B, with opposing through-passages 1427a and 1427b formed alongside the outside wall 1437a and the enlarged medial body 1458a.

FIG. 36A is a cross-sectional side view of the ENfit volume-displacing member 1420b of the present invention having an elongate body 1422b with an enlarged medial body 1458b with opposing through-passages 1427c and 1427d formed alongside the outside wall 1437b.

FIG. 36B is a cross-sectional front view of the volume-displacing member of the of FIG. 36A in axis 36B-36B, with opposing through-passages 1427c and 1427d formed alongside the outside wall 1437b.

To conform with Table F.1 of Part 3: the flowrate of the enteral part/component to which the luer connector is applied follows: the flowrate within and between a first connector and a second connector of the present invention configured with a volume-displacing member is between a minimum of 0.1 ml/hour (h) to a maximum of 3000 ml/hour water, Bolus (plunger): 200 ml/minimum water to a maximum 3000 ml/h, Gravity (0.5 kPa) (no plunger): 3000 ml/h.

According to one implementation of the present invention, FIG. 37A is a cross-sectional side view of the low deadspace luer-to-male luer adapter connector 1501 of the present invention connecting a first luer-lock syringe 3b with a second luer-lock syringe 3b. The adapter 1500 is configured with a through-passage 1521 formed between a first female hub 1502a with an inside conical sidewall 1507a and a distal endwall 1534a forming a first interior cavity 1526a, and an opposing female hub a 1502b with an inside conical sidewall 1507b and a distal endwall 1534b forming a second interior cavity 1526b. The first volume-displacing member 1520a is configured with a proximal body 1522a integrally-formed within the interior cavity 1526a at the distal endwall 1534a. The body 1522a is formed with an outside wall 1537a, as shown in FIG. 37B, configured to form a first liquid and air-tight seal 1523a with the inside diameter D3 of the opening 41a, as shown on FIG. 2A, of the male nozzle 13 of the first syringe, separating the interior cavity 1526a from the through-passage 1521. A second opposing volume-displacing member 1520b with a distal body 1522b is integrally-formed within the interior deadspace cavity 1526b at the distal endwall 1534b. A second liquid and air-tight seal 1523b is formed between the outside wall 1537b of the volume displacing member 1520b and the inside diameter D3 of the inside opening 41a, as shown on FIG. 2A, of the male nozzle 13 of the second syringe mirroring the first liquid and air-tight seal 1523a, separating the interior deadspace cavity 1526b from the through-passage 1521. The through-passage 1521 is formed from the proximal end of the first volume-displacing member 1520a, through the body 1522 of the adapter 1500 continuing through to the distal end of the second volume-displacing member 1520b. A first elongate channel 1527a is configured along outside wall 1537a and includes a tapered inside wall 1517a and connects with the through passage 1521 to form a vent configured to funnel and move fluid and air through the flowpath 1538 when the first filled syringe nozzle is pointing up and before the second syringe is attached to the distal female hub 1502b to complete the transfer or mixing of medicine or diluent between syringes. The second volume-displacing member also may include an elongate channel 1527b configured along the outside wall 1537a and includes a tapered inside wall 1517b and connects with the through passage 1521. The volume-displacing members 1520a and 1520b reduce the volumetric capacity of the flowpath 1538 formed within the interior cavities of the syringe nozzle and female hub.

FIG. 37B is a cross-sectional front view of the low deadspace male luer-to-male luer adapter of FIG. 37A in axis 37B-37B with a volume-displacing member 1520a positioned within a male nozzle 13. The volume-displacing member 1520a is configured with a body 1522a with an outside diameter <D3 and an elongate through-passage 1521. At least one elongate channel 1527b connected with the through-passage 1521 and interior cavity 106a of male nozzle 13, configured to form a flowpath for moving fluid and air or air bubbles being transferred from syringe to syringe through the luer adapter 1500. A liquid and air-tight seal 133 is formed between the outside wall 18 of the nozzle 13 and the inside wall 1507a of the female hub 1502a.

FIG. 37C is a cross-sectional front view of the low deadspace apparatus of FIG. 37A in axis 37C-37C comprising a volume-displacing member 1520a positioned within the inside diameter D3 of the distal opening 41a of a male nozzle 13 with a liquid and air-tight seal 1523a formed between the outside wall 1537a and the inside opening 41a of the nozzle 13. A through-passage 1521 is formed within the volume-displacing member 1520a.

FIG. 38A is a cross-sectional side view of a low deadspace fill needle adapter 1601 of the present invention with a fill needle 1600 configured with a female luer hub 1602, a distal needle 1612 with a blunt tip 1611 and a hollow lumen 1610 lumen connected with a through-passage 1621 of an opposing integrally-formed volume-displacing member 1620 formed within the interior cavity 1626 of a female hub 1602. The male nozzle 13 of the syringe 3 is shown within the interior cavity 1626 of the female hub 1602. The volume-displacing member 1620 includes an elongate body 1622 with an inside through-passage 1621 formed with at least one open channel 1627 configured along the outside wall 1637 openly connected with the interior cavity 106 of a male nozzle 13. The channel 1627 includes a tapered endwall 1617 configured as a vent to funnel and move fluid and air or air bubbles being transferred through the fill needle 1601. The volume-displacing member 1620 is configured to reduce the cubic volumetric capacity within the interior cavity 1626 of the female hub 1602 and interior cavity 106 of the male nozzle 13. The body 1622 is formed with an outside wall 1637 configured to form a liquid and air-tight seal 1623 with the inside diameter D3 of the opening 41a, as shown in FIG. 2A, of the male nozzle 13 of the syringe 3, separating the interior cavity 1626c from the through-passage 1621. The volume-displacing members 120. 120a, 120b, 120d/210e, 120f, 120g, 320, 320a, 320c/ 320d, or 320e of the present invention may be positioned within fill needle 1600 to reduce the deadspace within the interior cavity 106 of a male nozzle 13 and interior cavity 1626c of the female hub 1602.

FIG. 38B is a cross-sectional front view of the low deadspace apparatus of FIG. 38A in axis 38B-38B comprising a volume-displacing member 1620 positioned within the inside diameter D3 of the distal opening 41a of a male nozzle 13 with a first liquid and air-tight seal 1623 formed between the outside wall 1637 and the inside opening 41a of the nozzle 13, and a second liquid-tight and air-tight seal 133 is formed between the inside sidewall 1607 of the female hub 1602 and the outside wall 18 of the nozzle 13. A through-passage 1621 is formed within the volume-displacing member 1620.

Numerous exemplary implementations have been disclosed and described herein. It is to be appreciated however, that the present invention is in no way to be construed as to being limited to these examples.

What is claimed is:
1. A syringe comprising:
a hollow barrel configured to store a liquid medicant in an interior cavity therein;
a male nozzle extending distally from the hollow barrel and having an interior cavity that is in fluid communication with the interior cavity of the hollow barrel;
a needle having a proximal open end, a distal open end and a lumen extending between the proximal and distal open ends;
a female luer hub including a distal end portion having a through opening in which resides a proximal end portion of the needle, the female luer hub including an interior space in which resides at least a portion of the male nozzle, a distal end of the interior space being at least partially defined by an interior end wall of the female luer hub that faces and is spaced apart from an exterior end wall of the male nozzle such that a cavity exists between the interior end wall of the female luer hub and the exterior end wall of the male nozzle, the proximal open end of the needle opening into the cavity;
a first collar extending proximally from the interior end wall of the female luer hub, the first collar having a through opening in which a portion of the needle resides or in which is in fluid communication with the lumen of the needle, the first collar having an outside wall; and a volume displacing member disposed inside the interior cavity of the male nozzle, the volume displacing member including an elongate body having a closed proximal end portion and a first side opening located distal to the closed proximal end portion that fluidly communicates with a flow passage located inside the elongate body, a distal end of the volume displacing member including a second collar having an inside wall and an outside wall, an interior of the second collar is defined by the inside wall and is in fluid communication with the inside flow passage, the second collar being fit over the first collar such that the inside wall of the second collar abuts the outside wall of the first collar to form an air-tight and liquid-tight seal between the inside wall of the second collar and the outside wall of the first collar, an outside wall of the elongate body located between the first side opening and the second collar abutting an inner wall of a distal end portion of the male nozzle to form an air-tight and liquid-tight seal between them;

a first portion of the interior cavity of the male nozzle fluidly communicating the interior cavity of the hollow barrel with the first side opening of the elongate body of the volume displacing member such that a fluid flow path exists between the interior cavity of the hollow barrel to the open distal end of the needle.

2. The syringe according to claim 1, wherein the hollow barrel and male nozzle are singularly made to comprise a first monolithic structure.

3. The syringe according to claim 1, wherein first collar and female luer hub are singularly made to comprise a second monolithic structure.

4. The syringe according to claim 1, wherein the volume displacing member is a monolithic structure.

5. The syringe according to claim 1, wherein each of the first and second collars are annular collars.

6. The syringe according to claim 1, wherein the volume displacing member includes a second side opening located distal to the closed proximal end portion that fluidly communicates with the flow passage located inside the elongate body, a second portion of the interior cavity of the male nozzle fluidly communicating the interior cavity of the hollow barrel with the first side opening of the elongate body of the volume displacing member.

7. The syringe according to claim 5, wherein the first side opening is located on a first side of the elongate body and the second side opening is located on a second side of the elongate body, the second side being opposite the first side.

8. The syringe according to claim 1, wherein the female luer hub further comprises a groove that surrounds the first collar and in which resides at least a portion of the second collar, the groove having an inner wall abutting the outer wall of second collar to form an air-tight and liquid-tight seal between them.

9. The syringe according to claim 1, wherein the outside wall of the elongate body of the volume displacing member includes a protrusion that circumvents the elongate body, the protrusion having a surface that abuts a portion of the outer end wall of the male nozzle.

10. The syringe according to claim 1, wherein the outside wall of the elongate body of the volume displacing member includes a protrusion that circumvents the elongate body, the protrusion having a surface that abuts a portion of the outer end wall of the male nozzle to form an air-tight and liquid-tight seal between them.

11. The syringe according to claim 8, wherein the outside wall of the elongate body of the volume displacing member includes a protrusion that circumvents the elongate body, the protrusion having a surface that abuts a portion of the outer end wall of the male nozzle.

12. The syringe according to claim 8, wherein the outside wall of the elongate body of the volume displacing member includes a protrusion that circumvents the elongate body, the protrusion having a surface that abuts a portion of the outer end wall of the male nozzle to form an air-tight and liquid-tight seal between them.

13. The syringe according to claim 1, wherein the first collar is press-fit into the second collar.

14. The syringe according to claim 1, wherein proximal closed end of the elongate body of the volume displacing member is tapered.

15. The syringe according to claim 1, wherein the volume displacing member occupies at least 50 percent of interior cavity of the male nozzle.

16. The syringe according to claim 1, wherein the volume displacing member is made of plastic resin or metal.

17. The syringe according to claim 1, wherein the hollow barrel and male nozzle is made of plastic resin or metal.

18. The syringe according to claim 1, wherein the female luer hub is made of plastic resin or metal.

* * * * *

UNITED STATES PATENT AND TRADEMARK OFFICE
CERTIFICATE OF CORRECTION

| | |
|---|---|
| PATENT NO. | : 11,612,693 B1 |
| APPLICATION NO. | : 17/990155 |
| DATED | : March 28, 2023 |
| INVENTOR(S) | : Kuracina |

It is certified that error appears in the above-identified patent and that said Letters Patent is hereby corrected as shown below:

In the Claims

Column 27, Line 42, delete "L10" and replace with -- L9 --.

Signed and Sealed this
Thirtieth Day of May, 2023

Katherine Kelly Vidal
*Director of the United States Patent and Trademark Office*